US009233148B2

(12) United States Patent
Bogoch et al.

(10) Patent No.: US 9,233,148 B2
(45) Date of Patent: Jan. 12, 2016

(54) REPLIKIN-BASED COMPOUNDS FOR PREVENTION AND TREATMENT OF INFLUENZA AND METHODS OF DIFFERENTIATING INFECTIVITY AND LETHALITY IN INFLUENZA

(76) Inventors: Samuel Bogoch, New York, NY (US); Elenore S. Bogoch, New York, NY (US); Anne Elenore Borsanyi, New York, NY (US); Samuel Winston Bogoch, Oakland, CA (US)

( * ) Notice: Subject to any disclaimer, the term of this patent is extended or adjusted under 35 U.S.C. 154(b) by 826 days.

(21) Appl. No.: 12/581,112
(22) Filed: Oct. 16, 2009

(65) Prior Publication Data

US 2010/0215675 A1    Aug. 26, 2010

Related U.S. Application Data

(63) Continuation-in-part of application No. 12/538,027, filed on Aug. 7, 2009, which is a continuation-in-part of application No. 12/429,044, filed on Apr. 23, 2009, now abandoned, and a continuation-in-part of application No. PCT/US2009/041565, filed on Apr. 23, 2009.

(60) Provisional application No. 61/246,006, filed on Sep. 25, 2009, provisional application No. 61/185,160, filed on Jun. 8, 2009, provisional application No. 61/179,686, filed on May 19, 2009, provisional application No. 61/172,115, filed on Apr. 23, 2009, provisional application No. 61/143,618, filed on Jan. 9, 2009.

(51) Int. Cl.

| A61K 39/145 | (2006.01) |
| C07K 14/00 | (2006.01) |
| C07H 21/00 | (2006.01) |
| A61K 39/00 | (2006.01) |
| C07K 14/005 | (2006.01) |
| C07K 14/44 | (2006.01) |
| C07K 14/72 | (2006.01) |

(52) U.S. Cl.
CPC ............ *A61K 39/0011* (2013.01); *C07K 14/005* (2013.01); *C07K 14/44* (2013.01); *C07K 14/72* (2013.01); *A61K 39/00* (2013.01); *A61K 2039/542* (2013.01); *A61K 2039/552* (2013.01); *C12N 2760/16122* (2013.01); *C12N 2760/16222* (2013.01); *C12N 2770/24122* (2013.01); *C12N 2770/32022* (2013.01)

(58) Field of Classification Search
CPC ...... A61K 39/39; A61K 39/12; A61K 39/145
See application file for complete search history.

(56) References Cited

U.S. PATENT DOCUMENTS

| 4,132,769 A | 1/1979 | Osther |
| 5,104,854 A | 4/1992 | Schlesinger |
| 5,231,167 A | 7/1993 | Zanetti |
| 5,280,113 A | 1/1994 | Rademacher et al. |
| 5,679,352 A | 10/1997 | Chong et al. |
| 5,866,690 A | 2/1999 | Bogoch |
| 6,023,659 A | 2/2000 | Seilhamer |
| 6,070,126 A | 5/2000 | Kokolus |
| 6,090,406 A | 7/2000 | Popescu |
| 6,242,578 B1 | 6/2001 | Bogoch |
| 6,256,647 B1 | 7/2001 | Toh |
| 6,470,277 B1 | 10/2002 | Chin |
| 6,484,166 B1 | 11/2002 | Maynard |
| 6,638,505 B2 | 10/2003 | Bogoch |
| 7,132,291 B2 * | 11/2006 | Cardineau et al. ............ 435/468 |
| 7,176,275 B2 | 2/2007 | Bogoch |
| 7,189,800 B2 * | 3/2007 | Bogoch et al. ................ 530/300 |
| 7,267,942 B2 | 9/2007 | Peiris |
| 7,420,028 B2 | 9/2008 | Bogoch |
| 7,442,761 B2 | 10/2008 | Bogoch |
| 7,452,963 B2 | 11/2008 | Bogoch |
| 7,674,888 B2 | 3/2010 | Perron |
| 7,705,129 B2 | 4/2010 | Bogoch |
| 7,758,863 B2 | 7/2010 | Bogoch |
| 7,763,705 B2 | 7/2010 | Bogoch |
| 7,774,144 B2 | 8/2010 | Bogoch |
| 7,894,999 B2 | 2/2011 | Bogoch |
| 7,993,655 B2 * | 8/2011 | Webb et al. ................. 424/210.1 |
| 8,050,871 B2 | 11/2011 | Bogoch |
| 8,417,462 B2 | 4/2013 | Bogoch |
| 8,494,781 B2 | 7/2013 | Bogoch |
| 2002/0120106 A1 | 8/2002 | Bogoch |
| 2002/0151677 A1 | 10/2002 | Bogoch |
| 2003/0180328 A1 | 9/2003 | Bogoch |
| 2003/0194414 A1 | 10/2003 | Bogoch |

(Continued)

FOREIGN PATENT DOCUMENTS

| DE | 3628658 | 3/1988 |
| EP | 0 108 564 A1 | 5/1984 |

(Continued)

OTHER PUBLICATIONS

Jackwood et al. (Avian Diseases, 2009, vol. 53, p. 613-617).*
Aichele et al. (J. Exp.Med. 1995, vol. 182, p. 261-266).*
Ghanem et al. (Journal of Virology, Jul. 2007, vol. 81, p. 7801-7804).*
Poole et al. (FEBS, 2007, p. 5300-5306).*
PCT International Search Report, PCT/US2002/09240, Jan. 14, 2004, USPTO, International Searching Authority, Washington DC.
PCT International Preliminary Examination Report, PCT/US2002/09240, May 2, 2004, USPTO, International Preliminary Examination Authority, Alexandria, VA, USA.
PCT International Search Report, PCT/US2002/21494, May 30, 2003, USPTO, International Searching Authority, Washington DC.
PCT International Preliminary Examination Report, PCT/US2002/21494, Nov. 26, 2004, USPTO, International Searching Authority, Alexandria, VA, USA.

(Continued)

*Primary Examiner* — Agnieszka Boesen
(74) *Attorney, Agent, or Firm* — Daren P. Nicholson

(57) ABSTRACT

The present invention provides methods of differentiating the infectivity and lethality of isolates of influenza virus and provides compounds for diagnosing, preventing, and treating outbreaks of influenza virus including compounds for diagnosing, preventing, and treating across different strains of influenza virus.

22 Claims, 5 Drawing Sheets

(56) References Cited

U.S. PATENT DOCUMENTS

| | | |
|---|---|---|
| 2003/0195874 A1 | 10/2003 | Akaboshi |
| 2005/0129715 A1 | 6/2005 | Paterson |
| 2005/0202415 A1 | 9/2005 | Bogoch |
| 2005/0271676 A1 | 12/2005 | Sette |
| 2006/0024669 A1* | 2/2006 | Bogoch et al. ................ 435/5 |
| 2007/0026009 A1 | 2/2007 | Bogoch |
| 2007/0128217 A1 | 6/2007 | ter Meulen |
| 2008/0176217 A1 | 7/2008 | Bogoch |
| 2008/0241918 A1 | 10/2008 | Sasisekharan et al. |
| 2008/0260764 A1 | 10/2008 | Bogoch |
| 2009/0017052 A1 | 1/2009 | Bogoch |
| 2009/0041795 A1 | 2/2009 | Bogoch |
| 2009/0269367 A1 | 10/2009 | Bogoch et al. |

FOREIGN PATENT DOCUMENTS

| | | |
|---|---|---|
| IT | 98M10874 | 10/1999 |
| JP | 3-503166 | 7/1991 |
| JP | 8-287088 | 11/1996 |
| JP | 9121867 | 5/1997 |
| JP | 10-212300 | 8/1998 |
| JP | 11001493 | 1/1999 |
| JP | 2000-253876 | 9/2000 |
| KR | 10-1999-0008052 | 1/1999 |
| WO | 89/07112 | 10/1989 |
| WO | 9632106 | 10/1996 |
| WO | 96136436 | 11/1996 |
| WO | 0018351 | 4/2000 |
| WO | 00/52054 | 9/2000 |
| WO | 0104135 A2 | 1/2001 |
| WO | WO/02/24876 A2 * | 3/2002 |
| WO | 02085093 A2 | 10/2002 |
| WO | 03005880 A3 | 1/2003 |
| WO | 03803058 A2 | 10/2003 |
| WO | 2005010032 A2 | 2/2005 |
| WO | 2005004754 A2 | 11/2005 |
| WO | 2006088962 A2 | 8/2006 |
| WO | WO/2006/088962 A2 * | 8/2006 |
| WO | 2007022151 | 2/2007 |
| WO | 2007149715 | 12/2007 |
| WO | 2008060669 A2 | 5/2008 |
| WO | 2008060702 A2 | 5/2008 |
| WO | 2008121329 A2 | 10/2008 |
| WO | 2008140557 A2 | 11/2008 |
| WO | 2008143717 A2 | 11/2008 |
| WO | 2008156914 A2 | 12/2008 |
| WO | 2009132209 A2 | 10/2009 |
| WO | 2010017514 A2 | 2/2010 |

OTHER PUBLICATIONS

PCT International Search Report, PCT/US2003/08990, Dec. 7, 2005, International Searching Authority, USPTO, Alexandria, VA, USA.
PCT Written Opinion of the International Searching Authority, PCT/US2004/017936, Apr. 7, 2005, EPO, International Searching Authority, Munich, DE.
PCT International Search Report, PCT/US2004/017936, Apr. 28, 2005, EPO, International Searching Authority, Rijswijk, NL.
PCT International Preliminary Report on Patentability, PCT/US2004/017936, Apr. 13, 2007, USPTO, International Preliminary Examining Authority, Alexandria, VA, USA.
PCT International Search Report, PCT/US2005/014443, Oct. 21, 2006, EPO, International Searching Authority, Rijswijk, NL.
PCT Written Opinion of the International Searching Authority, PCT/US2005/014443, Apr. 12, 2006, EPO, International Searching Authority, Munich, DE.
PCT International Preliminary Report on Patentability, PCT/US2005/014443, Nov. 1, 2006, WIPO, International Bureau of WIPO, Geneva, Switzerland.
PCT International Search Report and Written Opinion PCT/US2006/05343, Sep. 25, 2007, USPTO, International Searching Authority, Alexandria, VA, USA.
PCT International Preliminary Report on Patentability, PCT/US2006/05343, Jul. 22, 2008, USPTO, International Preliminary Examining Authority, Alexandria, VA, USA.
PCT International Search Report and Written Opinion, PCT/US2007/069978, Jun. 10, 2008, EPO, International Searching Authority, Rijswijk, NL.
PCT International Search Report and Written Opinion, PCT/US2007/82436, Jan. 9, 2009, USPTO, International Searching Authority, Alexandria, VA, USA.
PCT International Search Report and Written Opinion, PCT/US2008/00645, Feb. 2, 2009, USPTO, International Searching Authority, Alexandria, VA, USA.
PCT International Search Report and Written Opinion, PCT/US2008/061336, Feb. 2, 2009, EPO, International Searching Authority, Rijswijk, NL.
PCT International Preliminary Report on Patentability, PCT/US2007/069978, Mar. 14, 2009, USPTO, International Preliminary Examining Authority, Alexandria, VA, USA.
EP Supplementary Search 99944002, Apr. 20, 2004, EPO, Munich, DE.
EP Supplementary Search 02736514.7, Mar. 9, 2006.
EP Supplementary Search 02752202.8, Mar. 10, 2006.
EP Supplementary Search 03721445.9, Dec. 12, 2006, EPO, International Searching Authority, Munich, DE.
EP Office Action 04785929.3, Sep. 1, 2008, EPO, Netherlands.
NZ Office Action 553983, Jul. 16, 2008, IPO, New Zealand.
EP Office Action 04785929.3, Feb. 2, 2009, EPO, Netherlands.
NZ Office Action 560415, Mar. 6, 2009, IPO, New Zealand.
JP Office Action, Application No. 2009-024307, Sep. 8, 2009, Japan.
US Office Action, U.S. Appl. No. 11/615,578, Oct. 21, 2009.
NCBI accession # gi 75059 Jul. 16, 1999.
NCBI Listing JQ0032, residues 74-82, May 11, 2000.
NCBI Entrez Protein AAK38298, Apr. 19, 2001, see sequence of HA (http:www.ncbi.nlm.nih.gov/entrez/viewer.fcgi?db=protein &id=13676825).
NCBI Accession No. NP 740460 (2000).
NCBI Blast Searching, Gene Gateway—Exploring Genes and Genetic Disorders, "Sequence similarity searching using NCBI Blast" (http:www.ORNL.gov/sci/techresources/Himan_Genome/chromosome/blast.shtml) (screenshot Apr. 27, 2005 by USPTO in U.S. Appl. No. 11/116,203).
NCBI Query Tutorial "Introduction" (http://www.ncbi.nim.nih.gov/Education/BLASTinfo/query_tutorial.html) (screenshot Apr. 27, 2005 by USPTO in U.S. Appl. No. 11/116,203).
NCBI Query Tutorial "Introduction to a BLAST Query" (http://www.ncbi.nim.nih.gov/Education/BLASTinfo/tut1.html) (screenshot Apr. 27, 2005 by USPTO in U.S. Appl. No. 11/116,203).
NCBI Query Tutorial "Setting up a BLAST Search" (http://www.ncbi.nim.nih.gov/Education/BLASTinfo/Blast_setup.html) (screenshot Apr. 27, 2005 by USPTO in U.S. Appl. No. 11/116,203).
PepBank entry 42800, corresponding to UniProt database entry P15516, Apr. 1, 1990, available at http://pepbank.mgh.harvard.edu, accessed Oct. 6, 2008.
UnitProt/Swiss-Prot database entry O89746 1 Influenza A virus (strain a/Chicken/Hong Kong/220/1997 H5N1 genotype Gs/Gd) Nov. 1, 1998.
NCBI Swiss-Prot Locus P33795, accessed Jul. 20, 2009.
3MOTIF—Search Instructions, 3motif in three Dimensions, article titles "Submitting a protein sequence": http://brutlag.stanford.edu/3motif/search_instr.html) (screenshot Apr. 27, 2005 by USPTO in U.S. Appl. No. 11/116,203).
Abrams M. B. et al., "Early Detection and Monitoring of cancer with the Anti-Malignin Antibody Test," Cancer detection and Prevention, XX, XX, vol. 18, No. 1, 1994, pp. 65-78, XP000673180, ISSN:0361-090X.
Atassi, M. Z. et al., "A novel approach for localization of the continuous protein antigenic sites by comprehensive synthetic surface scanning: Antibody and T cell activity to several influenza hemagglutinin synthetic sites," Immunological Communications, 1984, pp. 539-551, vol. 13, No. 6, Marcel Dekker, Inc. XP009062995, ISSN: 0090-0877.
Ben-Yedidia, T. et al., "Intranasal administration of peptide vaccine protects human/mouse radiation chimera from influenza infection," International Immunology, 1999, pp. 1043-1051, XP000914818, ISSN: 0953-8178.

(56) References Cited

OTHER PUBLICATIONS

Betakova et al., "The Vaccinia Virus A14.5L Gene Encodes a Hydrophobic 53-Amino-Acid Virion Membrane Protein That Enhances Virulence in Mice and Is Conserved among Vertebrate Poxviruses," Journal of Virology, vol. 74., No. 9, May 2000, p. 4085-4092.
Bioworld Today, "Anonymous: Other news to note," NLDB [Online] XP002511196, retrieved from STN Database Accession No. 2008: 64080 abstract Mar. 12, 2008.
Bogoch et al.: In vitro production of the general transformation antibody related to survival in human cancer patients; antimalignin antibody; Abstract, Cancer Detection and Prevention, 1988, vol. 12, Nos. 1-6, pp. 313-320. (Database Medline on STN National Library of Medicine, Bethesda, MD, USA) No. 89028479.
Bogoch et al. "In vitro production of the general transformation antibody related to survival in human cancer patients: antimalignin antibody," Cancer Detection and Prevention, Sep. 28, 1988, vol. 12, Nos. 1-6, pp. 313-320.
Bogoch, S. et al., "A Checklist for Suitability of Biomarkers as Surrogate Endpoints in Chemoprevention of Breast Cancer," Journal of Cellular Biochemistry, Supplement, Boston, US, vol. 19, pp. 173-185, XP009046492, ISSN: 0733-1959, 1994.
Bogoch et al., "Aglyco Pathology of Viral Receptors in Dementias," Annals of the New York Academy of Sciences, New York Academy of Sciences, New York Academy of Sciences, New York, NY, US, vol. 757, 1995, pp. 413-417, XP008003395, ISSN:0077-8923.
Bogoch et al., "Rapid replication and Replikintm structures: basis of the AMASRTest and CAVAXR," Cancer Detection and Prevention Online, Feb. 9, 2002, XP002350483.
Bogoch et al., "Replikins: The Chemistry of Rapid Replication," Begell House, Inc. NY, NY (2005).
Brown, L. R. et al., "Recognition of the influenza hemagglutinin by Class II MHC-restricted T lymphocytes and antibodies," Journal of Immunology, Oct. 14-15, 1991, pp. 2677-2684, vol. 147, No. 8, American Association of Immunologists, USA, XP002371257, ISSN: 0022-1767.
Brumeanu, T.M. et al., "Immunogenicity of a Contiguous T-B Synthetic Epitope of the A/PR/8/34 Influenza Virus," Journal of Virology, Jul. 1997, vol. 71, No. 7, pp. 5473-5480.
Bucher, D. et al., "M protein (M1) of influenza virus antigenic analysis and intracellular localization with monoclonal antibodies", J Virol. Sep. 1989; 63(9): pp. 3622-3633.
Carr C. M. et al., "A spring-loaded mechanism for the conformational change of influenza hemagglutinin," Cell, May 21, 1993, pp. 823-832, vol. 73, Cell Press, XP002059698, ISSN: 0092-8674.
Chambers, T.M. et al., "Antigenic and molecular characterization of subtype H13 hemagglutinin of influenza virus," Database NCBI on STN, Accession No. HMIVT2, Virology, pp. 180-188, abstract, 1989, 172(1).
Ekiert, D.C. et al, Influenza Virus Epitope Antibody Recognition of a Highly Conserved Science 324, 246 Apr. 10, 2009) Published online Feb. 26, 2009, 10.1126/science.1171491.
Gao, Identification and characterization of T helper epitopes in the nucleoprotein of influenza A virus, J. Immunol. 1989, vol. 143, pp. 3007-3014.
Gelder, C.M. et al., "Human CD4+ T-cell repertoire of response to influenza a virus hemagglutinin after recent natural infection," Journal of Virology, Dec. 1995, vol. 69, No. 12, pp. 7497-7506A.
Jackwood, M.W. "Efficacy of a Replikin Peptide Vaccine Against Low Pathogenicity Avian Influenza H5 Virus," Avian Diseases, Abstract, Pre-Print Jul. 4, 2009 at http://avdi.allenpress.com/avdionline/?request=get-abstract&doi=10.1637%2F8892-042509-ResNote.1.
Johansson et al., "Small, novel proteins from the mistletoe Pharadendron tementosum exhibit highly selective cytotoxicity to human breast cancer cells," Cell Mol. Life Sci, Jan. 2003, 60: 165-175.
Kazazic et al., "Mutational analysis of the role of charged residues in target-cell binding, potency and specificity of the pediocin-like bacteriocin sakacin P," Microbiology, (Jul. 2002) 148: 2019-27.
Keppeler et al., "Elongation of the N-acyl side chain of sialic acid in MDCK II cells inhibits influenza A virus infection," abstract, Biochemical and Biophysical Research Communications, Dec. 18, 1998, vol. 253, No. 2. Database Medline on STN, National Library of Medicine, (Bethesda, MD, USA), No. 99097253.
Kornblith P. L. et al., "Growth-inhibitory effect of diphenylhydantoin on murine astrocytomas," Neurosurgery, vol. 5, No. 2, pp. 259-63 (Aug. 1979), Medline, XP002199627.
Margalit et al., "Prediction of Immunodominant Helper T Cell Antigenic Sites From the Primary Sequence," Jour. of Immunology, vol. 138, 2213-2229, Apr. 1, 1987.
Marra, M. et al., "The Genome Sequence of the SARS-Associated Coronavirus," Science, American Association for the Advancement of Science, US, v. 300, No. 5624, p. 1399-1404, XP002269483, ISSN: 0036-8075, May 30, 2003.
Massung et al., "Potential virulence determinants in terminal regions of variola spallpox virus genome," Nature, vol. 366, Dec. 23/30, 1993, p. 748-751.
O'Donnell, F.T. et al., "Epidemiology and molecular characterization of co-circulating influenza A/H3N2 virus variants in children," Epidemiology and Infection, Jun. 2003, pp. 521-31, abstract, vol. 130, issue 3, The University of Texas-Houston School of Public Health, Houston, Texas. Database Medline U.S. National Library of Medicine (Bethesda, MD) Accession No. 2003:298060.
Orlando, C. et al., "A monoclonal antibody directed against the catalytic site of Bacillus anthracis adenylyl cyclase identifies a novel mammalian brain catalytic subunit," Biochemistry, 1992, pp. 3215-3222, vol. 31, American Chemical Society, XP002371438, ISSN: 0006-2960.
Pannifer, Crystal structure of the anthrax lethal factor, Nature, vol. 414, pp. 229-233 (Nov. 2001).
Patil et al., "Identification of a Talin-binding Site in the Integrin β3 Subunit Distinct from the NPLY Regulatory Motif of a Post-ligand Binding Functions," The Journal of Biological Chemistry, vol. 274, No. 1, Oct. 1, 1999, p. 28575-28583.
Qin, E. et al., "A Genome Sequence of Novel SARS-CoV Isolates: the Genotype, GD-Ins29, Leads to a Hypothesis of Viral Transmission in South China," Genomics Proteomics & Bioinformatics, vol. 1, No. 2, p. 101-107, XP001206098, ISSN: 1672-0229, May 2003.
Rodman, Toby C. et al., "Human Immunodeficiency Virus (HIV) Tat-reactive Antibodies Present in Normal HIV-negative Sera and Depleted in HIV-positive Sera. Identification of the Epitope," vol. 175, pp. 1247-1253, (May 1992).
Rota, P. et al., "Characterization of a Novel Coronavirus Associated with Severe Acute Respiratory Syndrome," Science, American Association for the Advancement of Science, US, v. 300, No. 5624, p. 1394-1399, XP002269482, ISSN: 0036-8075, May 30, 2003.
Schenk, S. et al., "Four recombinant isoforms of Cor a 1, the major allergen of hazel pollen, show different reactivities with allergen-specific T-lymphocyte clones," European Journal of Biochemistry, 1994, pp. 717-722, vol. 224, XP002371408, ISSN: 0014-2956.
Seal et al., "Elevation of Serum Protein-Bound Carbohydrates and Haptoglobin in Schizophrenia," Clinical Chemistry; Oct. 1966, vol. 12, No. 10, pp. 709-716.
Sharma et al., "Synthesis and Characterization of a Peptide Identified as a Functional element in αA-crystallin," The Journal of Biological Chemistry, vol. 275, No. 6, Feb. 11, 2000, p. 3767-3771.
Shi, Immunogenicity and in vitro protective efficacy of a recombinant multistage Plasmodium falciparum candidate vaccine, PNAS vol. 96, No. 4, pp. 1615-1620 (Feb. 1999).
Sui, J et al., "Structural and functional bases for broad-spectrum neutralization of avian and human influenza A viruses," Nature Structural & Molecular Biology, vol. 16 No. 3 (Mar. 2009), published online Feb. 22, 2009; doi:10.1038/nsmb.1566.
Tanaka, T. et al., "Efficient Generation of Antibodies to Oncoproteins by using Synthetic Peptide Antigens." Proceedings of the National Academy of Sciences of USA, National Academy of Science, Washington, D.C., US, v. 82, No. 10, p. 3400-3404, tables 1, Peptide 21, XP000113798, ISSN: 0027-8424, May 1, 1985.
Weber, E. et al., "Fine Mapping of a Peptide Sequence Containing an Antigenic Site Conserved Among Arenaviruses," Virology, vol. 164, p. 30-38 (1988).

(56) References Cited

OTHER PUBLICATIONS

Witteveldt, et al., "Protection of Penaeus monodon against White Spot Syndrome Virus by oral Vaccination," Journal of Virology, Feb. 2004, p. 2057-2061 vol. 78, No. 4, entire document, esp. p. 2060, col. 1.

Yasuko, A-O, et al., "Intranasal administration of adjuvant-combined recombinant influenza virus Ha vaccine protects mice from the lethal H5N1 virus infection." Microbes and Infection, vol. 8, Issues 12-13, pp. 2706-2714, Oct. 2006.

Zhao, Neutralizing monoclonal antibody against Anthrax lethal factor inhibits intoxication in a mouse model, Human Antibodies, vol. 12, pp. 129-135 (2003).

Replikins, Ltd. Press Release, "Replikins, Ltd. has discovered a group of virus peptides that predict whether a virus is rapidly replicating and whether it is likely to spread" (Apr. 21, 2006).

Replikins, Ltd. Press Release, "Virus Replication Discovery Helps Predict Epidemics" (Apr. 24, 2006).

Hendrickson, D., Mass High Tech, "Flu forecaster firm born" (Apr. 28, 2006).

Boggs, J, Diagnostics & Imaging Week, "Replikins: Predicting global epidemics replication data" (May 4, 2006).

Replikins, Ltd. Press Release, "Replikins' FluForecast® Software Pinpoints Change in Deadly Bird Flu Amino Acid Sequence in Humans" (Jun. 3, 2006).

Replikins, Ltd. Press Release, "Advance Warning of H5N1 Influenza Outbreaks May Be Found in Shrimp Virus Reservoirs" (Oct. 26, 2006).

Replikins, Ltd. Press Release, "Rising H5N1 'Bird Flu' High-Virulence Sequences Found by Replikins, Ltd." (Nov. 6, 2006).

Replikins, Ltd. Press Release, "Human H5N1 Virus Replikin Count Overtakes Levels in H5N1 'Bird Flu'" (Dec. 27, 2006).

Replikins, Ltd. Press Release, "Gene Segment Identified in Virulent Human H5N1 Viruses—Key Discovery May Enable Development of Vaccines, Therapeutics" (Jan. 25, 2007).

Replikins, Ltd. Press Release, "High Host Mortality Rate Quantitatively Related to High Virus Replikin Count" (Mar. 6, 2007).

Replikins, Ltd. Press Release, "FluForecast® Trial in 2006 Predicted High Human H5N1 Mortality in Indonesia" (May 9, 2007).

Replikins, Ltd. Press Release, "Indonesia Reports Experiencing Human H5N1 Mortality Increase, as Predicted Last Year by Replikins' FluForecast® Quantitative Virus Analysis" (Jun. 8, 2007).

Replikins, LLC Press Release, "Replikins, LLC Finds West Nile Virus Replikin Count™ Has Reached Its Highest Recorded Value" (Aug. 3, 2007).

Replikins, LLC Press Release, "AMAS Test Measures Lethal Replikin Gene Activity in Lung and Other Cancers" (Dec. 6, 2007).

Replikins, Ltd. Press Release, "Lethal Human H5N1 Influenza Virus Replikin Gene Still Upregulated" (Dec. 11, 2007).

Replikins, Ltd. Press Release, "FluForecast® Replikin Count™ Predicts That the H5N1 Cycle Which Began in 1996 is Now Over" (Feb. 11, 2008).

Replikins, Ltd. Press Release, "Replikins Oral Vaccine Synthesized in 7 days protects 91% of Shrimp Against Lethal Virus" (Mar. 11, 2008).

Replikins, Ltd. Press Release, "H1N1 Influenza Virus with Highest Replikin Count™ Since the 1918 Pandemic Identified in the U.S. and Austria" (Apr. 7, 2008).

Replikins, Ltd. Press Release, "Increases in West Nile Virus Replikin Concentrations Precede Increases in the Number of Human Cases" (May 1, 2008).

Replikins, Ltd. Press Release, "Highest replikin concentrations and cyclical behavior related to human mortality are found in malaria trypanosomes" (May 19, 2008).

Replikins, Ltd. Press Release, "H5N1 Virus Replikin Gene Counts Indicate a New More Virulent Influenza Cycle Has Begun" (Jun. 27, 2008).

Replikins, Ltd. Press Release, "A new way to predict outbreaks: replikin peptide concentration in H5N1 influenza virus genome as a marker for lethal outbreaks" (Nov. 12, 2008).

Replikins, Ltd. Press Release, "Cancer Mortality Increases With Cancer Cell Replikin Count" (Dec. 4, 2008).

Replikins, Ltd. Press Release, "Rising H9N2 Influenza Replikin Count Has Doubled That of H5N1" (Jan. 15, 2009).

Replikins, Ltd. Press Release, "Confirmation of Bogoch Replikins Influenza Patents by Harvard-CDC and Scripps-Crucell Data" (Mar. 20, 2009).

Replikins, Ltd. Press Release, "Replikins Provided Advance Warning of Mexican H1N1 "Swine Flu" Virus Outbreak" (Apr. 25, 2009).

Replikins, Ltd. Press Release, "First H1N1 Swine Flu Vaccine, Replikins-Based, Is Ready Now for Testing Worldwide" (May 4, 2009).

Replikins, Ltd. Press Release, Swine Flu (H1N1) Infectivity to Increase Markedly and Lethality to Remain Low According to Latest Replikin* Peptide Genomic Data (May 23, 2009).

Replikins, Ltd. Press Release, "Lethality of H1N1 Influenza Virus Increasing According to Latest Replikins Analysis of Virus Peptide Genomic Data" (Jun. 10, 2009).

Latest Replikins Data Predicts Continued High Level of H1N1 (Swine Flu) Infectivity and Lethality (Jul. 28, 2009).

H1N1 Lethality Replikin Count Decreases, Infectivity Remains High (Sep. 30, 2009).

A New H1N1 Genomic Data Shows Decrease in Replikin Count of Lethality Gene; Replikin Count of Infectivity Gene Remains High (Sep. 30, 2009).

Altschul, et al. (1990) J. Mol. Biol. 215:403-10.

Altschul, et al. (1997) Nucleic Acids Res. 25(17):3389-3402.

Biocomputing: Informatics and Genome Projects, Smith, D. W., ed., Academic Press, New York, 1993.

Brenner, H., "Long-term survival rates of cancer patients achieved by the end of the 20th century: a period analysis," The Lancet, 360 (Oct. 12, 2002), pp. 1131-1135.

Computational Molecular Biology, Lesk, A. M., ed., Oxford University Press, New York, 1988.

Computer Analysis of Sequence Data, Part 1, Griffin, A. M., and Griffin, H. G., eds., Humana Press, New Jersey, 1994.

Sequence Analysis in Molecular Biology, von Heinje, G., Academic Press, 1987.

Sequence Analysis Primer, Gribskov, M. and Devereux, J., eds., M Stockton Press, New York, 1991.

PCT International Search Report and Written Opinion PCT/US2009/041565, Jan. 25, 2010, EPO, International Searching Authority, Rijswijk, NL.

PCT International Preliminary Report on Patentability, PCT/US2009/061108, Nov. 3, 2011, WIPO, Geneva, CH.

EP Supplemental Search, EP 10 01 2945.1, Jun. 9, 2011, EPO, Munich, DE.

CA Office Action, CA 2,441,540, Jul. 11, 2011, CIPO, CA.

CN Office Action, CN 200580012974.0, Jul. 19, 2011, CIPO, CN.

JP Office Action, JP 2007-555371, Jul. 19, 2011, JPO.

EP Partial Search Report, EP 11 158 084.1, Oct. 7, 2011, EPO.

EP Partial Search Report, EP 11 158 093.2, Oct. 14, 2011, EPO.

U.S. Office Action, U.S. Appl. No. 12/688,372, Nov. 21, 2011, USPTO.

KR Office Action, KR 2006-7021152, Dec. 8, 2011, KIPO.

JP Office Action, JP 2007-510929, Aug. 30, 2011, JPO.

NCBI Accession No. NP_052803 (May 14, 1998).

ACML 01000595 database entry (May 1, 2009).

Buscaglia et al., "The repetitive domain of Trypanosoma cruzi trans-sialidase enhances the immune response against the catalytic domain," Journal of Infectious Diseases, University of Chicago Press, Chicago, IL, vol. 177, No. 2, Feb. 1, 1998, pp. 431-436.

Cross et al., "Studies on influenza haemagglutinin fusion peptide mutants generated by reverse genetics," The EMBO Journal vol. 20 No. 16 pp. 4432-4442, 2001.

Ferro et al., "The androgen receptor CAG repeat: a modifier of carcinogenesis?" Molecular and Cellular Endocrinology, 193, Jan. 1, 2002, pp. 109-120.

Guan et al., "Emergence of multiple genotypes of H5N1 avian influenza viruses in Hong Kong SAR," PNAS vol. 99, No. 13, Jun. 25, 2002, pp. 8950-8955.

Melville et al., "P58IPK, a novel cochaperone containing tetratricopeptide repeats and a J-domain with oncogenic potential,"

(56) References Cited

OTHER PUBLICATIONS

Database accession No. PREV200000253165; & CMLS Cellular and Molecular Life Sciences, vol. 57, No. 2, Feb. 2000 (2000-02), pp. 311-322, ISSN: 1420-682X.
Okuno et al., "A Common Neutralizing Epitope Conserved between the Hemagglutinins of Influenza A Virus H1 and H2 Strains," Journal of Virology, vol. 67, No. 5, May 1993, p. 2552-2558.
Simeckova-Rosenberg et al., "Protection of mice against lethal viral infection by synthetic peptides corresponding to B- and T-cell recognition sites of influenza A hemagglutinin," Vaccine, vol. 13, No. 10, pp. 927-932 (1995).
Smith et al., "Finding sequence motifs in groups of functionally related proteins," PNAS, vol. 87, pp. 826-830, Jan. 1990.
PCT Invitation to Pay Additional Fees and Communication Relating to the Results of the Partial International Search, PCT/US2009/061108, Mar. 8, 2010, EPO, Rijswijk, NL.
UnitProt A8DXX4, Journal of Virology, vol. 81, No. 21, Nov. 13, 2007, pp. 11612-11619.
Spackman et al., "Characterization of Low-Pathogenicity H5N1 Avian Influenza Viruses from North America," Journal of Virology, vol. 81, No. 21, Nov. 13, 2007, pp. 11612-11619.
Tompkins, S.M. et al., "Matrix protein 2 vaccination and protection against influenza viruses, including subtype H5N1," Emerging Infectious Diseases, vol. 13, No. 3, p. 426-435, Mar. 2007, available at www.cdc.gov/eid.
Adar, Y. et al., "A universal epitope-based influenza vaccine and its efficacy against H5N1," Vaccine, 27:2099-2107 (2009).
US Notice of Allowance, U.S. Appl. No. 11/923,559, Jun. 23, 2011.
US Response to Office Action, U.S. Appl. No. 11/755,597, Nov. 30, 2010.
US Office Action, U.S. Appl. No. 12/108,458, Dec. 27, 2010.
US Office Action, U.S. Appl. No. 12/170,763, Feb. 15, 2011.
US Office Action, U.S. Appl. No. 12/252,028, Feb. 15, 2011.
US Office Action, U.S. Appl. No. 12/495,306, Feb. 15, 2011.
US Office Action, U.S. Appl. No. 12/010,027, Feb. 16, 2011.
US Office Action, U.S. Appl. No. 12/688,372, Mar. 28, 2011.
SG Written Opinion, Application No. SG 200602420-2, Apr. 6, 2011.
US Office Action, U.S. Appl. No. 12/789,877, Jun. 8, 2011.
EP Supplemental Search, Application No. EP 10 01 2944, Apr. 20, 2011, EPO, Munich, DE.
UniProt C2W513 (Jun. 16, 2009).
Diggs et al. "Plasmodium falciparum: Passive immunization of Aotus lemurinus griselmembra with immune serum," Experimental Parasitology, vol. 80, Issue 2, Mar. 1995, pp. 291-296.
Frankel et al., "Activity of synthetic peptides from the Tat protein of human immunodeficiency virus type 1," Proc. Natl. Acad. Sci.USA, Oct. 1989, vol. 86, pp. 7397-7401.
He, Z. et al., "Identification of epitopes in cucumber mosaic virus using a phage-displayed random peptide library," J Gen Virol 1998, vol. 79, pp. 3145-3153 (accepted Aug. 21, 1998).
Kumar et al., "Cytotoxic T Cells Specific for the Circumsporozoite Protein of Plasmodium Falciparum," Nature, vol. 334, Jul. 21, 1988, pp. 258-260, XP002027064.
Lal et al., "Identification of T-cell determinants in natural immune responses to the Plasmodium falciparum apical membrane antigen (AMA-1) in an adult population exposed to malaria," Infection and Immunity, vol. 64, No. 3, Mar. 1996, pp. 1054-1059, XP055000060.
Ostroff, "Emerging infectious diseases 1997-1998: The role of molecular epidemiology," Memorias Do Instituto Oswaldo Cruz, vol. 94, No. 1, Jan. 1999, pp. 1-3, XP002636692.
Patarroyo et al., "Induction of protective immunity against experimental infection with malaria using synthetic peptides," Nature, vol. 328, No. 6131, Aug. 13, 1987, pp. 629-632.
Takahashi et al., "Antibody to Ras proteins in patients with colon cancer," Clin Cancer Res, Oct 1995, vol. 1, pp. 1071-1077.
Wang et al., "ORF390 of white spot syndrome virus genome is identified as a novel anti-apoptosis gene," Biochemical and Biophysical Research Communications 325 (Nov. 2004) 899-907.
Yao et al., "Linear epitopes of sperm whale myoglobin identified by polyclonal antibody screening of random peptide library" Int J Peptide Protein Res, Jun. 30, 1996, vol. 5, pp. 477-485.
PCT International Search Report and Written Opinion, PCT/US2009/061108, Jun. 11, 2010, EPO, Rijswik, NL.
PCT International Preliminary Report on Patentability, PCT/US2009/041565, Oct. 26, 2010, WIPO, Geneva, CH.
US Office Action, U.S. Appl. No. 11/755,597, May 14, 2010.
AU Office Action, Application No. 2006214332, Jun. 10, 2010.
US Office Action, U.S. Appl. No. 12/010,027, Jul. 21, 2010.
SG Written Opinion, Application No. SG 200602419-4, Aug. 3, 2010.
US Office Action, U.S. Appl. No. 12/495,306, Sep. 1, 2010.
US Office Action, U.S. Appl. No. 11/755,597, Sep. 30, 2010.
NCBI Accession No. AAW59548 (Jan. 24, 2005).
NCBI Accession No. DQ100549 (Jul. 6, 2005).
GenBank Accession No. AAV74400.1 (Dec. 5, 2005).
NCBI Accession No. ABE97631 (Jun. 27, 2006).
Fern, J. "Promiscuous malaria peptide epitope stimulates CD45Ra T cells from peripheral blood of nonexposed donors," J. Immunology 1992, vol. 148, pp. 907-913.
Liu et al. Science, Aug. 19, 2005; 309 (5738); 1206. Epub Jul. 6, 2005, "Highly pathogenic H5N1 influenza virus infection in migratory birds.".
Rodriguez et al., "Plasmodium falciparum EBA-175 kDa protein peptides which bind to human red blood cells." Parasitology (2000), vol. 120, pp. 225-235.

* cited by examiner

FIGURE 2

H5N1 Influenza Virus (Avian) Infectivity and Lethality

- Infectivity (Mean Annual Replikin Count for Hemaglutinin)
- Lethality (Mean Annual Replikin Count for pB1 Gene Area)
- T Standard Deviation

FIGURE 3

H1N1 Influenza Virus (Human)
Infectivity and Lethality (May 18, 2009)

- Infectivity (Mean Annual Replikin Count for Hemaglutinin)
- Lethality (Mean Annual Replikin Count for pB1 Gene Area)
- Standard Deviation

FIGURE 4

H1N1 Influenza Virus (Human)
Infectivity and Lethality (June 8, 2009)

■ Infectivity (Mean Annual Replikin Count for Hemagglutinin)
▨ Lethality (Mean Annual Replikin Count for pB1 Gene Area)
⊤ Standard Deviation Annual Mean Replikin Count

FIGURE 5

H1N1 Influenza Virus (Human)
Infectivity and Lethality (September 23, 2009)

SEQUENCE LISTING

<160> NUMBER OF SEQ ID NOS: 66

<210> SEQ ID NO 1
<211> LENGTH: 26
<212> TYPE: PRT
<213> ORGANISM: Influenza virus

<400> SEQUENCE: 1

His Ala Gln Asp Ile Leu Glu Lys Glu His Asn Gly Lys Leu Cys Ser
1               5                   10                  15

Leu Lys Gly Val Arg Pro Leu Ile Leu Lys
            20                  25

<210> SEQ ID NO 2
<211> LENGTH: 19
<212> TYPE: PRT
<213> ORGANISM: Influenza virus

```
<400> SEQUENCE: 2

Lys Glu His Asn Gly Lys Leu Cys Ser Leu Lys Gly Val Arg Pro Leu
1               5                   10                  15

Ile Leu Lys

<210> SEQ ID NO 3
<211> LENGTH: 29
<212> TYPE: PRT
<213> ORGANISM: Influenza virus

<400> SEQUENCE: 3

Lys Lys Asn Asn Ala Tyr Pro Thr Ile Lys Arg Thr Tyr Asn Asn Thr
1               5                   10                  15

Asn Val Glu Asp Leu Leu Ile Ile Trp Gly Ile His His
            20                  25

<210> SEQ ID NO 4
<211> LENGTH: 27
<212> TYPE: PRT
<213> ORGANISM: Influenza virus

<400> SEQUENCE: 4

His His Ser Asn Glu Gln Gly Ser Gly Tyr Ala Ala Asp Lys Glu Ser
1               5                   10                  15

Thr Gln Lys Ala Ile Asp Gly Ile Thr Asn Lys
            20                  25

<210> SEQ ID NO 5
<211> LENGTH: 21
<212> TYPE: PRT
<213> ORGANISM: Influenza virus

<400> SEQUENCE: 5

His Asp Ser Asn Val Lys Asn Leu Tyr Asp Lys Val Arg Leu Gln Leu
1               5                   10                  15

Arg Asp Asn Ala Lys
            20

<210> SEQ ID NO 6
<211> LENGTH: 22
<212> TYPE: PRT
<213> ORGANISM: Influenza virus

<400> SEQUENCE: 6

Lys Val Arg Leu Gln Leu Arg Asp Asn Ala Lys Glu Leu Gly Asn Gly
1               5                   10                  15

Cys Phe Glu Phe Tyr His
            20

<210> SEQ ID NO 7
<211> LENGTH: 17
<212> TYPE: PRT
<213> ORGANISM: Influenza virus

<400> SEQUENCE: 7

Lys Asp Val Met Glu Ser Met Asp Lys Glu Glu Met Glu Ile Thr Thr
1               5                   10                  15

His

<210> SEQ ID NO 8
<211> LENGTH: 15
```

```
<212> TYPE: PRT
<213> ORGANISM: Influenza virus

<400> SEQUENCE: 8

His Phe Gln Arg Lys Arg Arg Val Arg Asp Asn Met Thr Lys Lys
1               5                   10                  15

<210> SEQ ID NO 9
<211> LENGTH: 18
<212> TYPE: PRT
<213> ORGANISM: Influenza virus

<400> SEQUENCE: 9

Lys Lys Trp Ser His Lys Arg Thr Ile Gly Lys Lys Gln Arg Leu
1               5                   10                  15

Asn Lys

<210> SEQ ID NO 10
<211> LENGTH: 14
<212> TYPE: PRT
<213> ORGANISM: Influenza virus

<400> SEQUENCE: 10

His Lys Arg Thr Ile Gly Lys Lys Lys Gln Arg Leu Asn Lys
1               5                   10

<210> SEQ ID NO 11
<211> LENGTH: 26
<212> TYPE: PRT
<213> ORGANISM: Influenza virus

<400> SEQUENCE: 11

His Glu Gly Ile Gln Ala Gly Val Asp Arg Phe Tyr Arg Thr Cys Lys
1               5                   10                  15

Leu Val Gly Ile Asn Met Ser Lys Lys
            20                  25

<210> SEQ ID NO 12
<211> LENGTH: 35
<212> TYPE: PRT
<213> ORGANISM: Influenza virus

<400> SEQUENCE: 12

His Ser Trp Ile Pro Lys Arg Asn Arg Ser Ile Leu Asn Thr Ser Gln
1               5                   10                  15

Arg Gly Ile Leu Glu Asp Glu Gln Met Tyr Gln Lys Cys Cys Asn Leu
            20                  25                  30

Phe Glu Lys
        35

<210> SEQ ID NO 13
<211> LENGTH: 14
<212> TYPE: PRT
<213> ORGANISM: Influenza virus

<400> SEQUENCE: 13

His Phe Gln Arg Lys Arg Arg Val Arg Asp Asn Val Thr Lys
1               5                   10

<210> SEQ ID NO 14
<211> LENGTH: 13
<212> TYPE: PRT
<213> ORGANISM: Influenza virus
```

<400> SEQUENCE: 14

His Cys Gln Lys Thr Met Asn Gln Val Val Met Pro Lys
1               5                   10

<210> SEQ ID NO 15
<211> LENGTH: 13
<212> TYPE: PRT
<213> ORGANISM: Influenza virus

<400> SEQUENCE: 15

His Tyr Gln Lys Thr Met Asn Gln Val Val Met Pro Lys
1               5                   10

<210> SEQ ID NO 16
<211> LENGTH: 9
<212> TYPE: PRT
<213> ORGANISM: Influenza virus

<400> SEQUENCE: 16

Lys Arg Trp Arg Leu Phe Ser Lys His
1               5

<210> SEQ ID NO 17
<211> LENGTH: 8
<212> TYPE: PRT
<213> ORGANISM: Influenza virus

<400> SEQUENCE: 17

Lys Lys Lys His Lys Leu Asp Lys
1               5

<210> SEQ ID NO 18
<211> LENGTH: 50
<212> TYPE: PRT
<213> ORGANISM: Influenza virus
<220> FEATURE:
<221> NAME/KEY: MOD_RES
<222> LOCATION: (9)..(49)
<223> OTHER INFORMATION: Any amino acid and this region may encompass 1
      to 41 residues

<400> SEQUENCE: 18

Lys Lys Lys Gln Arg Leu Thr Lys Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa His
    50

<210> SEQ ID NO 19
<211> LENGTH: 14
<212> TYPE: PRT
<213> ORGANISM: Influenza virus

<400> SEQUENCE: 19

His Phe Gln Arg Lys Arg Arg Val Arg Asp Asn Met Thr Lys
1               5                   10

<210> SEQ ID NO 20
<211> LENGTH: 31
<212> TYPE: PRT

```
<213> ORGANISM: Influenza virus

<400> SEQUENCE: 20

His Phe Gln Arg Lys Arg Arg Val Arg Asp Asn Met Thr Lys L

Lys Met Asn Thr Gln Phe Thr Ala Val Gly Lys Glu Phe Asn His
1               5                   10                  15

<210> SEQ ID NO 27
<211> LENGTH: 20
<212> TYPE: PRT
<213> ORGANISM: Influenza virus

<400> SEQUENCE: 27

Lys Ser Gln Leu Lys Asn Asn Ala Lys Glu Ile Gly Asn Gly Cys Phe
1               5                   10                  15

Glu Phe Tyr His
            20

<210> SEQ ID NO 28
<211> LENGTH: 8
<212> TYPE: PRT
<213> ORGANISM: Influenza virus

<400> SEQUENCE: 28

Lys His Ser Asn Gly Thr Val Lys
1               5

<210> SEQ ID NO 29
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(26)
<223> OTHER INFORMATION: Any amino acid

<400> SEQUENCE: 29

His Ala Gln Asp Ile Leu Glu Lys Glu His Asn Gly Lys Leu Cys Ser
1               5                   10                  15

Leu Lys Gly Val Arg Pro Xaa Xaa Xaa Xaa Leu Ile Leu Lys
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (24)..(25)
<223> OTHER INFORMATION: Any amino acid

<400> SEQUENCE: 30

His Ala Gln Asp Xaa Ile Leu Glu Lys Glu His Asn Gly Lys Leu Cys
1               5                   10                  15

Xaa Ser Leu Lys Gly Val Arg Xaa Xaa Pro Leu Ile Leu Lys
            20                  25                  30

-continued

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Glu His Asn Gly Lys Leu Cys Ser Leu Lys Gly Lys
1               5                   10

<210> SEQ ID NO 32
<211> LENGTH: 29
<212> TYPE: PRT
<213> ORGANISM: Influenza virus

<400> SEQUENCE: 32

Lys Lys Gly Asn Ser Tyr Pro Lys Leu Ser Lys Ser Tyr Ile Asn Asp
1               5                   10                  15

Lys Gly Lys Glu Val Leu Val Leu Trp Gly Ile His His
            20                  25

<210> SEQ ID NO 33
<211> LENGTH: 28
<212> TYPE: PRT
<213> ORGANISM: Influenza virus

<400> SEQUENCE: 33

Lys Asn Gly Leu Tyr Pro Asn Leu Ser Lys Ser Tyr Ala Asn Asn Lys
1               5                   10                  15

Glu Lys Glu Val Leu Val Leu Trp Gly Val His His
            20                  25

<210> SEQ ID NO 34
<211> LENGTH: 22
<212> TYPE: PRT
<213> ORGANISM: Influenza virus

<400> SEQUENCE: 34

Lys Leu Ser Lys Ser Tyr Val Asn Asn Lys Gly Lys Glu Val Leu Val
1               5                   10                  15

Leu Trp Gly Val His His
            20

<210> SEQ ID NO 35
<211> LENGTH: 14
<212> TYPE: PRT
<213> ORGANISM: Influenza virus

<400> SEQUENCE: 35

Lys Phe Glu Ile Phe Pro Lys Thr Ser Ser Trp Pro Asn His
1               5                   10

<210> SEQ ID NO 36
<211> LENGTH: 19
<212> TYPE: PRT
<213> ORGANISM: Influenza virus

<400> SEQUENCE: 36

Lys Ser Tyr Val Asn Asn Lys Gly Lys Glu Val Leu Val Leu Trp Gly
1               5                   10                  15

Val His His

```
<210> SEQ ID NO 37
<211> LENGTH: 16
<212> TYPE: PRT
<213> ORGANISM: Influenza virus

<400> SEQUENCE: 37

His Pro Val Thr Ile Gly Glu Cys Pro Lys Tyr Val Arg Ser Thr Lys
1               5                   10                  15

<210> SEQ ID NO 38
<211> LENGTH: 8
<212> TYPE: PRT
<213> ORGANISM: Influenza virus

<400> SEQUENCE: 38

Lys Glu Phe Asn His Leu Glu Lys
1               5

<210> SEQ ID NO 39
<211> LENGTH: 12
<212> TYPE: PRT
<213> ORGANISM: Influenza virus

<400> SEQUENCE: 39

His Leu Glu Lys Arg Ile Glu Asn Leu Asn Lys Lys
1               5                   10

<210> SEQ ID NO 40
<211> LENGTH: 15
<212> TYPE: PRT
<213> ORGANISM: Influenza virus

<400> SEQUENCE: 40

Lys Met Asn Thr Gln Phe Thr Ala Val Gly Lys Glu Phe Asn His
1               5                   10                  15

<210> SEQ ID NO 41
<211> LENGTH: 8
<212> TYPE: PRT
<213> ORGANISM: Influenza virus

<400> SEQUENCE: 41

Lys His Ser Asn Gly Thr Val Lys
1               5

<210> SEQ ID NO 42
<211> LENGTH: 19
<212> TYPE: PRT
<213> ORGANISM: Influenza virus

<400> SEQUENCE: 42

Lys Ser Tyr Ile Asn Asp Lys Gly Lys Glu Val Leu Val Leu Trp Gly
1               5                   10                  15

Ile His His

<210> SEQ ID NO 43
<211> LENGTH: 13
<212> TYPE: PRT
<213> ORGANISM: Influenza virus

<400> SEQUENCE: 43

His Pro Ile Thr Ile Gly Lys Cys Pro Lys Tyr Val Lys
1               5                   10
```

<210> SEQ ID NO 44
<211> LENGTH: 8
<212> TYPE: PRT
<213> ORGANISM: Influenza virus

<400> SEQUENCE: 44

Lys His Asn G

Gly Lys

<210> SEQ ID NO 51
<211> LENGTH: 18
<212> TYPE: PRT
<213> ORGANISM: Influenza virus

<400> SEQUENCE: 51

His Asn Gly Lys Leu Cys Lys Leu Lys Gly Ile Ala Pro Leu Gln Leu
1               5                   10                  15

Gly Lys

<210> SEQ ID NO 52
<211> LENGTH: 20
<212> TYPE: PRT
<213> ORGANISM: Influenza virus

<400> SEQUENCE: 52

Lys Ser Gln Leu Lys Asn Asn Ala Lys Glu Ile Gly Asn Gly Cys Phe
1 5 10 15

Glu Phe Tyr His
20

<210> SEQ ID NO 53
<211> LENGTH: 16
<212> TYPE: PRT
<213> ORGANISM: Influenza virus

<400> SEQUENCE: 53

His Pro Val Thr Ile Gly Glu Cys Pro Lys Tyr Val Lys Ser Thr Lys
1 5 10 15

<210> SEQ ID NO 54
<211> LENGTH: 13
<212> TYPE: PRT
<213> ORGANISM: Influenza virus

<400> SEQUENCE: 54

His Asp Ser Asn Val Lys Asn Leu Tyr Glu Lys Val Lys
1 5 10

<210> SEQ ID NO 55
<211> LENGTH: 17
<212> TYPE: PRT
<213> ORGANISM: Influenza virus

<400> SEQUENCE: 55

His Asp Ser Asn Val Lys Asn Leu Tyr Glu Lys Val Lys Ser Gln Leu
1 5 10 15

Lys

<210> SEQ ID NO 56
<211> LENGTH: 16
<212> TYPE: PRT
<213> ORGANISM: Influenza virus

<400> SEQUENCE: 56

His Pro Val Thr Ile Gly Glu Cys Pro Lys Tyr Val Arg Ser Ala Lys
1 5 10 15

<210> SEQ ID NO 57
<211> LENGTH: 12

```
<212> TYPE: PRT
<213> ORGANISM: Influenza virus

<400> SEQUENCE: 57

His Lys Cys Asn Asn Glu Cys Met Glu Ser Val Lys
1               5                   10

<210> SEQ ID NO 58
<211> LENGTH: 18
<212> TYPE: PRT
<213> ORGANISM: Influenza virus

<400> SEQUENCE: 58

Lys Ser Tyr Val Asn Asn Lys Glu Lys Glu Val Leu Val Leu Trp Gly
1               5                   10                  15

Val His

<210> SEQ ID NO 59
<211> LENGTH: 16
<212> TYPE: PRT
<213> ORGANISM: Influenza virus

<400> SEQUENCE: 59

His Pro Ile Thr Ile Gly Glu Cys Pro Lys Tyr Val Lys Ser Thr Lys
1               5                   10                  15

<210> SEQ ID NO 60
<211> LENGTH: 12
<212> TYPE: PRT
<213> ORGANISM: Influenza virus

<400> SEQUENCE: 60

His Lys Cys Asp Asp Glu Cys Met Glu Ser Val Lys
1               5                   10

<210> SEQ ID NO 61
<211> LENGTH: 17
<212> TYPE: PRT
<213> ORGANISM: Influenza virus

<400> SEQUENCE: 61

His Asn Gly Lys Ser Ser Phe Tyr Lys Asn Leu Leu Trp Leu Thr Gly
1               5                   10                  15

Lys

<210> SEQ ID NO 62
<211> LENGTH: 12
<212> TYPE: PRT
<213> ORGANISM: Influenza virus

<400> SEQUENCE: 62

His Lys Cys Asn Asp Glu Cys Met Glu Ser Val Lys
1               5                   10

<210> SEQ ID NO 63
<211> LENGTH: 19
<212> TYPE: PRT
<213> ORGANISM: Influenza virus

<400> SEQUENCE: 63

Lys Ser Tyr Ala Asn Asn Lys Glu Lys Glu Val Leu Val Leu Trp Gly
1               5                   10                  15

Val His His
```

```
<210> SEQ ID NO 64
<211> LENGTH: 12
<212> TYPE: PRT
<213> ORGANISM: Influenza virus

<400> SEQUENCE: 64

His Tyr Ser Arg Lys Phe Thr Pro Glu Ile Ala Lys
1               5                   10

<210> SEQ ID NO 65
<211> LENGTH: 26
<212> TYPE: PRT
<213> ORGANISM: Influenza virus

<400> SEQUENCE: 65

His Asn Gly Glu Ser Ser Phe Tyr Arg Asn Leu Leu Trp Leu Thr Gly
1               5                   10                  15

Lys Asn Gly Leu Tyr Pro Asn Leu Ser Lys
            20                  25

<210> SEQ ID NO 66
<211> LENGTH: 22
<212> TYPE: PRT
<213> ORGANISM: Influenza virus

<400> SEQUENCE: 66

Lys Glu Ser Trp Ser Tyr Ile Val Glu Lys Pro Asn Pro Glu Asn Gly
1               5                   10                  15

Thr Cys Tyr Pro Gly His
            20
```

REPLIKIN-BASED COMPOUNDS FOR PREVENTION AND TREATMENT OF INFLUENZA AND METHODS OF DIFFERENTIATING INFECTIVITY AND LETHALITY IN INFLUENZA

This application claims priority to U.S. Provisional Appln. Ser. No. 61/246,006, filed Sep. 25, 2009, U.S. application Ser. No. 12/538,027, filed Aug. 7, 2009, U.S. Provisional Appln. Ser. No. 61/185,160, filed Jun. 8, 2009, U.S. Provisional Appln. Ser. No. 61/179,686, filed May 19, 2009, U.S. Provisional Appln. Ser. No. 61/172,115, filed Apr. 23, 2009, U.S. application Ser. No. 12/429,044, filed Apr. 23, 2009, and PCT/US09/41565, filed Apr. 23, 2009, each of which is incorporated herein by reference in its entirety. This application further incorporates by reference in their entireties, U.S. Provisional Appln. Ser. No. 61/143,618, filed Jan. 9, 2009, U.S. Provisional Appln. Ser. No. 61/087,354, filed Aug. 8, 2008, U.S. Provisional Appln. Ser. No. 61/054,010, filed May 16, 2008, U.S. application Ser. No. 12/108,458, filed Apr. 23, 2008, PCT/US2008/61336, filed Apr. 23, 2008, U.S. application Ser. No. 12/010,027, filed Jan. 18, 2008, U.S. Provisional Appln. Ser. No. 60/991,676, filed Nov. 30, 2007, U.S. application Ser. No. 11/923,559, filed Oct. 24, 2007, U.S. Provisional Appln. Ser. No. 60/982,336, filed Oct. 24, 2007, U.S. Provisional Appln. Ser. No. 60/982,333, filed Oct. 24, 2007, U.S. Provisional Appln. Ser. No. 60/982,338, filed Oct. 24, 2007, U.S. Provisional Appln. Ser. No. 60/935,816, filed Aug. 31, 2007, U.S. Provisional Appln. Ser. No. 60/935,499 filed Aug. 16, 2007, U.S. Provisional Appln. Ser. No. 60/954,743, filed Aug. 8, 2007, U.S. application Ser. No. 11/755,597, filed May 30, 2007, U.S. Provisional Appln. Ser. No. 60/898,097, filed Jan. 30, 2007, U.S. Provisional Appln. Ser. No. 60/880,966, filed Jan. 18, 2007, U.S. Provisional Appln. Ser. No. 60/853,744, filed Oct. 24, 2006, U.S. application Ser. No. 11/355,120, filed Feb. 16, 2006, U.S. application Ser. No. 11/116,203, filed Apr. 28, 2005, U.S. application Ser. No. 10/860,050, filed Jun. 4, 2004, now U.S. Pat. No. 7,442,761, U.S. application Ser. No. 10/189,437, filed Jul. 8, 2002, now U.S. Pat. No. 7,452,963, U.S. application Ser. No. 10/105,232, filed Mar. 26, 2002, now U.S. Pat. No. 7,189,800, U.S. application Ser. No. 09/984,057, filed Oct. 26, 2001, now U.S. Pat. No. 7,420,028, and U.S. application Ser. No. 09/984,056, filed Oct. 26, 2001, now U.S. Pat. No. 7,176,275, each in its entirety.

FIELD OF THE INVENTION

The present invention relates to therapies for preventing and treating influenza virus, methods of predicting and differentiating infectivity and lethality of influenza outbreaks, and compounds for diagnostic, therapeutic, and/or preventive purposes in influenza.

BACKGROUND OF THE INVENTION

Influenza is an acute respiratory illness of global importance in humans and animals (both domesticated and wild) including, but not limited to, horses, pigs, chickens, ducks, turkeys, ferrets, and wild birds. Virulent and lethal outbreaks of influenza continue to threaten global health. As demonstrated by the H1N1 influenza pandemic of 2009, researchers, government officials, and medical practitioners are acutely aware of the continuing threat of pandemics of virulent and lethal influenza requiring new methods of treatment and novel therapeutic compounds. Researchers, government officials, and medical practitioners have also believed, however, it was not possible to develop long term therapies against influenza viruses across strains and across time because the influenza virus is subject to such rapid mutation as it moves through a population (and subject to hosting in a large variety of non-human reservoirs), such that an effective therapy for one year in a particular strain is not expected to be effective in the years to come against that strain or against other strains of influenza virus. Researchers, government officials, and medical practitioners have nevertheless long understood that a therapy against influenza that could be applied across strains and/or across time would be immensely helpful in attacking the global threat of influenza. Such a therapy was simply not considered possible until now.

As such, until now, influenza vaccines have remained the most effective defense against influenza virus. However, because of the ability of the virus to mutate, and the availability of non-human host reservoirs, influenza has continued to remain an emergent or re-emergent infectious threat.

Traditionally, vaccines have been developed on a twice-yearly basis, based on post hoc hematological classification of the increasing number of emerging influenza virus strains. As such, the only basis for annual classification of influenza virus as present or absent in a given year was identification by serological testing of the hemagglutinin and neuraminidase proteins in an isolate of virus. The activity of a strain of influenza was, as a result, only recorded after the occurrence of an outbreak, never in advance.

Because of the delay inherent in traditional methods of surveillance, presently applied technology does not allow for the design of effective vaccines early in an outbreak and has not allowed for the design of vaccines that might apply to more than one outbreak over time or across strains. Furthermore, presently applied vaccine production technology delays the availability of vaccines even after an outbreak occurs since many months are needed for production of vaccines following vaccine design. As previous and current events make clear (such as the current H1N1 influenza pandemic of 2009), despite the best intentions of the vaccine industry, current biological technology cannot supply all of the world's 6 billion people and billions of animals in a timely manner with vaccines against emerging diseases. That is, using currently applied technology, vaccines against emerging diseases are not produced prior to global outbreak of the disease and often are not produced until the emerging disease outbreak has subsided.

The applicants' discovery of Replikin chemistry in the virus genome structure, however, now provides methods of predicting future outbreaks of strains of influenza virus and now provides methods of identifying conserved targets in emerging strains of influenza against which vaccines may be developed prior to or at the outset of an outbreak. Such vaccine development can be undertaken in as few as seven days.

When an outbreak of influenza is identified, one aspect of the outbreak that is useful to public health researchers and government officials is a differentiation of the infectivity and the lethality of the influenza virus strain that is the agent of the outbreak. An influenza virus strain that is both relatively more infective and relatively more lethal is an influenza strain that will likely cause increased morbidity and mortality in an outbreak. When public health researchers and government officials have advanced knowledge of the infectivity and lethality of an influenza strain, they have crucial additional time for preparations of vaccines and other health measures in advance of a spreading outbreak. Early differentiation of infectivity and lethality of a strain of influenza that is causing an outbreak is of significant importance and utility to those coordinating a response to the outbreak and to those designing vaccines and other health measures in response to an outbreak. For example, early differentiation of infectivity and lethality of a strain of influenza virus causing an outbreak allows for a design of therapies that target the infectivity of a virus, the lethality of a virus, or both, There is a continuing need in the art for quantitative methods of differentiating, preventing, and treating outbreaks caused by virulent strains of influenza. Because of the annual administration of influenza vaccines and the short period of time when a vaccine can be administered, strategies directed at improving vaccine coverage are of critical importance. There is additionally a continuing need in the art for therapies against influenza virus that apply across strains and across time.

Replikin peptides are a family of small peptides that have been correlated with the phenomenon of rapid replication in influenza, malaria, West Nile virus, foot and mouth disease, and many other pathogens. Replikin peptides have likewise been generally correlated with the phenomenon of rapid replication in viruses, organisms, and malignancies.

Identification of Replikin peptides has provided targets for detection and treatment of pathogens, including vaccine development against virulent pathogens such as influenza virus, malaria, West Nile virus, and foot and mouth disease virus. In general, knowledge of and identification of this family of peptides enables development of effective therapies and vaccines for any pathogen that harbors Replikins. The phenomenon of the association of Replikins with rapid replication and virulence has been fully described in U.S. Pat. No. 7,189,800; U.S. Pat. No. 7,176,275; U.S. Pat. No. 7,442, 761; and U.S. application Ser. No. 11/355,120. Both Replikin concentration (number of Replikins per 100 amino acids) and Replikin composition have been correlated with the functional phenomenon of rapid replication.

There is a continuing need for monitoring Replikin sequences in strains of influenza virus to identify compounds for therapies that respond to influenza mutations. There is also a need to develop Replikin-based therapies that are effective across strains and within strains as they mutate over time. There is an additional need to develop Replikin-based therapies that are active against the infectivity of influenza viruses and/or that are active against the lethality of influenza viruses.

SUMMARY OF THE INVENTION

The present invention provides methods of differentiating the infectivity of an influenza virus isolate or strain of influenza virus from the lethality of the influenza virus isolate or strain of influenza virus and compounds for diagnostic, therapeutic, and/or preventive purposes in influenza including any strain of influenza.

A first non-limiting aspect of the present invention provides an isolated or synthesized protein fragment, polypeptide, or peptide comprising at least one peptide A where peptide A is at least 30%, 40%, 50%, 60%, 70%, 80%, 90% or 95%, or 100%, homologous with at least one of SEQ ID NO(s): 1-12, 13-20, 21-28, and 32-66. In a non-limiting embodiment of the first aspect, the amino acid sequence of the protein fragment, polypeptide, or peptide partially matches the amino acid sequence of an expressed whole protein wherein at least one, five, ten, twenty, thirty, forty, fifty, one hundred, two hundred, three hundred, four hundred, five hundred or more amino acid residues of the amino acid sequence of the expressed whole protein are not present in the protein fragment, polypeptide, or peptide. In another non-limiting embodiment of the first aspect, the amino acid sequence of said protein fragment, polypeptide, or peptide partially matches the amino acid sequence of an expressed whole protein wherein at least one, ten, twenty, thirty, forty, fifty, sixty, seventy, eighty, ninety, one hundred, one hundred fifty, two hundred, two hundred fifty, three hundred, three hundred fifty, four hundred, four hundred fifty, five hundred, five hundred fifty or more amino acid residues of the amino acid sequence of at least one terminus of the expressed whole protein are not present at least one terminus of said protein fragment, polypeptide, or peptide.

In a further non-limiting embodiment of the first aspect of the present invention, the isolated or synthesized protein fragment, polypeptide, or peptide consists of 7 to about 50 amino acids comprising at least one peptide A, wherein said peptide A is at least 30%, 40%, 50%, 60%, 70%, 80%, 90%, 95%, or 100%, homologous with at least one of SEQ ID NO(s): 1-12, 13-20, 21-28, and 32-66. In another non-limiting embodiment, the isolated or synthesized protein fragment, polypeptide, or peptide consists of a peptide A that is 30%, 40%, 50%, 60%, 70%, 80%, 90%, 95%, or 100% homologous with at least one of SEQ ID NO(s): 1-12, 13-20, 21-28, and 32-66, where the length of peptide A is no more than one, five, ten, twenty, thirty, forty, or fifty amino acid residues longer than the sequence of SEQ ID NO(s): 1-12, 13-20, 21-28, and 32-66 with which it is homologous. In a further non-limiting embodiment, peptide A is no more than one, two, three, four, five, six, seven, eight, nine, or ten amino acid residues longer than the sequence of SEQ ID NO(s): 1-12, 13-20, 21-28, and 32-66 with which it is homologous.

In a further non-limiting embodiment of the first aspect of the present invention, the isolated or synthesized protein fragment, polypeptide, or peptide consists of any one of the peptides of SEQ ID NO(s): 1-12, 13-20, 21-28, and 32-66.

A further non-limiting embodiment provides a peptide consisting of SEQ ID NO(s): 1, 2, 3, 4, 5, 6, 7, 8, 9, 10, 11, or 12. A further non-limiting embodiment provides a peptide consisting of SEQ ID NO(s): 21, 22, 23, 24, 25, 26, 27, or 28.

A further non-limiting embodiment of the first aspect of the invention provides an isolated or synthesized protein fragment, polypeptide, or peptide comprising at least one peptide A, where peptide A is at least 30%, 40%, 50%, 60%, 70%, 80%, 90% or 95%, or 100%, homologous with at least one of SEQ ID NO(s): 32-66. Another non-limiting embodiment provides a peptide consisting of at least one of SEQ ID NO(s): 32-66. In a further non-limiting embodiment, any peptide of SEQ ID NO(s): 32-66 is provided as comprised in an immunogenic composition and/or comprised in a vaccine.

Another non-limiting embodiment of the first aspect of the invention provides a biosynthetic composition consisting essentially of a peptide of SEQ ID NO(s): 1-66. A further non-limiting embodiment provides a biosynthetic composition consisting of a peptide of SEQ ID NO(s): 1-66.

Another non-limiting embodiment of the first aspect of the invention provides a protein fragment, polypeptide, or peptide consisting essentially of at least one of SEQ ID NO(s): 1-20 or SEQ ID NO(s): 21-66.

In a non-limiting embodiment, an isolated protein fragment, polypeptide, or peptide is chemically synthesized by solid phase methods.

A second non-limiting aspect of the present invention provides an immunogenic composition comprising at least one protein fragment, polypeptide, or peptide of any one of the above-listed protein fragments, polypeptides, or peptides. In a non-limiting embodiment of the second aspect of the present invention, the immunogenic compound comprises at least one peptide of SEQ ID NO(s): 1-12, 13-20, 21-28, and 32-66. Another non-limiting embodiment provides an immunogenic composition comprising at least one peptide of SEQ ID NO(s): 1, 2, 3, 4, 5, 6, 7, 8, 9, 10, 11, and 12 and SEQ ID NO(s): 21, 22, 23, 24, 25, 26, 27, and 28.

A third non-limiting aspect of the present invention provides a vaccine comprising at least one protein fragment, polypeptide, or peptide of any one of the above-listed protein fragments, polypeptides, or peptides. In a non-limiting embodiment of the third aspect of the present invention, the vaccine comprises at least one peptide of SEQ ID NO(s): 1-12, 13-20, 21-28, and 32-66.

A fourth non-limiting aspect of the present invention provides a composition comprising one or more isolated or synthesized peptides that are 30%, 40%, 50%, 60%, 70%, 80%, 90%, or 95% or more homologous with at least one of the peptides of SEQ ID NO(s): 1-12, 13-20, 21-28, and 32-66. In a non-limiting embodiment, the composition comprises one or more isolated or synthesized peptides of SEQ ID NO(s): 1-12, 13-20, 21-28, and 32-66. In another non-limiting embodiment, the composition comprises two, three, four, five, six, seven, eight, nine, ten, eleven, twelve, thirteen, fourteen, fifteen, sixteen, seventeen, eighteen, nineteen, or twenty or more isolated or synthesized peptides of SEQ ID NO(s): 1-12, 13-20, 21-28, and 32-66. In a non-limiting embodiment, the composition comprises at least one of the peptides of SEQ ID NO(s): 1-12. In another non-limiting embodiment, the composition comprises a mixture of peptides, wherein the mixture comprises isolated or synthesized peptides of SEQ ID NO(s): 1-12. In another non-limiting embodiment, the composition comprises at least one of the peptides of SEQ ID NO(s): 1-12 and 21-28. In another non-limiting embodiment, the composition comprises a mixture of peptides, wherein the mixture comprises isolated or synthesized peptides of SEQ ID NO(s): 1-12 and 21-28. In a non-limiting embodiment, the composition comprises an approximately equal molar mixture of the isolated or synthesized peptides of SEQ ID NO(s): 1-12 or an approximately equal molar mixture of the isolated or synthesized peptides of SEQ ID NO(s): 1-12 and 21-28. In a further non-limiting embodiment, the composition comprises approximately equal weight of the isolated or synthesized peptides of SEQ ID NO(s): 1-12 or approximately equal weight of the isolated or synthesized peptides of SEQ ID NO(s): 1-12 and 21-28.

In another non-limiting embodiment, the composition comprises about 10% by weight SEQ ID NO: 1, about 9% by weight SEQ ID NO: 2, about 10% by weight SEQ ID NO: 3, about 6% by weight SEQ ID NO: 4, about 8% by weight SEQ ID NO: 5, about 8% by weight SEQ ID NO: 6, about 7% by weight SEQ ID NO: 7, about 6% by weight SEQ ID NO: 8, about 10% by weight SEQ ID NO: 9, about 8% by weight SEQ ID NO: 10, about 7% by weight SEQ ID NO: 11, and about 11% by weight SEQ ID NO: 12.

A fifth aspect of the present invention provides a vaccine comprising one or more isolated or synthesized peptides that are 30%, 40%, 50%, 60%, 70%, 80%, 90%, or 95% or more homologous with at least one of the peptides of SEQ ID NO(s): 1-12, 13-20, 21-28, and 32-66. In a non-limiting embodiment, the vaccine comprises one or more isolated or synthesized peptides of SEQ ID NO(s): 1-12, 13-20, 21-28, and 32-66. In another non-limiting embodiment, the vaccine comprises two, three, four, five, six, seven, eight, nine, ten, eleven, twelve, thirteen, fourteen, fifteen, sixteen, seventeen, eighteen, nineteen, or twenty or more isolated or synthesized peptides of SEQ ID NO(s): 1-12, 13-20, 21-28, and 32-66. In a non-limiting embodiment, the vaccine comprises at least one of the peptides of SEQ ID NO(s): 1-12. In another non-limiting embodiment, the vaccine comprises a mixture of peptides, wherein the mixture comprises isolated or synthesized peptides of SEQ ID NO(s): 1-12. In another non-limiting embodiment, the vaccine comprises at least one of the peptides of SEQ ID NO(s): 1-12 and 21-28. In another non-limiting embodiment, the vaccine comprises a mixture of peptides, wherein the mixture comprises isolated or synthesized peptides of SEQ ID NO(s): 1-12 and 21-28. In a non-limiting embodiment, the vaccine comprises an approximately equal molar mixture of the isolated or synthesized peptides of SEQ ID NO(s): 1-12 or an approximately equal molar mixture of the isolated or synthesized peptides of SEQ ID NO(s): 1-12 and 21-28. In a further non-limiting embodiment, the vaccine comprises approximately equal weight of the isolated or synthesized peptides of SEQ ID NO(s): 1-12 or approximately equal weight of the isolated or synthesized peptides of SEQ ID NO(s): 1-12 and 21-28.

In another non-limiting embodiment, the vaccine comprises about 10% by weight SEQ ID NO: 1, about 9% by weight SEQ ID NO: 2, about 10% by weight SEQ ID NO: 3, about 6% by weight SEQ ID NO: 4, about 8% by weight SEQ ID NO: 5, about 8% by weight SEQ ID NO: 6, about 7% by weight SEQ ID NO: 7, about 6% by weight SEQ ID NO: 8, about 10% by weight SEQ ID NO: 9, about 8% by weight SEQ ID NO: 10, about 7% by weight SEQ ID NO: 11, and about 11% by weight SEQ ID NO: 12. In a further non-limiting embodiment, the vaccine comprises a pharmaceutically acceptable carrier and/or adjuvant. In a further non-limiting embodiment, the vaccine is for the treatment or prevention of influenza virus infection. In a further non-limiting embodiment, the vaccine is directed against H1N1, H1N2, H2N2, H3N2, H3N8, H5N1, H5N2, H7N7, H7N2, H7N3, H9N2, H10N7, or any other strain of influenza A.

A sixth non-limiting aspect of the invention provides an antibody, antibody fragment, or binding agent that binds to at least a portion of an amino acid sequence of at least one protein fragment, polypeptide, or peptide comprising a peptide A, wherein the peptide A is 30%, 40%, 50%, 60%, 70%, 80%, 90%, or 95% or more homologous with at least one of the peptides of SEQ ID NO(s): 1-12, 13-20, 21-28, and 32-66. In a non-limiting embodiment of the sixth non-limiting aspect, the antibody, antibody fragment, or binding agent binds to at least a portion of an amino acid sequence that is 30%, 40%, 50%, 60%, 70%, 80%, 90%, or 95% or more homologous with at least one of the peptides of SEQ ID NO(s): 1-12, 13-20, 21-28, and 32-66. In another non-limiting embodiment, the antibody, antibody fragment, or binding agent binds to at least a portion of an amino acid sequence of at least one of SEQ ID NO(s): 1-12, 13-20, 21-28, and 32-66.

A seventh non-limiting aspect of the present invention provides an isolated or synthesized polypeptide or peptide comprising a peptide A that has about the same number of amino acid residues as a peptide B, where peptide B is one of the peptides of SEQ ID NO: 1-28, and where the lysine residues and histidine residues in peptide A are conserved as compared to the lysine residues and histidine residues in peptide B, wherein said isolated or synthesized polypeptide or peptide further comprises up to 100 more amino acid residues than does peptide A, and wherein said up to 100 more amino acid residues of said isolated or synthesized polypeptide or peptide are positioned to the amino-terminus and/or carboxy-terminus of the lysine or histidine termini of peptide A. In a non-limiting embodiment of the seventh aspect of the present invention, the up to 100 more amino acid residues is up to one, two, three, four, five, six, seven, eight, nine, ten, twenty, thirty, forty, or fifty more amino acid residues. In a further non-limiting embodiment, the isolated or synthesized polypeptide or peptide consists of peptide A.

A further non-limiting embodiment of the seventh aspect of the present invention provides an isolated or synthesized peptide consisting of:

(1) a peptide consisting of about 26 amino acid residues with a histidine residue within 5 residues of the amino-terminus of the peptide wherein the histidine residue is considered to reside at position 1, and wherein relative to position 1 there is a lysine residue at position 8, a histidine residue at position 10, a lysine residue at position 13, a lysine residue at position 18, and a lysine residue at position 26, and wherein up to five additional residues may be present on the carboxy-terminus of the peptide after the lysine residue at position 26;

(2) a peptide consisting of about 19 amino acid residues with a lysine residue within 5 residues of the amino-terminus of the peptide wherein the lysine residue is considered to reside at position 1, and wherein relative to position 1 there is a histidine residue at position 3, a lysine residue at position 6, a lysine residue at position 11, and a lysine residue at position 19, and wherein up to five additional residues may be present on the carboxy-terminus of the peptide after the lysine residue at position 19;

(3) a peptide consisting of about 29 amino acids residues with a lysine residue within 5 residues of the amino-terminus of the peptide wherein the lysine residue is considered to reside at position 1, and wherein relative to position 1 there is a lysine residue at position 2, a lysine residue at position 10, a histidine residue at position 28, and a histidine residue at position 29, and wherein up to five additional residues may be present on the carboxy-terminus of the peptide after the histidine residue at position 29;

(4) a peptide consisting of about 27 amino acid residues with a histidine residue within 5 residues of the amino-terminus of the peptide wherein the histidine residue is considered to reside at position 1, and wherein relative to position 1 there is a histidine residue at position 2, a lysine residue at position 14, a lysine residue at position 19, and a lysine residue at position 27, and wherein up to five additional residues may be present on the carboxy-terminus of the peptide after the lysine residue at position 27.

(5) a peptide consisting of about 21 amino acid residues with a histidine residue within 5 residues of the amino-terminus of the peptide wherein the histidine residue is considered to reside at position 1 and wherein relative to position 1 there is a lysine residue at position 6, a lysine residue at position 11, and a lysine residue at position 21, and wherein up to five additional residues may be present on the carboxy-terminus of the peptide after the lysine residue at position 21;

(6) a peptide consisting of about 22 amino acid residues with a lysine residue within 5 residues of the amino-terminus of the peptide wherein the lysine residue is considered to reside at position 1, and wherein relative to position 1 there is a lysine residue at position 11, and a histidine residue at position 22, and wherein up to five additional residues may be present on the carboxy-terminus of the peptide after the histidine residue at position 22;

(7) a peptide consisting of about 17 amino acids with a lysine residue within 5 residues of the amino-terminus of the peptide wherein the lysine residue is considered to reside at position 1, and wherein relative to position 1 there is a lysine residue at position 9, and a histidine residue at position 17, and wherein up to five additional residues may be present on the carboxy-terminus of the peptide after the histidine residue at position 17;

(8) a peptide consisting of about 15 amino acid residues with a histidine residue within 5 residues of the amino-terminus of the peptide wherein the histidine residue is considered to reside at position 1, and wherein relative to position 1 there is a lysine residue at position 5, a lysine residue at position 14, and a lysine residue at position 15, and wherein up to five additional residues may be present on the carboxy-terminus of the peptide after the lysine residue at position 15;

(9) a peptide of about 18 amino acid residues with a lysine residue within 5 residues of the amino-terminus of the peptide wherein the lysine residue is considered to reside at position 1, and wherein relative to position 1 there is a lysine residue at position 2, a histidine residue at position 5, a lysine residue at position 6, a lysine residue at positions 11, 12, and 13, and a lysine residue at position 18, and wherein up to five additional residues may be present on the carboxy-terminus of the peptide after the lysine residue at position 18;

(10) a peptide of about 14 amino acid residues with a histidine residue within 5 residues of the amino-terminus of the peptide wherein the histidine residue is considered to reside at position 1, and wherein relative to position 1 there is a lysine residue at position 2, a lysine residue at positions 7, 8, and 9, and a lysine residue at position 14, and wherein up to five additional residues may be present on the carboxy-terminus of the peptide after the lysine residue at position 14;

(11) a peptide of about 26 amino acid residues with a histidine residue within 5 residues of the amino-terminus of the peptide wherein the histidine residue is considered to reside at position 1, and wherein relative to position 1 there is a lysine residue at position 16, and a lysine residue at positions 24, 25, and 26, and wherein up to five additional residues may be present on the carboxy-terminus of the peptide after the lysine residue at position 26; or

(12) a peptide consisting of about 35 amino acid residues with a histidine residue within 5 residues of the amino terminus of the peptide wherein the histidine residue is considered to reside at position 1, and wherein relative to position 1 there is a lysine residue at position 6, a lysine residue at position 28, and a lysine residue at position 35, and wherein up to five additional residues may be present on the carboxy-terminus of the peptide after the lysine residue at position 35.

In a further non-limiting embodiment, the isolated or synthesized peptide has an amino-terminus at position 1 and has a carboxy-terminus at the amino acid residue for which a position is expressly numbered that is the farthest to the carboxy-terminus of the peptide.

An eighth non-limiting aspect of the present invention provides a method of making a vaccine comprising: selecting at least one isolated or synthesized protein fragment, polypeptide, or peptide comprising at least one peptide A, where peptide A is at least 30%, 40%, 50%, 60%, 70%, 80%, 90% or 95%, or 100%, homologous with at least one of SEQ ID NO(s): 1-12, 13-20, 21-28, and 32-66 as a component of a vaccine; and making said vaccine. In a non-limiting embodiment, the method of making a vaccine comprises: selecting at least one isolated or synthesized peptide of SEQ ID NO(s): 1-12, 13-20, 21-28, and 32-66 as at least one component; and making said vaccine with the at least one component.

In another non-limiting embodiment, the method of making a vaccine comprises selecting at least two, three, four, five, six, seven, eight, nine, ten, eleven, twelve, or more isolated or synthesized peptides of SEQ ID NO(s): 1-12, 13-20, 21-28, and 32-66 as the at least one component of said vaccine. In another non-limiting embodiment, the at least one isolated or synthesized protein fragment, polypeptide, or peptide has the same amino acid sequence as at least one protein fragment, polypeptide or peptide identified in an emerging strain of influenza virus up to six months, one year, two years, or three years prior to making said vaccine.

A ninth non-limiting aspect of the present invention provides a method for preventing or treating influenza virus infection comprising administering at least one isolated or synthesized protein fragment, polypeptide, or peptide comprising at least one peptide A, where peptide A is at least 30%, 40%, 50%, 60%, 70%, 80%, 90% or 95%, or 100%, homologous with at least one of SEQ ID NO(s): 1-12, 13-20, 21-28, and 32-66 to an animal or human. In a non-limiting embodiment, the at least one isolated or synthesized protein fragment, polypeptide, or peptide consists of at least one peptide A at least 30%, 40%, 50%, 60%, 70%, 80%, 90%, or 95% or more homologous with at least one of the peptides SEQ ID NO(s): 1-12, 13-20, 21-28, and 32-66. In another non-limiting embodiment, the at least one isolated or synthesized peptide of SEQ ID NO(s): 1-12, 13-20, 21-28, and 32-66 is administered to an animal or human. In another non-limiting embodiment of the invention, at least one agent is capable of binding at least a portion of said peptide A that is at least 30%, 40%, 50%, 60%, 70%, 80%, 90% or 95%, or 100%, homologous with at least one of SEQ ID NO(s): 1-12, 13-20, 21-28, and 32-66.

A tenth non-limiting aspect of the present invention provides an isolated or synthesized nucleic acid sequence that encodes a protein fragment, polypeptide, or peptide comprising at least one peptide A, where peptide A is at least 30%, 40%, 50%, 60%, 70%, 80%, 90% or 95%, or 100%, homologous with at least one of SEQ ID NO(s): 1-12, 13-20, 21-28, and 32-66. In a non-limiting embodiment, the isolated or synthesized nucleic acid sequence encodes for a peptide consisting of 7 to about 50 amino acid residues and comprising any one or more of the peptide sequences of SEQ ID NO(s): 1-12, 13-20, 21-28, and 32-66. In another non-limiting embodiment, the nucleic acid sequence encodes for a peptide that is at least 30%, 40%, 50%, 60%, 70%, 80%, 90%, or 95% or more homologous with at least one of the peptide sequences of SEQ ID NO(s): 1-12, 13-20, 21-28, and 32-66. In another non-limiting embodiment, the nucleic acid sequence encodes for a peptide that consists of at least one of the peptide sequences of SEQ ID NO(s): 1-12, 13-20, 21-28, and 32-66.

In another non-limiting embodiment of the tenth aspect of the present invention, the isolated or synthesized nucleic acid sequence is comprised in an immunogenic compound. In another non-limiting embodiment, the isolated or synthesized nucleic acid sequence is comprised in a vaccine.

Another non-limiting embodiment of the tenth aspect of the present invention provides an isolated or synthesized nucleic acid sequence that is antisense to a nucleic acid that encodes for a peptide that is at least 30%, 40%, 50%, 60%, 70%, 80%, 90%, or 95% or more homologous with at least one of the peptide sequences of SEQ ID NO(s): 1-12, 13-20, 21-28, and 32-66. Another non-limiting embodiment provides a small interfering nucleic acid sequence that is about 10 to about 50 nucleic acids in length and is 30%, 40%, 50%, 60%, 70%, 80%, 90%, 95% or more homologous with a nucleic acid that encodes for any portion of SEQ ID NO(s): 1-12, 13-20, 21-28, and 32-66 or is 30%, 40%, 50%, 60%, 70%, 80%, 90% or more homologous with a nucleic acid that is antisense to a nucleic acid that encodes for any portion of one of SEQ ID NO(s): 1-12, 13-20, 21-28, and 32-66. In another non-limiting embodiment the small interfering nucleic acid sequences is about 15 to about 45, about 20 to about 30, or about 21, 22, 23, 24, 25, 26, 27, 28, or 29 nucleic acids in length.

An eleventh non-limiting aspect of the present invention, provides for a vaccine comprising at least one protein fragment, polypeptide, or peptide comprising at least one peptide A, where peptide A is at least 30%, 40%, 50%, 60%, 70%, 80%, 90% or 95%, or 100%, homologous with at least one of SEQ ID NO(s): 1-12, 13-20, 21-28, and 32-66 isolated from a hemagglutinin protein area of influenza virus, or a synthesized version thereof, and at least one protein fragment, polypeptide, or peptide comprising at least one peptide A, where peptide A is at least 30%, 40%, 50%, 60%, 70%, 80%, 90% or 95%, or 100%, homologous with at least one of SEQ ID NO(s): 1-12, 13-20, 21-28, and 32-66 isolated from a protein or peptide encoded by a pB1 gene area of influenza virus, or a synthesized version thereof. In a non-limiting embodiment, the at least one protein fragment, polypeptide, or peptide is isolated from an isolate of influenza virus predicted to have a greater infectivity than at least one other isolate of influenza virus and the at least one protein fragment, polypeptide, or peptide isolated from the pB1 gene area, or synthesized version thereof, is isolated from an isolate of influenza virus predicted to have a greater lethality than at least one other isolate of influenza virus. In another non-limiting embodiment, the at least one protein fragment, polypeptide, or peptide isolated from the hemagglutinin protein area, or synthesized version thereof, is a plurality of protein fragments, polypeptides, and/or peptides isolated from the hemagglutinin protein area and the at least one protein fragment, polypeptide, or peptide isolated from the pB1 gene area, or synthesized version thereof, is a plurality of protein fragments, polypeptides, and/or peptides isolated from the pB1 gene area.

In a non-limiting embodiment, the at least one protein fragment, polypeptide, or peptide isolated from the hemagglutinin protein area, or synthesized version thereof, is at least one Replikin peptide isolated from the hemagglutinin protein area and the at least one protein fragment, polypeptide, or peptide isolated from the pB1 gene area, or synthesized version thereof, is at least one Replikin peptide isolated from the pB1 gene area. In a non-limiting embodiment, the at least one Replikin peptide isolated from a hemagglutinin protein area, or synthesized version thereof, is a plurality of Replikin peptides isolated from a hemagglutinin protein area and the at least one Replikin peptide isolated from a pB1 gene area, or synthesized version thereof, is a plurality of Replikin peptides isolated from a pB1 gene area. In a non-limiting embodiment, the plurality of Replikin peptides isolated from a hemagglutinin protein area, or synthesized version thereof, is a plurality of the shortest Replikin peptides identified in an influenza virus isolate or a plurality of influenza virus isolates predicted to have a greater infectivity than at least one other isolate of influenza virus and said plurality of Replikin peptides isolated from a pB1 gene area, or synthesized version thereof, is a plurality of the shortest Replikin peptides identified in an influenza virus isolate or a plurality of influenza virus isolates predicted to have a greater lethality than at least one other isolate of influenza virus.

In a non-limiting embodiment, the vaccine is directed against influenza A, influenza B, or influenza C. In a further non-limiting embodiment, the vaccine is directed against H1N1, H1N2, H2N2, H3N2, H3N8, H5N1, H5N2, H7N7, H7N2, H7N3, H9N2, H10N7, or any other strain of influenza A virus.

A twelfth non-limiting aspect of the present invention provides a method of making a vaccine comprising: selecting at least one peptide A, wherein said peptide A is at least 30%, 40%, 50%, 60%, 70%, 80%, 90% or 95%, or 100%, homologous with at least one of SEQ ID NO(s): 1-12, 13-20, 21-28, and 32-66 isolated from a hemagglutinin protein area (or a synthesized version thereof) as a component of said vaccine; and selecting at least one peptide B, wherein said peptide B is at least 30%, 40%, 50%, 60%, 70%, 80%, 90% or 95%, or 100%, homologous with at least one of SEQ ID NO(s): 1-12, 13-20, 21-28, and 32-66 isolated from a pB1 gene area (or a synthesized version thereof) as a component of said vaccine and making said vaccine comprising said components.

In a non-limiting embodiment, a method of making a vaccine comprises: identifying (1) at least one protein, protein fragment, polypeptide, or peptide of a hemagglutinin protein area in or derived from an isolate of influenza virus having relatively greater infectivity than another isolate of influenza virus or a plurality of isolates of influenza viruses, and (2) at least one protein, protein fragment, polypeptide, or peptide of a pB1 gene area in or derived from an isolate of influenza virus having relatively greater lethality than another isolate of influenza virus or a plurality of isolates of influenza virus; and combining said at least one protein, protein fragment, polypeptide, or peptide of a hemagglutinin protein area and said at least one protein, protein fragment, polypeptide, or peptide of a pB1 gene area to form a vaccine.

In another non-limiting embodiment of the twelfth aspect of the present invention, a method of differentiating the relative infectivity of isolate A of influenza virus or a plurality of isolates A of influenza virus from the relative infectivity of isolate B of influenza virus or a plurality of isolates B of influenza virus and the relative lethality of isolate A of influenza virus or a plurality of isolates A of influenza virus from the relative lethality of isolate B of influenza virus or a plurality of isolates B of influenza virus is provided comprising:
  comparing the Replikin Count of the hemagglutinin protein area of isolate A or the mean Replikin Count of the hemagglutinin protein areas of a plurality of isolates A to the Replikin Count of the hemagglutinin protein area of isolate B or the mean Replikin Count of the hemagglutinin protein area of a plurality of isolates B;
  comparing the Replikin Count of the pB1 gene area of isolate A or the mean Replikin Count of the pB1 gene area of a plurality of isolates A to the Replikin Count of the pB1 gene area of isolate B or the mean Replikin Count of the pB1 gene area of a plurality of isolates B; and
  differentiating the relative infectivity of isolate A or a plurality of isolates A from the relative infectivity of isolate B or a plurality of isolates B and the relative lethality of isolate A or a plurality of isolates A from the relative lethality of isolate B or a plurality of isolates B.

In another non-limiting embodiment, the isolate A or the plurality of isolates A is from a different region or time from the isolate B or the plurality of isolates B.

Another non-limiting embodiment provides a method of differentiating a predicted future relative infectivity of at least one strain A of influenza virus as compared to a time $T_0$ from a predicted future relative lethality of said at least one strain A of influenza virus as compared to time $T_0$ comprising:
  comparing a trend of Replikin Counts in the hemagglutinin protein area of a plurality of isolates of strain A ending at time $T_0$, wherein said isolates are isolated at different time periods including time $T_0$, to a trend of Replikin Counts in the pB1 gene area of a plurality of isolates of strain A ending at time $T_0$, wherein said isolates are isolated at different time periods including time $T_0$, and
  differentiating the future relative infectivity of said at least one strain A from the future relative lethality of said at least one strain A.

BRIEF DESCRIPTION OF THE DRAWINGS

FIG. 1 illustrates that only one of seven (14%) chickens tested in Group 3 (vaccinated and challenged with virus) was observed to produce antibody in serum seven days after challenge while four of seven chickens (57%) tested in Group 4 (not vaccinated but challenged) was observed to produce antibody in serum seven days after challenge. FIG. 1 further illustrates that only three of six chickens (50%) tested in Group 3 were observed to produce antibody in serum fourteen days after challenge while seven of nine (78%) chickens tested in Group 4 were observed to produce antibody in serum fourteen days after challenge. FIG. 1 further illustrates that two of seven (29%) chickens tested in Group 3 were observed to produce antibody in serum twenty-one days after challenge while three of nine (33%) of chickens tested in Group 4 were observed to produce antibody in serum twenty-one days after challenge. In the vaccine control (Group 2), six of six tested chickens (100%) were observed to produce antibody in serum 14 days after challenge while no chickens tested on day 7 or 21 following challenge were observed to produce antibody in serum. In the negative control (Group 1), no chickens were observed to produce antibody in serum on any day of testing. In combination with data provided in Table 2 (in Example 1 below), which demonstrates that no H5N1 virus was observed by PCR detection in feces or saliva for chickens in Groups 1, 2, and 3 (negative control, vaccine control, a vaccine/challenge groups, respectively) and that H5N1 virus was observed by PCR detection in feces and saliva for all chickens in Group 4 (challenge control), one of ordinary skill in the art concludes that chickens in the vaccinated and challenged group (Group 3) were provided a measure of protection from the challenge with Low-Path H5N1 on day 28 following hatch.

FIG. 2 illustrates a double differentiation between the infectivity and the lethality of isolates of H5N1 isolated between 2004 and 2008. In FIG. 2, the black columns represent the mean annual Replikin Count for hemagglutinin protein area sequences of isolates of H5N1 influenza virus publicly available at www.pubmed.com for a given year between 2004 and 2008. Standard deviation is denoted by the capped line on top of the black columns. The hemagglutinin protein area is associated with infectivity in influenza. The gray columns represent the mean annual Replikin Count for sequences from the pB1 gene area of isolates of H5N1 influenza virus publicly available at www.pubmed.com for a given year between 2004 and 2008. Standard deviation is denoted by the capped line on top of the gray columns. The pB1 gene area of influenza is associated with lethality in influenza. The data for FIG. 2 is disclosed in Table 3 in Example 2 below. FIG. 2 illustrates that Replikin Count for the hemagglutinin protein area is differentiable from Replikin Count for the pB1 gene area and that infectivity properties in H5N1 are differentiable from lethality properties in H5N1. The data in FIG. 2 corresponds to epidemiological data in H5N1. Human mortality (related to the lethality property of the pB1 gene area) has increased in H5N1 from 1997 through at least 2007, when mortality rates reached as high as 80% in Indonesia. Mortality rates have remained high since then with the World Health Organization estimating a mortality rate of at least 60% in the current outbreak of H5N1 influenza. Infectivity rates, on the other hand, have remained very low in H5N1 with highly limited possible human-to-human transmission.

Figure 1:
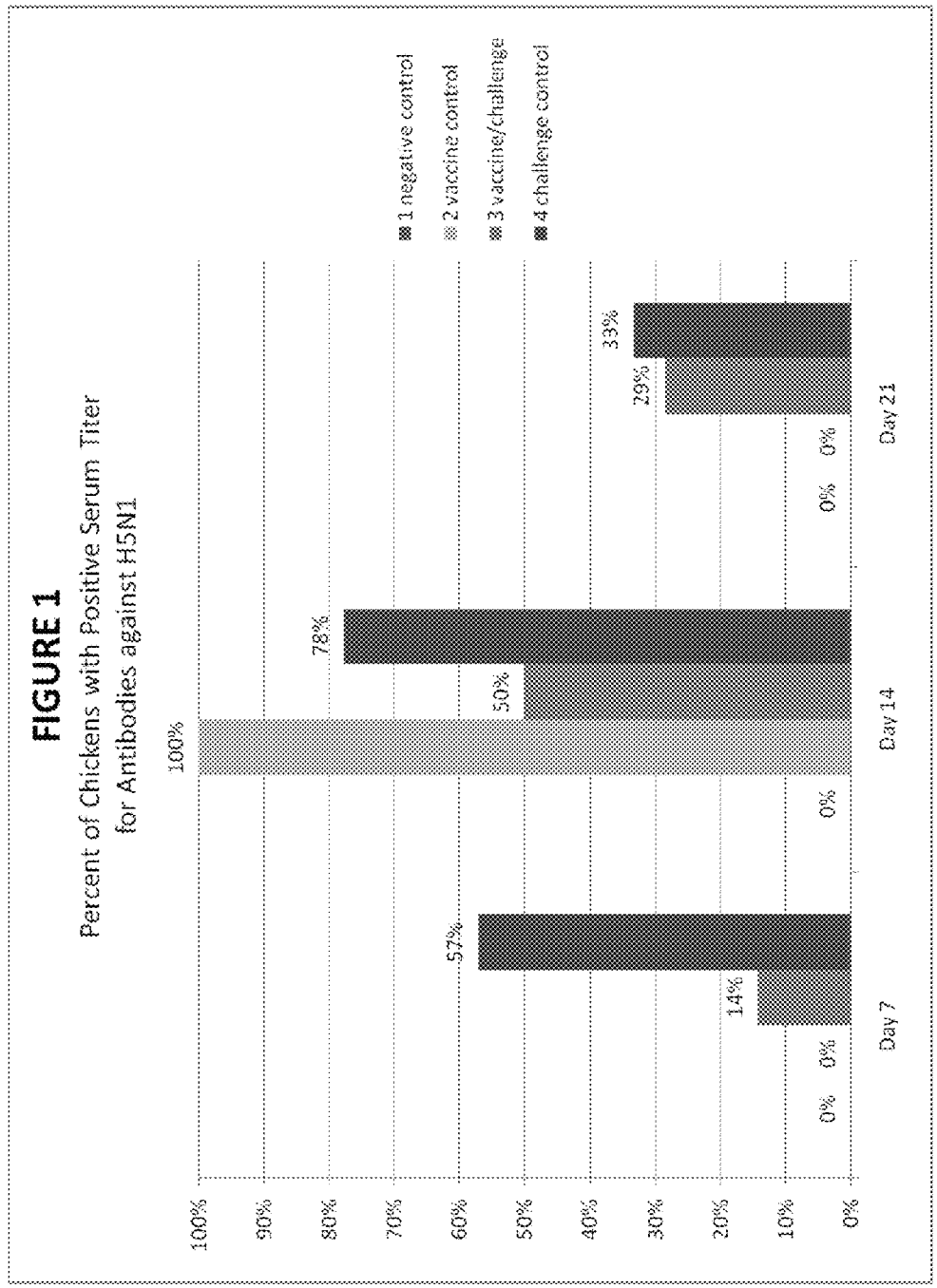
FIG. 1 illustrates an immune response with protective effect following administration of a vaccine comprising a mixture of peptides of SEQ ID NO(s): 1-12 to chickens later challenged with Low-Path H5N1 virus. Eighty chickens were divided into four groups of twenty chickens each on a first day after hatch. Group 1 was a negative control subjected to neither vaccination nor infection with the Low-Path H5N1 virus. Group 2 was a vaccine control subjected to vaccination intranasally on day 1 after hatch, intraocularly on day 7 after hatch, and via spray inhalation on day 14 after hatch. Group 2 was not subject to infection with the Low-Path H5N1 virus. Group 3 was subjected to vaccination on the same schedule as Group 2 and Low-Path H5N1 was introduced to the soft palate of the chickens on day 28. Group 4 was a challenged control that was not vaccinated but was infected with H5N1 on day 28 via the soft palate. On the seventh, fourteenth, and twenty-first days following challenge on day 28, between six and nine chickens from each group were tested for serum production of antibodies against H5N1 virus. The data from the serum antibody tests are contained in Table 1 and illustrated in FIG. 1.

FIG. 3 illustrates a double differentiation between the infectivity and the lethality of isolates of H1N1 isolated between 2004 and May 18, 2009. In FIG. 3, the black columns represent the mean annual Replikin Count for hemagglutinin protein area sequences (associated with infectivity) publicly available at www.pubmed.com for isolates of H1N1 influenza in a given year between 2004 and 2009. Standard deviation is denoted by the capped line on top of the black columns. The gray columns represent the mean annual Replikin Count for sequences from the pB1 gene area (associated with lethality) publicly available at www.pubmed.com for isolates of H1N1 influenza in a given year between 2004 and 2009. Standard deviation is denoted by the capped line on top of the gray columns. The data for FIG. 3 is disclosed in Table 4 in Example 3 below. FIG. 3 illustrates that Replikin Count for the hemagglutinin protein area is differentiable from Replikin Count for the pB1 gene area and that infectivity properties in H1N1 are differentiable from lethality properties in H1N1. The data in FIG. 3 corresponds to epidemiological data in H1N1. Infectivity in H1N1 has increased dramatically in 2009 resulting in a global outbreak of H1N1 influenza apparently beginning in or near Mexico or the southwestern United States around the spring of 2009. The increase in Replikin Count in the hemagglutinin protein area of isolates of H1N1 in the winter of 2008 allowed for an April 2008 prediction of the current global outbreak in 2009. Additionally, lethality in H1N1 has been observed to remain generally low between 2004 and 2009 with a spike in lethality in early 2009.

FIG. 4 illustrates a double differentiation between the infectivity and the lethality of isolates of H1N1 isolated between 2001 and Jun. 8, 2009. In FIG. 4, black columns represent the mean annual Replikin Count for hemagglutinin protein area sequences (associated with infectivity) of isolates of H1N1 influenza publicly available at www.pubmed.com for a given year between 2001 and 2009 (the 2009 column represents the mean annual Replikin Count for hemagglutinin protein area sequences of isolates of H1N1 influenza publicly available from Jan. 1, 2009 through Jun. 8, 2009). Standard deviation is denoted by the capped line on top of the black columns. Gray columns represent the mean annual Replikin Count for sequences from the pB1 gene area (associated with lethality) of isolates of H1N1 influenza publicly available at www.pubmed.com for a given year between 2001 and 2009 (the 2009 column represents the mean annual Replikin Count for the pB1 gene area sequences of isolates of H1N1 influenza publicly available from Jan. 1, 2009 through Jun. 8, 2009). Standard deviation is denoted by the capped line on top of the gray columns. The data for FIG. 4 is disclosed in Tables 5 and 6 in Example 4 below. FIG. 4 illustrates that Replikin Count for the hemagglutinin protein area is differentiable from Replikin Count for the pB1 gene area and that infectivity properties in H1N1 are differentiable from lethality properties in H1N1. The data in FIG. 4 corresponds to epidemiological data in H1N1. As described above, infectivity in H1N1 increased dramatically in 2009 resulting in an H1N1 pandemic. Additionally, lethality in H1N1 has been observed to remain generally low between 2004 and 2008 with a spike in lethality in 2009 based on data analyzed between May 18 and Jun. 8, 2009. The spike in lethality in 2009 is observed as statistically significant with a p-value of less than 0.001. See Table 6 in Example 4 below. An earlier rise in the Replikin Count in the pB1 gene area in 2005 is not statistically significant with a p-value of less than 0.40. See Table 6 below.

FIG. 5 illustrates a double differentiation between the infectivity and the lethality of isolates of H1N1 isolated between 2001 and Sep. 23, 2009. In FIG. 5, the white columns represent the mean annual Replikin Count for hemagglutinin protein area sequences (publicly available at www.pubmed.com) of isolates of H1N1 influenza isolated in a given year for years 2001 through 2007 and represent the mean Replikin Count from the beginning of a given year through to the given date for years 2008 and 2009. Standard deviation is denoted by a capped line on top of each white column. The hemagglutinin protein area is associated with infectivity in influenza. The black columns represent the mean annual Replikin Count for sequences from the pB1 gene area (publicly available at www.pubmed.com) of isolates of H1N1 influenza isolated in a given year for years 2001 through 2007 and represent the mean Replikin Count from the beginning of a given year through to the given date for years 2008 and 2009. Standard deviation is denoted by a capped line on top of each black column. The pB1 gene area of influenza is associated with lethality in influenza. The data for FIG. 5 is disclosed in Table 7 in Example 5 below. FIG. 5 illustrates that Replikin Count for the hemagglutinin protein area is differentiable from Replikin Count for the pB1 gene area and that infectivity properties in H1N1 are differentiable from lethality properties in H1N1. The data in FIG. 5 corresponds to epidemiological data. As described above, infectivity in H1N1 increased dramatically in 2009 resulting in a global outbreak of H1N1 influenza apparently beginning in or near Mexico or the southwestern United States around the spring of 2009. In further correspondence to FIG. 5, the lethality of the 2009 H1N1 outbreak has been fairly low with the proportion of deaths in the United States attributable to pneumonia and influenza below the epidemic threshold. See CDC FluView, Week 36 ending Sep. 12, 2009 available at http://www.cdc.gov/flu/weekly/. Further, the CDC has reported that pediatric mortality experienced a peak in June 2009, which was followed by a sharp drop in H1N1 pediatric mortality through September 2009. See id. All of this data corresponds to the Replikin Count data provided in FIG. 5.

DETAILED DESCRIPTION OF THE INVENTION

Definitions

A "protein fragment" as used in this specification is any portion of an expressed whole protein. A protein fragment may reflect an expressed whole protein with one or more amino acids removed from the amino acid sequence of the expressed whole protein. A protein fragment may also reflect an amino acid sequence that is at least 30%, 40%, 50%, 60%, 70%, 80%, 90%, 95%, or 100% homologous with any portion of an expressed whole protein. A "polypeptide," as used in this specification, is any portion of a protein fragment and is less than an expressed whole protein.

A "whole protein" or an "expressed whole protein" as used in this specification reflect a protein that is expressible from an intact gene of an influenza virus from a start codon to a stop codon. A whole protein or expressed whole protein may also reflect a whole protein or expressed whole protein that has been subject to cellular processing to create a protein that is capable of functioning within the virus replication system in a proper manner for virus replication. A protein fragment, polypeptide, or peptide "partially matches" the amino acid sequence of an expressed whole protein when the protein fragment, polypeptide, or peptide shares substantially homology with the expressed whole protein but at least one of the amino acids of the expressed whole protein are not present in the protein fragment, polypeptide, or peptide. "Homologous" or "homology" or "sequence identity" as used in this specification indicate an amino acid sequence or nucleic acid sequence exhibits substantial structural equivalence with another sequence, namely any one of SEQ ID NO(s): 1-66 (for purposes of this paragraph, the basis sequences) or any nucleotide sequence encoding SEQ ID NO(s): 1-66 (a redundancy in a coding sequence may be considered identical to a sequence encoding the same amino acid). To determine the percent identity or percent homology of an identified sequence, the sequence is aligned for optimal comparison purposes with any one of the basis sequences. Where gaps are necessary to provide optimal alignment, gaps may be introduced in the identified sequence or in the basis sequence. When a position in the identified sequence is occupied by the same amino acid residue or same nucleotide as the corresponding position in the basis sequence, the molecules are considered identical at that position (as used herein amino acid or nucleic acid "identity" is equivalent to amino acid or nucleic acid "homology"). To determine percent homology, the amino acid residues or nucleotides at corresponding amino acid positions or nucleotide positions are compared between the identified sequence and the basis sequence. The total number of amino acid residues or nucleotides in the identified sequence that are identical with amino acid residues or nucleotides in the basis sequence is divided by the total number of residues or nucleotides in the basis sequence (if the number of residues or nucleotides in the basis sequence is greater than the total number of residues or nucleotides in the identified sequence) or by the total number of amino acid residues or nucleotides in the identified sequence (if the number of residues or nucleotides in the identified sequence is greater than the total number of residues or nucleotides in the basis sequence). The final number is determined as a percentage. As such, the percent identity between the two sequences is a function of the number of identical positions shared by the sequences, taking into account the number of gaps (where a gap must be introduced for optimal alignment of the two sequences) and the length of each gap. Any structural or functional differences between sequences having sequence identity or homology will not affect the ability of the sequence to function as indicated in the desired application.

For example, SEQ ID NO: 1 (HAQDILEKEHNGKLCS-LKGVRPLILK) is considered more than 86% homologous with the following sequence HAQDILEKEHNGKLCSLKGVRPX$_{n=4}$LILK (SEQ ID NO: 29). The more than 86% homology between SEQ ID NO: 1 and SEQ ID NO: 29 is determined as follows: SEQ ID NO: 29 is the identified sequence. SEQ ID NO: 1 is the basis sequence. Upon alignment, SEQ ID NO: 29 is identical to SEQ ID NO: 1 in all 26 residues of SEQ ID NO: 1 (with a gap introduced for the four residues represented by $X_{n=4}$). To determine percent homology, then, the 26 aligned identical residues are divided by the total number of residues in SEQ ID NO: 29, namely 30 residues, giving 0.867 or more than 86% homology.

As another example, SEQ ID NO: 1 is more than 86% homologous with HAQDXILEKEHNGKLCXS-LKGVRXXPLILK (SEQ ID NO: 30) because it is identical to SEQ ID NO: 30 in all residues except for the residues represented by the four X residues.

In a further example, SEQ ID NO: 2 (KEHNGKLCS-LKGVRPLILK) is more than 68% homologous with KEH-NGKLCSLKGK (SEQ ID NO: 31). SEQ ID NO: 2 is the basis sequence and has 19 residues. SEQ ID NO: 31 is the reference sequence and has 13 residues that are identical to SEQ ID NO: 2 but VRPLIL is not present between the glycine at position 12 and the terminal lysine at position 13 (all of the other residues are identical). To determine percent homology, then, the 13 aligned identical residues are divided by the total number of residues in SEQ ID NO: 2, namely 19 residues, giving 0.684 or more than 68% homology.

To determine homology between an identified sequence that is contained in a larger polypeptide, protein fragment, or protein, and a basis sequence, the polypeptide, protein fragment, or protein must first be optimally aligned with the basis sequence. Upon alignment of the sequences, the residue in the identified sequence that is farthest to the amino-terminus of the polypeptide, protein fragment, or protein and identical to a residue in the basis sequence that is farthest to the amino-terminus of the basis sequence is considered the amino-terminal residue of the identified sequence. Likewise, upon alignment, the residue in the identified sequence that is farthest to the carboxy-terminus of the polypeptide, protein fragment, or protein and identical to a residue in the basis sequence that is farthest to the carboxy-terminus of the basis sequence is considered the carboxy-terminal residue of the identified sequence.

An amino acid sequence of a protein fragment, polypeptide, or peptide is "derived from" an identified protein or gene area of an influenza virus (such as a hemagglutinin protein area or a pB1 gene area) if one of ordinary skill in the art would understand from the structure, history, or other relevant information of the amino acid sequence that it originated from an amino acid sequence of the identified protein or gene area of influenza. Among other methods, one of ordinary skill may employ analysis of the homology of the amino acid sequence with the identified protein or gene area. One of ordinary skill may also employ the history of research used in developing the amino acid sequence to determine that the amino acid sequence is derived from an original sequence of the identified protein or gene area. One of ordinary skill would understand that a protein fragment, polypeptide, or peptide is derived from an identified protein, polypeptide, or peptide if it is traceable to the identified protein, polypeptide, or peptide, if it is deducible or inferable from the identified protein, polypeptide, or peptide, if the identified protein, polypeptide, or peptide is the source of the peptide, or if the protein fragment, polypeptide, or peptide is derived from the identified protein, polypeptide, or peptide as understood by one of skill in the art. One of ordinary skill may employ any method known now or hereafter for determining whether an amino acid sequence is derived from an identified protein or gene area of an influenza virus.

As used herein, "transmission" means, the movement of a pathogen by any means from one animal host to any neighboring animal host.

As used herein, "reservoir" means, a collection of animals, one or all of which are infected with a particular infectious agent, wherein the collection of animals continues to provide a source of infection outside of the collection of animals. A reservoir is self-perpetuating and permits time for modification of viruses within the reservoir and passing of viruses, including modified viruses, to hosts outside of the reservoir.

As used herein, "concomitant" or "concomitantly" or related words reflect a difference between the change in infectivity and the change in lethality in a strain of influenza or in different strains or isolates of influenza within a particular time period or at a particular time point or within a particular region. For example, if the relative infectivity of a first isolate from a given time period or time point or from a particular region is greater than the relative infectivity of a second isolate from the same time period or same time point or same particular region and the relative lethality of the first isolate is not greater than the relative lethality of the second isolate, then the lethality of the first isolate is not concomitantly greater than the relative lethality of the second isolate. Additionally, for example, an increase in the relative infectivity over time in a group of isolates from a particular time period or region that is not accompanied by, attended by, or does not correspond with an increase in the relative lethality over time in the same group of isolates is an increase in infectivity that is not concomitant with an increase in lethality in the same group of isolates. Changes in infectivity that are not concomitant with changes in lethality in a strain of influenza virus allow for the differentiation of the properties of infectivity and lethality in a strain of influenza over a particular time period or across different regions.

As used herein a "vaccine" is any substance, compound, composition, mixture, or other therapeutic substance that, when administered to a human or animal via any method of administration known to the skilled artisan now or hereafter, produces an immune response, an antibody response, or a protective effect in the human or animal.

A protein area or a gene area of an influenza protein or gene is the protein or gene of influenza as known to one of skill in the art. Because one skilled artisan may choose to identify a first terminus of a protein or gene in influenza at a different starting point than another skilled artisan and one skilled artisan may choose to identify a second terminus of a protein or gene in influenza at a different ending point than another skilled artisan based on research conditions, one of skill in the art understands that the hemagglutinin protein and the pB1 gene may be considered as a protein area or a gene area.

As used herein, a "Replikin sequence" is an amino acid sequence of 7 to about 50 amino acids comprising or consisting of a Replikin motif wherein the Replikin motif comprises:
(1) at least one lysine residue located at a first terminus of said peptide and at least one lysine residue or at least one histidine residue located at a second terminus of said peptide;
(2) a first lysine residue located six to ten residues from a second lysine residue;
(3) at least one histidine residue; and
(4) at least 6% lysine residues.

For the purpose of determining Replikin concentration, a Replikin sequence must have a lysine residue at one terminus and a lysine or a histidine residue at the other terminus. For diagnostic, therapeutic, and preventive purposes, a Replikin sequence may or may not have defined termini.

The term "Replikin sequence" can also refer to a nucleic acid sequence encoding an amino acid sequence having 7 to about 50 amino acids comprising:
(1) at least one lysine residue located six to ten amino acid residues from a second lysine residue;
(2) at least one histidine residue; and
(3) at least 6% lysine residues,
wherein the amino acid sequence may comprise a terminal lysine and may further comprise a terminal lysine or a terminal histidine.

As used herein, the term "peptide" or "protein" refers to a compound of two or more amino acids in which the carboxyl group of one amino acid is attached to an amino group of another amino acid via a peptide bond.

As used herein, an "isolated" peptide may be synthesized by organic chemical methods. An isolated peptide may also be synthesized by biosynthetic methods. An isolated peptide also may refer to a peptide that is, after purification, substantially free of cellular material or other contaminating proteins or peptides from the cell or tissue source from which the peptide is derived, or substantially free from chemical precursors or other chemicals when chemically synthesized by any method, or substantially free from contaminating peptides when synthesized by recombinant gene techniques or a protein or peptide that has been isolated in silico from nucleic acid or amino acid sequences that are available through public or private databases or sequence collections. An isolated peptide may be synthesized by biosynthetic or organic chemical methods.

Protein fragments, polypeptides, or peptides in this specification may be chemically synthesized by any method known to one of skill in the art now and hereafter. For example, isolated protein fragment, polypeptides, or peptides may be synthesized by solid phase synthesis. The production of these materials by chemical synthesis avoids the inclusion of (or the need to remove by purification) materials that are byproducts of other production methods such as recombinant expression or isolation from biological material. Such byproducts may include, for example, avian proteins associated with vaccines produced using birds' eggs or bacterial proteins associated with recombinant production in bacteria.

An "encoded" or "expressed" protein, protein sequence, protein fragment sequence, or peptide sequence is a sequence encoded by a nucleic acid sequence that encodes the amino acids of the protein or peptide sequence with any codon known to one of ordinary skill in the art now or hereafter. It should be noted that it is well-known in the art that, due to redundancy in the genetic code, individual nucleotides can be readily exchanged in a codon and still result in an identical amino acid sequence. As will be understood by one of ordinary skill in the art, a method of identifying a Replikin amino acid sequence also encompasses a method of identifying a nucleic acid sequence that encodes a Replikin amino acid sequence wherein the Replikin amino acid sequence is encoded by the identified nucleic acid sequence.

As used herein, "conserved" or "conservation" refers to conservation of particular amino acids due to lack of substitution. Conservation may occur at a specific position in a protein or polypeptide or may occur at a position that is close to a specific position in a protein or polypeptide but not the exact specific position. This type of conservation occurs because additional amino acid residues may be substituted in a protein or polypeptide such that the numbering of residue positions may shift toward either terminus of the protein or polypeptide.

As used herein, "Replikin Count" or "Replikin Concentration" refers to the number of Replikin sequences per 100 amino acids in a protein, protein fragment, virus, or organism. A higher Replikin concentration in a first strain of a virus or organism has been found to correlate with more rapid replication of the first virus or organism as compared to a second, earlier-arising or later-arising strain of the virus or organism having a lower Replikin concentration. Replikin concentration is determined by counting the number of Replikin sequences in a given sequence, wherein a Replikin sequence is a peptide of 7 to about 50 amino acid residues with a lysine residue on one end and a lysine residue or a histidine residue on the other end wherein the peptide comprises (1) a lysine residue six to ten residues from another lysine residue, (2) a histidine residue, (3) and 6% or more lysine residues, or wherein a Replikin sequence is a nucleic acid that encodes a Replikin peptide sequence.

Replikin Peptide Sequences Available for Therapies in Influenza Virus Across Strains and Over Time An aspect of the present invention provides compounds for diagnostic, therapeutic, and/or preventive purposes in influenza, methods of differentiating infectivity and lethality in influenza, and methods of designing therapies against influenza based on compounds of the invention and differentiation of infectivity and lethality in influenza.

Compounds of the invention include Replikin peptides and homologues of Replikin peptides identified in and isolated from different strains of influenza and conserved over time in the same and different strains of influenza. These Replikin peptides have been shown to be useful when comprised in immunogenic compounds and have provided a protective effect against influenza infection including antagonism of both the infectivity of strains of influenza and the replication and lethality of strains of influenza. Because these Replikin peptides are conserved within strains of influenza over time and across different strains of influenza at conserved positions in the different strains of influenza, the ordinary skilled artisan expects the functionality of these peptides to share commonality among various strains of influenza and among various isolates of the same strain of influenza at different times.

Twelve peptides provided in an aspect of this invention were first identified as conserved in low-pathogenic H5N1 and high-pathogenic H5N1 and were combined in a successful vaccine in chickens where infectivity, replication, and excretion of low-pathogenic H5N1 were all antagonized or blocked by the vaccine. An exact homologue of one of the twelve peptides was later identified as conserved at position 184 in isolates of H1N1, high-pathogenic H5N1, and H9N2. See SEQ ID NO(s): 8 and 19. Further homologues were then identified in other isolates of H1N1 and H5N1. See SEQ ID NO(s): 13 and 20. Each of the homologues was positioned in the pB1 gene area of the virus. Based on the data presented herein concerning the function of the pB1 gene area in lethality in various influenza viruses over time and the commonality and conservation of the homologues, the applicants recognized that any of the homologues would be useful as an immunogenic compound against any of the strains of influenza virus in which a homologue had been or would be identified. As a result, the applicants have developed methods of identifying other homologues of the twelve peptides contained in the successful vaccine against low-pathogenic H5N1. These homologues are now available for use in an immunogenic compounds that may be used against any strain of influenza virus in which a homologue of one of the twelve peptides is identified. They are further available against strains of influenza virus where the homologues are present in the hemagglutinin or pB1 gene areas. In one aspect of the invention, a homologue may be 30%, 40%, 50%, 60%, 70%, 80%, 90%, 95%, or more or 100% homologous with a peptide against which the homologue is compared. The methods have provided peptides for a vaccine that may be applied for prevention or treatment of any strain of influenza virus. The vaccine is known as TransFlu™.

The applicants have now additionally developed another vaccine that comprises eight additional peptides identified in the hemagglutinin protein area and pB1 gene area of the H1N1 virus. Homologues of any one of these eight peptides may also be used in an immunogenic compound against any strain of influenza virus that contains a homologue of one of the eight peptides. A homologue of one these eight peptides may likewise be 30%, 40%, 50%, 60%, 70%, 80%, 90%, 95%, or more or 100% homologous with a peptide against which the homologue is compared.

Because the peptides disclosed in the vaccines herein described are peptides that are conserved over time in specific strains and shared between strains (also over time), one of skill in the art expects such peptides (and peptides that are similar in structure and function) to also be useful in immunogenic compounds for influenza infections of various strains. This expectation is based on, for example, the function of the peptides identified herein and the commonality of structure and position of the peptides and their homologues as described herein as well as the functionality of the peptides and the homologues in the hemagglutinin protein area and pB1 gene area in different strains of influenza. See, e.g., FIGS. 2-5. This expectation is also based in part on the conservation of Replikin peptides generally and the commonality of function of Replikin peptides across strains of influenza and across different viruses and organisms. See, e.g., Tables 7a, 8, 9, and 10 with descriptions and Examples 6 and 7 in U.S. application Ser. No. 11/355,120, filed Feb. 16, 2006 and Table 8 with description in U.S. Pat. No. 7,442,761, and FIGS. 1-21 in U.S. application Ser. No. 12/010,027, filed Jan. 18, 2008. For example, Replikin peptides have been shown to be broadly antigenic, to be conserved, and to be related to rapid replication and outbreaks across many different strains of influenza virus. See, e.g., U.S. application Ser. No. 11/355, 120, filed Feb. 16, 2006. Additionally, the crucial lysine and histidine residues of Replikin peptides have been demonstrated to be related to rapid replication and to be conserved in fixed positions within functional proteins even in highly mutable viruses such as HIV. See, e.g., Table 8 with description in columns 62 and 63 in U.S. Pat. No. 7,442,761. Further, as described herein the Replikin peptides and homologues disclosed herein are shown to be structurally and functionally related to the infectivity and lethality of influenza virus based on the positions in the hemagglutinin protein area or pB1 gene area of influenza, respectively. As a result, the peptides and their homologues described herein are, among other things, antigenic, common to various strains of influenza virus in both position and function, conserved in various strains of influenza over time, conserved in specific positions in the hemagglutinin protein area and pB1 gene areas over time, conserved in their lysines and histidines within the Replikin structure, and associated with mechanisms of infectivity and/or lethality. As a result, one of ordinary skill in the art would expect the Replikin peptides and their homologues described herein to be useful in immunogenic compounds for therapies against influenza virus within strains, across strains, and across time.

Shared and Conserved Replikin Peptide Sequences and their Homologues

Replikins sequences and their homologues provided by an aspect of the invention may be identified in strains of influenza virus including any strain of influenza virus known now or identified or known hereafter. Compounds of the invention may be conserved within strains of influenza virus, across types within strains of influenza virus, and across strains of influenza virus. The compounds, because they are Replikin sequences, related to Replikin sequences, derived from Replikin sequences, identified as comprising Replikin sequences, or designed to comprise Replikin sequences, are related to rapid replication, virulence, and lethality in influenza. See FIGS. 2-5. Compounds of the invention, including conserved Replikin peptides, are useful as immunogenic compounds to stimulate the immune system of a subject to produce an immune response, which may include production of antibodies or other binding molecules. Compounds of the invention are also useful in therapies such as vaccines. Compounds of the invention are likewise useful in producing antibodies, antibody fragments, or other binding or antagonizing agents, which may be used, among other things, for diagnostic and therapeutic purposes, including passive immunity.

The immunogenic compounds, antibodies (and other binding or antagonizing agents) and vaccines of the invention are useful against any strain of influenza virus including influenza A, B, or C strains. Within strains of influenza A, they are useful against any strain of influenza A including, but not limited to, H1N1, H1N2, H2N2, H3N2, H3N8, H5N1, H5N2, H7N7, H7N2, H7N3, H9N2, and H10N7. They are useful in any organism that is capable of producing an immune response. The compounds of the invention are also useful for diagnostic purposes, including identifying rapidly replicating, virulent, or lethal strains of virus.

The compounds of the invention may be conserved in the H5N1 strain of virus including low-pathogenic (Low-Path) strains of H5N1 and high-pathogenic (High-Path) strains of H5N1. The compounds may also be conserved in other strains of influenza including H1N1, H1N2, H2N2, H3N2, H3N8, H5N1, H5N2, H7N7, H7N2, H7N3, H9N2, and H10N7. For example, the following twenty-eight peptides and homologues of the following twenty-eight peptides are provided as an aspect of the invention as isolated or synthesized peptides, as immunogenic compounds, as vaccines, and as targets for antibodies and binding agents of the invention, among other things: HAQDILEKEHNGKLCSLKGVRPLILK (SEQ ID NO:1), KEHNGKLCSLKGVRPLILK (SEQ ID NO: 2), KKNNAYPTIKRTYNNTNVEDLLIIWGIHH (SEQ ID NO: 3), HHSNEQGSGYAADKESTQKAIDGITNK (SEQ ID NO: 4), HDSNVKNLYDKVRLQLRDNAK (SEQ ID NO: 5), KVRLQLRDNAKELGNGCFEFYH (SEQ ID NO: 6), KDVMESMDKEEMEITTH (SEQ ID NO: 7), HFQRKRRVRDNMTKK (SEQ ID NO: 8), KKWSH-KRTIGKKKQRLNK (SEQ ID NO: 9), HKRTIGKKKQRLNK (SEQ ID NO: 10), HEGIQAGVDRFYRTCKLVGINMSKKK (SEQ ID NO: 11), HSWIPKRNRSILNTSQRGILED-EQMYQKCCNLFEK (SEQ ID NO: 12), HFQRKRRVRD-NVTK (SEQ ID NO: 13), HCQKTMNQVVMPK (SEQ ID NO: 14), HYQKTMNQVVMPK (SEQ ID NO: 15), KRWR-LFSKH (SEQ ID NO: 16), KKKHKLDK (SEQ ID NO: 17), KKKQRLTKX$_n$H (SEQ ID NO: 18) (where n=any amino acid from 1 to 41 residues), HFQRKRRVRDNMTK (SEQ ID NO: 19), HFQRKRRVRDNMTKKMVTQR-TIGKKKQRLNK (SEQ ID NO: 20), KKGSSYPKL-SKSYVNNKGKEVLVLWGVHH (SEQ ID NO: 21), HPVTIGECPKYVRSTK (SEQ ID NO: 22), KFEIFPKTSS-WPNH (SEQ ID NO: 23), HNGKLCKLKGIAPLQLGK (SEQ ID NO: 24), KSYVNNKGKEVLVLWGVHH (SEQ ID NO: 25), KMNTQFTAVGKEFNH (SEQ ID NO: 26), KSQLKNNAKEIGNGCFEFYH (SEQ ID NO: 27), KHSNGTVK (SEQ ID NO: 28).

SEQ ID NO(s): 1-12, 13-20, 21-28, and 32-66 are sequences that were initially identified in H1N1 or H5N1 as related to infectivity or lethality in those strains of influenza virus. Further investigation of the conservation of certain of those sequences in other strains of influenza virus provided identical sequences or homologues of those sequences conserved in other strains of influenza virus including H9N2, H3N2, H5N1, and H1N1 where the conserved homologues shared the same amino acid residue position in the functional protein of the other strain of influenza virus. As a result, the conserved homologues would be expected to share the same functional characteristics in those other influenza viruses where they are conserved.

The conserved homologues are further identified in positions in the hemagglutinin protein area and pB1 gene areas of various strains of influenza where these genes are directly associated with infectivity and lethality, respectively. Further, a vaccine based on these homologues has provided successful results in chickens in antagonizing both the infectivity of influenza virus and the replication (or lethality) of influenza virus once it has entered a host system. See, e.g., Example 1 below.

Information on the conservation of homologous sequences across various strains of influenza virus, therefore, provides sequences that offer immunogenic compounds for antagonism of all strains comprising these homologues. As a result, a vaccine is provided herein (known as TransFlu™) that offers cross-strain protection for a variety of strains of influenza.

For example, SEQ ID NO(s): 1-12 were initially identified in a strain of Low-Path H5N1. These peptides have since that time been identified in a series of highly pathogenic (High-Path) strains of H5N1 influenza, including a lethal strain of H5N1 isolated in Vietnam, among others. These peptides have been shown to provide a protective effect against infectivity and replication in host systems. SEQ ID NO(s): 13-20 have now also been identified and isolated as homologues of at least one amino acid sequence of SEQ ID NO(s): 1-12. Certain of these homologues have been identified not only in strains of H5N1 but also in other strains of influenza virus such as H5N2, H3N2, and H1N1. Additionally, SEQ ID NO(s): 21-28 are also provided as a vaccine against H1N1. Homologues of these sequences in other strains of influenza are expected to provide cross-strain protection.

Replikin peptides in general are seen to be conserved across strains of influenza. In particular, amino acid residues that provide for the Replikin sequence structure of the peptides of SEQ ID NO(s): 1-12, 13-20, 21-28, and 32-66 is conserved widely across strains and time in influenza. The key amino acid residues that provide for the Replikin sequence structure are the lysine and histidine residues wherein a Replikin sequence has at least one lysine on one terminus and at least one lysine or one histidine on the other terminus, at least one lysine that is six to ten residues from at least one other lysine, at least one histidine, and at least six percent lysines in total between the terminal lysine and the terminal lysine or histidine. Homologues of the Replikin peptides of SEQ ID NO(s): 1-12, 13-20, 21-28, and 32-66 (where the lysines and histidines that create the Replikin structure are conserved) have been seen to be conserved widely across strains of influenza virus.

As may be seen in FIG. 21 of U.S. application Ser. No. 11/355,120, filed Feb. 16, 2006, when conserved homologues Replikin sequences are aligned one on top of the other over time, it is most apparent that fixed and conserved portions of the structure of Replikin sequences align in a series of posts or girders that illustrate, like the structure of a building, how key conserved amino acids provide constancy for the survival of influenza over time as it mutates to avoid immune recognition in its prospective host but maintains key functional genetic structures that provide for continued replication of the virus. These key functional genetic structures provide targets that Replikin-based therapies antagonize.

Compounds and Compositions Comprising Peptides Homologous to Influenza Replikin Peptides One aspect of the present invention provides a protein, a protein fragment, a polypeptide, or a peptide that comprises at least one peptide A homologous with at least one peptide of SEQ ID NO(s): 1-12, 13-20, 21-28, and 32-66. Peptide A may be 30%, 40%, 50%, 60%, 70%, 80%, 90%, or 95% or more homologous or 100% homologous with any of the peptides of SEQ ID NO(s): 1-12, 13-20, 21-28, and 32-66. The protein, protein fragment, or peptide may likewise be a peptide that consists of a peptide A that is homologous with any of SEQ ID NO(s): 1-12, 13-20, 21-28, and 32-66. A peptide consisting of any one of SEQ ID NO(s): 1-12, 13-20, 21-28, and 32-66 is also provided.

The amino acid sequence of the provided isolated or synthesized protein, protein fragment, polypeptide, or peptide may partially match an amino acid sequence of an expressed whole protein. At least one, five, ten, twenty, thirty, forty, fifty, one hundred, two hundred, three hundred, four hundred, five hundred, five hundred and fifty or more amino acid residues of the amino acid sequence of the expressed whole protein may not be present in the protein, protein fragment, polypeptide, or peptide. The amino acid sequence of the isolated or synthesized protein, protein fragment, polypeptide, or peptide may also partially match the amino acid sequence of an expressed whole protein where at least one, ten, twenty, thirty, forty, fifty, sixty, seventy, eighty, ninety, one hundred, one hundred fifty, two hundred, two hundred fifty, three hundred, three hundred fifty, four hundred, four hundred fifty, five hundred, five hundred fifty or more amino acid residues of at least one terminus of the amino acid sequence of the expressed whole protein is(are) not present at least one terminus of said protein fragment, polypeptide, or peptide. Any additional number of amino acids may be situated on one or the other terminus or on both termini of the protein, protein fragment, polypeptide, or peptide.

Because a Replikin peptide, such as SEQ ID NO(s): 1-12, 13-20, 21-28, and 32-66, is associated with rapid replication, infectivity, and/or lethality, in functional proteins in influenza viruses, inclusion of any Replikin peptide in a protein, protein fragment, polypeptide, or peptide does not negate the functional nature of the Replikin peptide. As such, antagonism of at least one of SEQ ID NO(s): 1-12, 13-20, 21-28, and 32-66 or a homologue of SEQ ID NO(s): 1-12, 13-20, 21-28, and 32-66 (with homology of 30% or greater) within a protein, protein fragment, polypeptide, or peptide would be expected to antagonize the replication, infectivity, and/or lethality of the protein, protein fragment, polypeptide, or peptide.

A provided peptide may further be a peptide B of 7 to about 50 amino acid residues where peptide B contains a peptide A that is 30%, 40%, 50%, 60%, 70%, 80%, 90%, or 95% or more homologous or 100% homologous with any one of SEQ ID NO(s): 1-12, 13-20, 21-28, and 32-66. A non-limiting peptide may further be a peptide A that is a Replikin peptide wherein the Replikin peptide has a lysine residue on one end and a lysine residue or a histidine residue on the other end wherein the Replikin peptide comprises: (1) a lysine residue six to ten amino acids from another lysine residue; (2) at least one histidine residue; and (3) at least 6% lysine residues.

An isolated or synthesized protein, protein fragment, polypeptide, or peptide may consist of a peptide that is 30%, 40%, 50%, 60%, 70%, 80%, 90%, 95%, or 100% homologous with at least one of SEQ ID NO(s): 1-12, 13-20, 21-28, and 32-66 where the length of the peptide is no more than one, five, ten, twenty, thirty, forty, or fifty amino acid residues longer than the sequence of SEQ ID NO(s): 1-12, 13-20, 21-28, and 32-66 with which it is homologous. An isolated or synthesized protein fragment, polypeptide, or peptide may likewise be no more than one, two, three, four, five, six, seven, eight, nine, or ten amino acid residues longer than the sequence of SEQ ID NO(s): 1-12, 13-20, 21-28, and 32-66 with which it is homologous. An isolated or synthesized protein fragment, polypeptide, or peptide may likewise consist of any one of the peptides of SEQ ID NO(s): 1-12, 13-20, 21-28, and 32-66.

An isolated or synthesized polypeptide or peptide may comprise a peptide A that has about the same number of amino acid residues as a peptide B, where peptide B is one of the peptides of SEQ ID NO: 1-28 and where the lysine residues and histidine residues in peptide A are conserved as compared to the lysine residues and histidine residues in peptide B. An isolated or synthesized polypeptide or peptide comprising peptide A may have up to 100 additional amino acid residues as compared to peptide B. Some or all of the up to 100 additional amino acid residues may be positioned toward the amino-terminus and/or carboxy-terminus of the lysine or histidine termini of peptide A. Some of the additional amino acid residues may be positioned within the lysine or histidine termini of peptide A so long as a level of homology is maintained between peptide A and peptide B that retains at least some of the functionality of the Replikin peptide of peptide B. Functionality may include, but is not limited to, antigenicity, rate of replication, antagonizability of a protein containing said peptide A or said peptide B, binding capacity of binding agents to peptides A or B, etc.

An isolated or synthesized polypeptide or peptide may also comprise up to about 90, about 80, about 70, about 60, about 50, about 40, about 30, about 20, about 10, about 5, about 4, about 3, about 2, or about 1 additional amino acid residues. The residues may be entirely outside of the Replikin structure or entirely within the Replikin structure or partially within and partially outside the Replikin structure. A level of homology should be maintained between peptides B and A when additional residues are present or are added. Residues outside of the Replikin structure are those residues on the amino-terminus or carboxy-terminus of the polypeptide or peptide as compared to the lysine or histidine termini of peptide A. Residues within the Replikin structure are those residues that are between the lysine or histidine termini of peptide A. An isolated or synthesized polypeptide or peptide may also consist of peptide A and peptide A may consist of peptide B.

An isolated or synthesized peptide may consist of a peptide of about 26 amino acid residues with a histidine residue within zero, one, two, three, four, or five residues of the amino-terminus of the peptide wherein the histidine residue is considered to reside at position 1, and wherein relative to position 1 there is a lysine residue at position 8, a histidine residue at position 10, a lysine residue at position 13, a lysine residue at position 18, and a lysine residue at position 26, and wherein up to one, two, three, four, or five additional residues may be present on the carboxy-terminus of the peptide after the lysine residue at position 26. If five residues are present on the amino-terminus of position 1 and five residues are present on the carboxy-terminus of position 26, the isolated or synthesized peptide will consist of about 36 amino acids. Such an isolated or synthesized peptide is a homologue of SEQ ID NO: 1 and may be used as an immunogenic compound or as a component of a vaccine against infectivity in any strain of influenza virus.

An isolated or synthesized peptide may consist of about 19 amino acid residues with a lysine residue within zero, one, two, three, four, or five residues of the amino-terminus of the peptide wherein the lysine residue is considered to reside at position 1, and wherein relative to position 1 there is a histidine residue at position 3, a lysine residue at position 6, a lysine residue at position 11, and a lysine residue at position 19, and wherein up to one, two, three, four, or five additional residues may be present on the carboxy-terminus of the peptide after the lysine residue at position 19. If five residues are present on each end of the peptide, it will consist of about 29 amino acids. Such an isolated or synthesized peptide is a homologue of SEQ ID NO: 2 and may be used as an immunogenic compound or as a component of a vaccine against infectivity in any strain of influenza virus.

An isolated or synthesized peptide may consist of about 29 amino acids residues with a lysine residue within zero, one, two, three, four, or five residues of the amino-terminus of the peptide wherein the lysine residue is considered to reside at position 1, and wherein relative to position 1 there is a lysine residue at position 2, a lysine residue at position 10, a histidine residue at position 28, and a histidine residue at position 29, and wherein up to one, two, three, four, or five additional residues may be present on the carboxy-terminus of the peptide after the histidine residue at position 29. If five residues are present on each end of the peptide, it will consist of about 39 amino acids. Such an isolated or synthesized peptide is a homologue of SEQ ID NO: 3 and may be used as an immunogenic compound or as a component of a vaccine against infectivity in any strain of influenza virus.

An isolated or synthesized peptide may consist of about 27 amino acid residues with a histidine residue within zero, one, two, three, four, or five residues of the amino-terminus of the peptide wherein the histidine residue is considered to reside at position 1, and wherein relative to position 1 there is a histidine residue at position 2, a lysine residue at position 14, a lysine residue at position 19, and a lysine residue at position 27, and wherein up to one, two, three, four, or five additional residues may be present on the carboxy-terminus of the peptide after the lysine residue at position 27. If five residues are present on each end of the peptide, it will consist of about 37 amino acids. Such an isolated or synthesized peptide is a homologue of SEQ ID NO: 4 and may be used as an immunogenic compound or as a component of a vaccine against infectivity in any strain of influenza virus.

An isolated or synthesized peptide may consist of about 21 amino acid residues with a histidine residue within zero, one, two, three, four, or five residues of the amino-terminus of the peptide wherein the histidine residue is considered to reside at position 1 and wherein relative to position 1 there is a lysine residue at position 6, a lysine residue at position 11, and a lysine residue at position 21, and wherein up to one, two, three, four, or five additional residues may be present on the carboxy-terminus of the peptide after the lysine residue at position 21. If five residues are present on each end of the peptide, it will consist of about 31 amino acids. Such an isolated or synthesized peptide is a homologue of SEQ ID NO: 5 and may be used as an immunogenic compound or as a component of a vaccine against infectivity in any strain of influenza virus.

An isolated or synthesized peptide may consist of about 22 amino acid residues with a lysine residue within zero, one, two, three, four, or five residues of the amino-terminus of the peptide wherein the lysine residue is considered to reside at position 1, and wherein relative to position 1 there is a lysine residue at position 11, and a histidine residue at position 22, and wherein up to one, two, three, four, or five additional residues may be present on the carboxy-terminus of the peptide after the histidine residue at position 22. If five residues are present on each end of the peptide, it will consist of about 32 amino acids. Such an isolated or synthesized peptide is a homologue of SEQ ID NO: 6 and may be used as an immunogenic compound or as a component of a vaccine against infectivity in any strain of influenza virus.

An isolated or synthesized peptide may consist of about 17 amino acids with a lysine residue within zero, one, two, three, four, or five residues of the amino-terminus of the peptide wherein the lysine residue is considered to reside at position 1, and wherein relative to position 1 there is a lysine residue at position 9, and a histidine residue at position 17, and wherein up to one, two, three four, or five additional residues may be present on the carboxy-terminus of the peptide after the histidine residue at position 17. If five residues are present on each end of the peptide, it will consist of about 27 amino acids. Such an isolated or synthesized peptide is a homologue of SEQ ID NO: 7 and may be used as an immunogenic compound or as a component of a vaccine against lethality in any strain of influenza virus.

An isolated or synthesized peptide may consist of about 15 amino acid residues with a histidine residue within zero, one, two, three, four, or five residues of the amino-terminus of the peptide wherein the histidine residue is considered to reside at position 1, and wherein relative to position 1 there is a lysine residue at position 5, a lysine residue at position 14, and a lysine residue at position 15, and wherein up to one, two, three, four, or five additional residues may be present on the carboxy-terminus of the peptide after the lysine residue at position 15. If five residues are present on each end of the peptide, it will consist of about 25 amino acids. Such an isolated or synthesized peptide is a homologue of SEQ ID NO: 8 and may be used as an immunogenic compound or as a component of a vaccine against lethality in any strain of influenza virus.

An isolated or synthesized peptide may consist of about 18 amino acid residues with a lysine residue within zero, one, two, three, four, or five residues of the amino-terminus of the peptide wherein the lysine residue is considered to reside at position 1, and wherein relative to position 1 there is a lysine residue at position 2, a histidine residue at position 5, a lysine residue at position 6, a lysine residue at positions 11, 12, and 13, and a lysine residue at position 18, and wherein up to one, two, three, four, or five additional residues may be present on the carboxy-terminus of the peptide after the lysine residue at position 18. If five residues are present on each end of the peptide, it will consist of about 28 amino acids. Such an isolated or synthesized peptide is a homologue of SEQ ID NO: 9 and may be used as an immunogenic compound or as a component of a vaccine against lethality in any strain of influenza virus.

An isolated or synthesized peptide may consist of about 14 amino acid residues with a histidine residue within zero, one, two, three, four, or five residues of the amino-terminus of the peptide wherein the histidine residue is considered to reside at position 1, and wherein relative to position 1 there is a lysine residue at position 2, a lysine residue at positions 7, 8, and 9, and a lysine residue at position 14, and wherein up to one, two, three, four, or five additional residues may be present on the carboxy-terminus of the peptide after the lysine residue at position 14. If five residues are present on each end of the peptide, it will consist of about 24 amino acids. Such an isolated or synthesized peptide is a homologue of SEQ ID NO: 10 and may be used as an immunogenic compound or as a component of a vaccine against lethality in any strain of influenza virus.

An isolated or synthesized peptide may consist of about 26 amino acid residues with a histidine residue within zero, one, two, three, four, or five residues of the amino-terminus of the peptide wherein the histidine residue is considered to reside at position 1, and wherein relative to position 1 there is a lysine residue at position 16, and a lysine residue at positions 24, 25, and 26, and wherein up to one, two, three, four, or five additional residues may be present on the carboxy-terminus of the peptide after the lysine residue at position 26. If five residues are present on each end of the peptide, it will consist of about 36 amino acids. Such an isolated or synthesized peptide is a homologue of SEQ ID NO: 11 and may be used as an immunogenic compound or as a component of a vaccine against lethality in any strain of influenza virus.

An isolated or synthesized peptide may consist of about 35 amino acid residues with a histidine residue within zero, one, two, three, four, or five residues of the amino terminus of the peptide wherein the histidine residue is considered to reside at position 1, and wherein relative to position 1 there is a lysine residue at position 6, a lysine residue at position 28, and a lysine residue at position 35, and wherein up to one, two, three, four, or five additional residues may be present on the carboxy-terminus of the peptide after the lysine residue at position 35. If five residues are present on each end of the peptide, it will consist of about 45 amino acids. Such an isolated or synthesized peptide is a homologue of SEQ ID NO: 12 and may be used as an immunogenic compound or as a component of a vaccine against lethality in any strain of influenza virus.

Any one of the above-listed isolated or synthesized peptides may have an amino-terminus at position 1 and a carboxy-terminus at the amino acid residue for which a position is expressly numbered where that expressly-numbered position is the farthest numbered position toward the carboxy-terminus of the peptide. For example, a homologue of SEQ ID NO: 7 (KDVMESMDKEEMEITTH) will have a terminal lysine at position 1 and a terminal histidine at position 17 or a homologue of SEQ ID NO: 4 (HHSNEQGSGYAAD-KESTQKAIDGITNK) will have a terminal histidine at position number 1 and a terminal lysine at position number 27.

The at least one isolated or synthesized protein, protein fragment, or peptide may also comprise at least one peptide A and at least one peptide C where peptide A is at least 30%, 40%, 50%, 60%, 70%, 80%, 90%, 95%, or 100% homologous with at least one peptide of SEQ ID NO(s): 1-12, 13-20, 21-28, and 32-66 and where peptide C is at least 30%, 40%, 50%, 60%, 70%, 80%, 90%, 95%, or 100% homologous with at least one peptide of SEQ ID NO(s): 1-12, 13-20, 21-28, and 32-66. Peptide C may be homologous with a different peptide from among SEQ ID NO(s): 1-12, 13-20, 21-28, and 32-66 than the peptide that peptide A is homologous with. The at least one isolated or synthesized protein, protein fragment, or peptide may comprise three or more peptides homologous with at least three different peptides of SEQ ID NO(s): 1-12, 13-20, 21-28, and 32-66.

All of the above-discussed proteins, protein fragments, polypeptides, and peptides comprise the functional unit of a homologue of SEQ ID NO(s): 1-12, 13-20, 21-28, and 32-66. These proteins, protein fragments, polypeptides, and peptides share a functional role in either infectivity or lethality. Antagonism of any of the homologues of SEQ ID NO(s): 1-12, 13-20, 21-28, and 32-66 will likewise antagonize either the infectivity function or lethality function in any strain of influenza that share a homologue of any one of the sequences. As a result, the proteins, protein fragments, polypeptides, and peptides are useful as immunogenic compounds, therapeutic compounds, vaccines, and for other therapies directed at antagonizing the infectivity and/or lethality of a strain of influenza. When comprised in a vaccine, disclosed proteins, protein fragments, polypeptides, and peptides are expected to be capable of limiting the excretion or shedding of influenza virus such that the virus is limited in its spread from host to host or from host to reservoir to host, etc. As such, disclosed compounds are effective at limiting sources of influenza infection. Likewise, any binding agent that binds one of the proteins, protein fragments, polypeptides, and peptides discussed above will antagonize the infectivity and/or lethality of a strain of influenza and limit sources of influenza infection such as transmission from host to host or from host to reservoir to host.

Immunogenic Compositions Comprising Peptide Homologous to Influenza Replikin Peptides As such, a non-limited protein, protein fragment, or peptide of the invention may be comprised in an immunogenic compound. The proteins, protein fragment, polypeptides, and peptides provided by an aspect of the invention comprise at least a portion that is homologous with a Replikin peptide of SEQ ID NO(s): 1-12, 13-20, 21-28, and 32-66. These homologues are expected by one of ordinary skill in the art to stimulate the immune system of a subject upon sufficient exposure to produce antibodies against at least the homologous portion of the protein, protein fragment, polypeptide, or peptide. One of ordinary skill in the art would expect that antibodies or other binding agents arrayed against a protein or protein fragment comprising one of the antigenic homologues disclosed herein would be antagonized.

One of ordinary skill would also expect an antagonist of one of these homologues to antagonize any influenza virus that comprises a homologue within its hemagglutinin protein area or pB1 gene area since an immune response against SEQ ID NO(s): 1-12 has been shown to antagonize both the infectivity and replication (including excretion) of H5N1. Because homologues of SEQ ID NO(s): 1-12 have been shown to be conserved across strains of influenza in the hemagglutinin protein area and the pB1 gene area, one of ordinary skill would expect antagonism of such homologues to result in antagonism of influenza replication similar to what was observed in SEQ ID NO(s): 1-12 in chickens. One of ordinary skill would further expect particular antagonism of the infectivity and lethality mechanisms of influenza when an immune system is stimulated against a homologue of SEQ ID NO(s): 1-6 and SEQ ID NO(s): 7-12, respectively.

As a result, the applicants disclose herein a series of homologues of SEQ ID NO(s): 1-12 identified in the hemagglutinin and pB1 gene areas of a wide range of strains of influenza. Each of these homologues is provided as a component that may be used in an immunogenic compound to stimulate the immune system of a subject against influenza infection. Additionally, other homologous sequences are likewise provided as immunogenic compounds to stimulate the immune system of a subject against influenza infection. Any homologue that shares 30%, 40%, 50%, 60%, 70%, 80%, 90%, 95% or more homology with any one of SEQ ID NO(s): 1-12 is disclosed as a peptide that may be used in an immunogenic compound against influenza infection. Additionally, any protein, protein fragment, polypeptide, or peptide comprising such a homologue may be used as an immunogenic compound or be comprised within an immunogenic compound. An immune response against such compounds would be understood by one of ordinary skill in the art to be useful in stimulating the immune system against an influenza infection.

Likewise, any homologue that shares 30%, 40%, 50%, 60%, 70%, 80%, 90%, 95% or more homology with any one of SEQ ID NO(s): 21-28 is disclosed as a peptide that may be used in an immunogenic compound against influenza infection. Any protein, protein fragment, polypeptide, or peptide comprising such a homologue may also be used as an immunogenic compound or may be comprised within an immunogenic compound. An immune response against such compounds would be understood by one of ordinary skill in the art to be useful in stimulating the immune system against an influenza infection.

Vaccines Comprising Peptides Homologous to Influenza Replikin Peptides

An immunogenic compound provided as an aspect of the invention may be used as a component of a non-limiting vaccine against any strain of influenza. A vaccine comprising one or more homologues of SEQ ID NO(s): 1-12, 13-20, 21-28, and 32-66 may be used against influenza infection. Likewise, a vaccine comprising one or more homologues of SEQ ID NO(s): 1-12, 13-20, 21-28, and 32-66 derived from a hemagglutinin protein area and one or more homologues of SEQ ID NO(s): 1-12, 13-20, 21-28, and 32-66 derived from a pB1 gene area may be used against influenza infection and may antagonize the infectivity and/or replication and lethality of an influenza infection. Further, mixtures of homologues of SEQ ID NO(s): 1-6 and SEQ ID NO(s): 7-12 are provided as vaccines to antagonize both the infectivity and replication and lethality of an influenza infection. Such vaccines are useful for antagonizing infectivity, replication, lethality, and excretion or spread of influenza virus.

A non-limiting vaccine is provided comprising: at least one protein fragment, polypeptide, or peptide comprising at least one peptide A, where peptide A is at least 30%, 40%, 50%, 60%, 70%, 80%, 90% or 95%, or 100%, homologous with at least one of SEQ ID NO(s): 1-12, 13-20, 21-28, and 32-66 and wherein peptide A is isolated from a hemagglutinin protein area of influenza virus, or a synthesized version thereof; and at least one protein fragment, polypeptide, or peptide comprising at least one peptide B, where peptide B is at least 30%, 40%, 50%, 60%, 70%, 80%, 90% or 95%, or 100%, homologous with at least one of SEQ ID NO(s): 1-12, 13-20, 21-28, and 32-66 and wherein peptide B is isolated from a protein or peptide encoded by a pB1 gene area of influenza virus, or a synthesized version thereof. The peptide A may be identified in, isolated from, derived from, or synthesized from an isolate of influenza virus predicted to have a greater infectivity than at least one other isolate of influenza virus and the peptide B may be identified in, isolated from, derived from, or synthesized from an isolate of influenza virus predicted to have a greater lethality than at least one other isolate of influenza virus. A vaccine may further comprise a plurality of protein fragments, polypeptides, and/or peptides from the hemagglutinin protein area and a plurality of protein fragments, polypeptides, and/or peptides from the pB1 gene area.

A vaccine may further comprise at least one Replikin peptide from the hemagglutinin protein area and at least one Replikin peptide from the pB1 gene area. A vaccine may further comprise a plurality of Replikin peptides from a hemagglutinin protein area where the at least one Replikin peptide from a pB1 gene area is a plurality of Replikin peptides from a pB1 gene area. A vaccine may comprise a plurality of the shortest Replikin peptides from a hemagglutinin protein area and a plurality of the shortest Replikin peptides from a pB1 area. A vaccine may comprise the shortest Replikin peptides from a hemagglutinin protein area identified in an influenza virus isolate or a plurality of influenza virus isolates predicted to have a greater infectivity than at least one other isolate of influenza virus and may comprise the shortest Replikin peptides from a pB1 gene area identified in an influenza virus isolate or a plurality of influenza virus isolates predicted to have a greater lethality than at least one other isolate of influenza virus.

A vaccine may further comprise a plurality of the longest Replikin peptides from a hemagglutinin protein area and a plurality of the longest Replikin peptides from a pB1 area. A vaccine may comprise the longest Replikin peptides from a hemagglutinin protein area identified in an influenza virus isolate or a plurality of influenza virus isolates predicted to have a greater infectivity than at least one other isolate of influenza virus and may comprise the longest Replikin peptides from a pB1 gene area identified in an influenza virus isolate or a plurality of influenza virus isolates predicted to have a greater lethality than at least one other isolate of influenza virus. A vaccine may also comprise a mixture of the shortest and longest Replikin peptides in the hemagglutinin protein area and/or pB1 gene area.

A vaccine may be directed against any influenza virus including, influenza A, influenza B, or influenza C. A vaccine may be directed against H1N1, H1N2, H2N2, H3N2, H3N8, H5N1, H5N2, H7N7, H7N2, H7N3, H9N2, H10N7, or any other strain of influenza A virus. Any of these vaccines may be synthesized in seven days or less, which allows for administration of vaccines that are a best fit for a particular virulent strain of virus.

A vaccine may be formulated with a pharmaceutically acceptable excipient, carrier, or adjuvant. One pharmaceutically acceptable carrier or excipient is water. Excipients, carriers, or adjuvants may include, but are not limited to, excipients, carriers and adjuvants known to those of skill in the art now or hereafter.

The compositions of the invention may be formulated for delivery by any available route including, but not limited to parenteral (e.g., intravenous), intradermal, subcutaneous, oral, nasal, bronchial, ophthalmic, transdermal (topical), transmucosal or any other routes. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Solutions or suspensions used for intranasal, intraocular, spray inhalation, parenteral (e.g., intravenous), intramuscular, intradermal, or subcutaneous application can include the following components: a sterile diluent such as water (for dermal, nasal, or ocular application, spraying, or injection), saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. Preparations may be enclosed in ampoules, disposable syringes or multiple dose vials made of glass or plastic.

Pharmaceutical compositions suitable for injectable use typically include sterile aqueous solutions (water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above.

Administration of the vaccine via any method may produce an immune response in the animal or human, it may further produce an antibody response in the animal or human. In a further non-limiting embodiment, the vaccine may produce a protective effect in the animal or human. For example, the vaccine of the present invention may be administered to a rabbit, a chicken, a shrimp, a pig, a ferret, a human, or any animal capable of an immune response. Because of the universal nature of Replikin sequences, a vaccine of the invention may be directed at a range of strains of influenza.

The vaccines of the present invention can be administered alone or in combination with antiviral drugs, such as gancyclovir; interferon; interleukin; M2 inhibitors, such as, amantadine, rimantadine; neuraminidase inhibitors, such as zanamivir and oseltamivir; and the like, as well as with combinations of antiviral drugs.

Generally, the dosage of peptides is in the range of from about 0.01 μg to about 500 mg, from about 0.05 μg to about 200 mg, about 0.075 μg to about 30 mg, about 0.09 μg to about 20 mg, about 0.1 μg to about 10 mg, about 10 μg to about 1 mg, and about 50 μg to about 500 μg. The skilled practitioner can readily determine the dosage and number of dosages needed to produce an effective immune response.

Compositions Comprising any of SEQ ID NO(s): 1-12, 13-20, 21-28, and 32-66

A non-limiting composition is provided comprising one or more isolated or synthesized peptides that are 30%, 40%, 50%, 60%, 70%, 80%, 90%, 95% or more homologous with at least one of the peptides of SEQ ID NO(s): 1-12, 13-20, 21-28, and 32-66. A composition is likewise provided comprising one or more isolated or synthesized peptides that are 30%, 40%, 50%, 60%, 70%, 80%, 90%, 95% or more homologous with at least one of the peptides of SEQ ID NO(s): 1-12 or SEQ ID NO(s): 21-28. A composition is provided comprising one or more isolated or synthesized peptides consisting of at least one peptide of SEQ ID NO(s): 1-12, 13-20, 21-28, and 32-66 or at least one peptide of SEQ ID NO(s): 1-12 or at least one peptide of SEQ ID NO(s): 21-28. A composition is further provided comprising two, three, four five, six, seven, eight, nine, ten, eleven, twelve, thirteen, fourteen, fifteen, sixteen, seventeen, eighteen, nineteen, or twenty or more isolated or synthesized peptides of SEQ ID NO(s): 1-12, 13-20, 21-28, and 32-66.

A composition comprising a mixture of peptides is provided wherein the mixture comprises at least each of the isolated or synthesized peptides of SEQ ID NO(s): 1-12 and/or at least each of the isolated or synthesized peptides of SEQ ID NO(s): 21-28. A mixture is provided that is equimolar. A mixture is also provided that is equal by weight. Such a composition may comprise about 10% by weight the peptide of SEQ ID NO: 1, it may comprise about 9% by weight the peptide of SEQ ID NO: 2, it may comprise about 10% by weight the peptide of SEQ ID NO: 3, it may comprise about 6% by weight the peptide of SEQ ID NO: 4, it may comprise about 8% by weight the peptide of SEQ ID NO: 5, it may comprise about 8% by weight the peptide of SEQ ID NO: 6, it may comprise about 7% by weight the peptide of SEQ ID NO: 7, it may comprise about 6% by weight the peptide of SEQ ID NO: 8, it may comprise about 10% by weight the peptide of SEQ ID NO: 9, it may comprises about 8% by weight the peptide of SEQ ID NO: 10, it may comprise about 7% by weight the peptide of SEQ ID NO: 11, and/or it may comprise about 11% by weight the peptide of SEQ ID NO: 12.

The composition may further comprise two, three, four, five, six, seven, eight, nine, ten, eleven, twelve, or more isolated or synthesized peptides of SEQ ID NO(s): 1-12 or two, three, four, five, six, seven, eight, or more isolated or synthesized peptides of SEQ ID NO(s): 21-28. The composition may also comprise any number of peptides of SEQ ID NO(s): 13-20. The composition may also comprise one or more isolated or synthesized peptides that are 30%, 40%, 50%, 60%, 70%, 80%, 90%, or 95% or more homologous with at least one of peptides SEQ ID NO(s): 1-12, SEQ ID NO(s) 13-20, and/or SEQ ID NO(s): 21-28. The composition may comprise two, three, four, five, six, seven, eight, nine, ten, eleven, twelve or more isolated or synthesized peptides that are 30%, 40%, 50%, 60%, 70%, 80%, 90%, or 95% or more homologous with at least one of peptides SEQ ID NO(s): 1-12, SEQ ID NO(s): 13-20, or SEQ ID NO(s): 21-28. The composition may further comprise a mixture of peptides comprising isolated or synthesized peptides of SEQ ID NO(s): 1-12, SEQ ID NO(s): 13-20, or SEQ ID NO(s): 21-28.

Conserved Replikin Peptides Across Influenza Strains

Identification of conserved Replikin peptides across strains of influenza virus has provided for the development of vaccines that may be directed across strains of influenza virus. Identification of conserved Replikin peptides in isolates of influenza of any strain may be accomplished in any way known to one of skill in the art now or hereafter. One method is by review of in silico sequences provided at www.pubmed.com. Peptides that share exact identity or 100% homology with earlier identified Replikin peptides may be tracked using computer searching methods. Peptides that share 30%, 40%, 50%, 60%, 70%, 80%, 90%, or 95% or more homology with an earlier identified Replikin peptide may also be tracked by computer methods.

For example, a vaccine has now been developed for prevention and treatment of infection of H5N1 virus. See, e.g., Example 1 below. The sequences that are used in the vaccine in Example 1 have now been identified as conserved across many different strains. For example, SEQ ID NO: 8 (HFQRKRRVRDN<u>M</u>TK<u>K</u>), which was originally identified in the pB1 gene area of H5N1, shares homology with SEQ ID NO: 13 (HFQRKRRVRDN<u>V</u>TK), which has been identified as conserved in the pB1-F2 gene area of H1N1. SEQ ID NO: 8 is homologous with SEQ ID NO: 13 in that the valine at position 12 in SEQ ID NO: 13 is substituted with a methionine in SEQ ID NO: 8. SEQ ID NO: 8 also has one additional lysine on its C-terminus. As a result of this homology, a vaccine comprising SEQ ID NO: 8 or SEQ ID NO: 13 may be used against either H1N1 or H5N1 or any other strain expressing a homologue of these sequences. If such a homologue is expressed in the pB1 gene area or the pB1-F2 gene area of a strain, the vaccine will be particularly useful against such a strain. Further, a vaccine containing SEQ ID NO(s): 1-12, as described above, is available as a vaccine against H1N1 strains as well as H5N1 strains of influenza virus since such a vaccine comprises the peptide of SEQ ID NO: 8.

Sequences that are homologues of SEQ ID NO(s): 1-12 are appropriate sequences for inclusion in a vaccine directed against influenza virus including, H1N1, H1N2, H2N2, H3N2, H3N8, H5N1, H5N2, H7N7, H7N2, H7N3, H9N2, H10N7, or any other strain of influenza A virus and against any strain of influenza B or influenza C virus. Likewise, sequences that are homologues of SEQ ID NO(s): 13-20 are appropriate sequences for inclusion in a vaccine directed against influenza virus including, H1N1, H1N2, H2N2, H3N2, H3N8, H5N1, H5N2, H7N7, H7N2, H7N3, H9N2, H10N7, or any other strain of influenza A virus and against any strain of influenza B or influenza C virus. Sequences that are homologues of SEQ ID NO(s): 21-28 are also appropriate sequences for inclusion in a vaccine directed against influenza virus including, H1N1, H1N2, H2N2, H3N2, H3N8, H5N1, H5N2, H7N7, H7N2, H7N3, H9N2, H10N7, or any other strain of influenza A virus and against any strain of influenza B or influenza C virus.

The above-discussed homologues are expected by one of ordinary skill in the art to provide antigenicity that is comparable to any one of SEQ ID NO(s): 1-12, SEQ ID NO(s): 13-20, SEQ ID NO(s): 21-28. Further, because these homologues are often conserved in the hemagglutinin and pB1 gene areas of different strains of influenza virus, these homologues are useful for developing antagonists against influenza infections, including for vaccinating a subject with the homologous peptides to stimulate the immune system of the subject against the peptides and in-turn against influenza virus proteins harboring such peptides or other homologues of such peptides.

Homology that is sufficient to produce a useful target for antagonism includes peptides that are 30%, 40%, 50%, 60%, 70%, 80%, 90%, 95%, or up to 100% homologous with any of SEQ ID NO(s): 1-12, 13-20, 21-28, and 32-66. Homology may be determined with peptides wherein gaps exists in the sequence that is being compared to any one of SEQ ID NO(s): 1-12, 13-20, 21-28, and 32-66 between amino acids that are identical to those of the peptide chosen from SEQ ID NO(s): 1-12. For example, SEQ ID NO: 1 (HAQDILEKEH-NGKLCSLKGVRPLILK) would be considered more than 86% homologous with the following sequence HAQDILEKEHNGKLCSLKGVRPX$_{n=4}$LILK (SEQ ID NO: 29) because SEQ ID NO: 1 is identical to SEQ ID NO: 29 in all residues except for the four residues represented by X$_{n=4}$. Likewise, SEQ ID NO: 1 is more than 86% homologous with HAQDXILEKEHNGKLCXSLKGVRXXPLILK (SEQ ID NO: 30) because it is identical to SEQ ID NO: 30 in all residues except for the residues represented by X. Because SEQ ID NO(s) 29 and 30 are 86% homologous with SEQ ID NO: 1, SEQ ID NO(s): 29 and 30 are available as peptides for inclusion in a vaccine directed against infectivity in H5N1 or in any influenza virus strain wherein homologues to SEQ ID NO: 1 are conserved.

Concerning gaps, the number of gaps in either the basis sequence or the identified sequence should be limited to the number of gaps allowable without significantly compromising the function of the identified sequence as compared to the basis sequence. In general, many gaps in the sequence of the basis peptide or in the sequence of the identified peptide are allowed based on homology as defined herein. Relatively more gaps are allowed if the lysines and histidines that create the definition of the Replikin peptide are identically shared between the basis peptide and the identified peptide. Relatively more gaps are also allowed if the lysines and histidines that create the definition of the Replikin peptide are shared at least in close position (for example within ten, nine, eight, seven, six, five, four, three, two, or one amino acid residue). If some of the lysines and histidines that create the definition of the Replikin peptide are not present in the identified peptide, fewer gaps may be allowed. Nevertheless, if the identified peptide functions similarly to the basis peptide, any number of gaps are allowed. In general, three or more gaps are allowed in the sequence of the basis peptide or in the sequence of the identified peptide within ten amino acid residues of the basis peptide if no lysines or histidines are present in the identified peptide. Two or more gaps or one or more gaps are also allowed. Nevertheless, if the identified sequence provides the same or a similar function to the basis sequence, more gaps are allowed up to the number of gaps that will provide a homology of 30%, 40%, 50%, 60%, 70%, 80%, 90%, 95%, or more homology. Additionally, where the lysines and histidines of the Replikin definition are present in both the identified peptide and the basis peptide, there should be no limit on how many gaps are allowed.

The presence of lysines and histidines providing for the Replikin definition in an identified peptide requires significantly less homology because the lysines and the histidines of the Replikin definition provide for conservation of Replikin function. For example, in Table 8 and the description thereof in columns 62 and 63 in U.S. Pat. No. 7,442,761, a highly mutable tat protein in HIV is described and analyzed. As may be seen from Table 8 in U.S. Pat. No. 7,442,761, in tat protein of HIV, which is essential for replication in the virus, lysines and histidines that are essential to maintaining the Replikin definition within a key Replikin peptide in the protein are observed to be 100% conserved, while substitutions in amino acid residues that are not essential to maintaining the Replikin definition are commonly substituted. The conservation of the key amino acids for maintaining the Replikin definition is understood to provide a specific survival function for HIV. The same phenomenon is seen in influenza. See U.S. Pat. No. 7,442,761, column 62, lines 42-45.

Sequences that are conserved across strains of influenza in the hemagglutinin and pB1 gene areas are excellent targets for controlling infectivity and lethality, respectively. As such, identification of conserved Replikin sequences in the hemagglutinin and pB1 gene areas in different strains of influenza including H1N1, H1N2, H2N2, H3N2, H3N8, H5N1, H5N2, H7N7, H7N2, H7N3, H9N2, H10N7, or any other strain of influenza A virus and against any strain of influenza B or influenza C virus, provides sequences that are provided as included in a cross-strain vaccine for influenza virus.

Conserved Replikin Sequences in Hemagglutinin Protein and the pB1 Gene Area in Vaccines to Provide Cross-Strain Protection One aspect of the invention, therefore, provides conserved sequences in the hemagglutinin protein area and conserved sequences in the pB1 gene area for diagnostic, predictive, and therapeutic purposes, including vaccines that provide cross-strain influenza protection. Replikin sequences that are shared across strains and Replikin sequence homologues that are shared across strains provide targets for diagnostic, predictive, and therapeutic purposes. Because Replikin sequences are associated by the applicants with mechanisms of rapid replication and because Replikin sequences in the hemagglutinin protein area and the pB1 gene area are associated by the applicants with infectivity and lethality, respectively, Replikin sequences that are shared across influenza strains or homologues of Replikin sequences that are shared across influenza strains provide excellent targets for diagnostics and therapeutics directed at these shared sequences. Identifying these targets provides for therapies such as a vaccine or a binding agent (e.g., an antibody or antibody fragment) that may be directed at Replikin sequences or their homologues in an array of influenza types and strains.

Replikin sequences have been identified by the applicants that are shared among, for example, H1N1, H5N1, H3N2, and H9N2. Such conserved sequences provide targets for vaccines that provide cross-strain protection in these strains of influenza A and provide cross-strain protection in strains that share the sequences or homologues of the sequences. For example, the applicants have identified five Replikin sequences in the H1N1 pB1-F2 gene area that are conserved within H1N1 and are shared with H5N1 or H3N2.

One such sequence is HFQRKRRVRDNVTK (SEQ ID NO: 13). SEQ ID NO: 13 has been observed to be conserved at position 184 in the pB1-F2 gene area in isolates of H1N1 since at least 1948 and shares homology with SEQ ID NO: 8 (HFQRKRRVRDN<u>M</u>TK<u>K</u>), which was originally identified by the applicants in the pB1 gene area of H5N1 and has been observed to be conserved from 2000 through 2009 in isolates of H5N1 virus. See, e.g., Accession No. AAF74314. SEQ ID NO: 8 is homologous with SEQ ID NO: 13 in that the valine at position 12 in SEQ ID NO: 13 is substituted with a methionine in SEQ ID NO: 8. SEQ ID NO: 8 also has one additional lysine on its C-terminus. As a result of this homology, a vaccine comprising SEQ ID NO: 8 or SEQ ID NO: 13 may be used against either H1N1 or H5N1 or any other strain expressing a homologue of these sequences. If such a homologue is expressed in the pB1 gene area or the pB1-F2 gene area of a strain, the vaccine will be particularly useful against such a strain. Further, a vaccine containing SEQ ID NO(s): 1-12, as described above, is available as a vaccine against H1N1 strains as well as H5N1 strains of influenza virus since such a vaccine comprises the peptide of SEQ ID NO: 8. A vaccine comprising SEQ ID NO(s): 1-12, then, provides an example of a vaccine to be used as a cross-strain vaccine.

As a further example of the conservation of Replikin sequences in the pB1-F2 gene area of various strains of influenza, the sequence HCQKTMNQVVMPK (SEQ ID NO: 14) has been observed as conserved at position 41 in the pB1-F2 gene area of isolates of H1N1 since 1918 and a homologue is also conserved at position 41 in the pB1-F2 gene area of isolates of H3N2 in at least 1968, 2004, 2006, and 2008. See, e.g., Accession Nos. ABI922289, ACK99430, ACI26481, ACI26437, and ACI 26294. In addition, SEQ ID NO: 14 is further conserved in H1N1 with a substitution of the cysteine residue at position 2 by a tyrosine residue. The resulting sequence is H<u>Y</u>QKTMNQVVMPK (SEQ ID NO: 15), which has been observed as conserved at position 41 in the pB1-F2 gene area of H1N1 isolates of H1N1 from at least 1951 through 1983. SEQ ID NO: 15 has also been observed as conserved in H5N1. In view of the conservation of SEQ ID NO(s): 14 and 15 or their homologues in H1N1, H5N1, and H3N2, a vaccine comprising a peptide of SEQ ID NO(s): 14 or 15 or homologues of one of those sequences is available as a vaccine against H1N1, H5N1, and H3N2 strains of influenza virus or any strain expressing a homologue of the peptides.

The sequence KRWRLFSKH (SEQ ID NO: 16) has been observed to be conserved at position 78 of the pB1-F2 gene area of H1N1 in isolates from 1918 through 2008. SEQ ID NO: 16 is also conserved at position 78 of the pB1-F2 gene area of H3N2 in at least 1968 and 2008. See, e.g. Accession Nos. ABI92289, ACK99430, ACI26481, ACI26437, ACI26294. A vaccine comprising SEQ ID NO: 16 is, therefore, available against both H1N1 and H3N2 or any other influenza strain expressing one or more homologues of SEQ ID NO: 16.

The sequence KKKHKLDK (SEQ ID NO: 17) is also conserved at position 207 of the pB1-F2 gene area of isolates of H1N1 in isolates from at least 1991 through 2009. SEQ ID NO: 17 is also conserved in H5N1. A homologue of SEQ ID NO: 17, namely, sequence KKKQRLTKX$_n$H (SEQ ID NO: 18) (where n=any amino acid from 1 to 41 residues), is conserved in the pB1 gene area of isolates of H1N1 and H5N1 at position 207. As such, a vaccine comprising SEQ ID NO(s): 17 or 18 is available against H1N1 and H5N1 or any influenza strain expressing homologues of these sequences.

The sequence HFQRKRRVRDNMTK (SEQ ID NO: 19) is also conserved at position 184 in the pB1 gene area of H5N1 in isolates from at least 2000 through 2009. See, e.g., Accession No. AAF74314. SEQ ID NO: 19 is a 93% homologue with SEQ ID NO: 8 with only one additional lysine on the c-terminus. SEQ ID NO: 19 is also a homologue of SEQ ID NO: 13 with about 93% homology. SEQ ID NO: 19 is conserved in H1N1 at position 184 as well as in H9N2.

Another homologue of SEQ ID NO(s): 8 and 19 is HFQRKRRVRDNMTKKMVTQRTIGKKKQRLNK (SEQ ID NO: 20), which is conserved at position 184 in the pB1 gene area of H5N1 isolates from at least 2000 through 2005. See Accession No. AAF74314. SEQ ID NO: 20 is 48% homologous with SEQ ID NO: 8 and 45% homologous with SEQ ID NO: 19. All of these sequences share homology with SEQ ID NO: 13, which has been observed to be conserved at position 184 in the pB1-F2 gene area in isolates of H1N1 since at least 1948. A vaccine comprising SEQ ID NO(s): 8, 13, 19, or 20, or any combination thereof, is available against H1N1, H5N1, H9N2 or any influenza strain expressing homologues of these sequences.

Methods of Designing Vaccines

The invention also provides methods of designing and making vaccines. For example, the invention provides a method of making a vaccine comprising selecting at least one or more isolated or synthesized peptides of SEQ ID NO(s): 1-12, SEQ ID NO(s): 13-20, or SEQ ID NO(s): 21-28 as a component of a vaccine and making said vaccine. The method may comprise selecting from 1 to up to 12 or more isolated or synthesized peptides of SEQ ID NO(s): 1-12, SEQ ID NO(s): 13-20, or SEQ ID NO(s): 21-28 as a component of a vaccine. The method may comprise identifying one or more peptides of SEQ ID NO(s): 1-12, SEQ ID NO(s): 13-20, or SEQ ID NO(s): 21-28 in an emerging strain of influenza virus up to about 3 years before the vaccine is made. The method may comprise identifying one or more peptides of SEQ ID NO(s): 1-12, SEQ ID NO(s): 13-20, or SEQ ID NO(s): 21-28 in an emerging strain of influenza virus up to about 1 year before the vaccine is made. The method may comprise identifying one or more peptides of SEQ ID NO(s): 1-12, SEQ ID NO(s): 13-20, or SEQ ID NO(s): 21-28 in an emerging strain of influenza virus up to about 6 months before the vaccine is made. The method may comprise identifying one or more peptides of SEQ ID NO(s): 1-12, SEQ ID NO(s): 13-20, or SEQ ID NO(s): 21-28 in an emerging strain of influenza virus up to about 7 days before the vaccine is made.

An emerging strain may be any strain of influenza virus identified by one of skill in the art as a strain of influenza virus that is predicted to expand in a population in hosts or that is predicted to increase in virulence, morbidity, and or mortality in its hosts. An emerging strain may likewise be a strain of influenza virus wherein Replikin concentration is observed to be increasing over time. An emerging strain may likewise be a strain of influenza virus identified within a rising portion of Replikin cycle, following a peak in a Replikin cycle, following a step-wise rise in a Replikin cycle, or identified by a Replikin Count Virus Expansion Index as an emerging strain of virus. See U.S. application Ser. No. 12/429,044, filed Apr. 23, 2009, which is incorporated herein by reference.

A method of making a vaccine is also provided comprising: selecting at least one isolated or synthesized protein, protein fragment, polypeptide, or peptide comprising a homologue of SEQ ID NO(s): 1-12, 13-20, 21-28, and 32-66 as a component of a vaccine; and making said vaccine. An isolated or synthesized protein, protein fragment, polypeptide, or peptide may comprise a peptide that is 30%, 40%, 50%, 60%, 70%, 80%, 90% or 95%, or 100%, homologous with at least one of SEQ ID NO(s): 1-12, 13-20, 21-28, and 32-66. At least two, three, four, five, six, seven, eight, nine, ten, eleven, twelve, or more homologues of SEQ ID NO(s): 1-12, 13-20, 21-28, and 32-66 may be selected. Also, at least two, three, four, five, six, seven, eight, nine, ten, eleven, twelve, or more peptides of SEQ ID NO(s): 1-12, 13-20, 21-28, and 32-66 may be selected. The isolated or synthesized protein, protein fragment, polypeptide, or peptide may have the same amino acid sequence as at least one protein, protein fragment, polypeptide or peptide identified in an emerging strain of influenza virus up to one, two, or three or more years prior to making said vaccine. The at least one protein, protein fragment, polypeptide or peptide may be identified in an emerging strain of influenza virus one week, one month, two months, three months, four months, five months, or six months prior to making said vaccine.

A method of making a vaccine is provided comprising: selecting as a component of the vaccine at least one protein fragment, polypeptide, or peptide comprising at least one peptide A, where peptide A is at least 30%, 40%, 50%, 60%, 70%, 80%, 90% or 95%, or 100%, homologous with at least one of SEQ ID NO(s): 1-12, 13-20, 21-28, and 32-66 isolated from a hemagglutinin protein area (or a synthesized version thereof), and selecting as a component of the vaccine at least one protein fragment, polypeptide, or peptide comprising at least one peptide B, where peptide B is at least 30%, 40%, 50%, 60%, 70%, 80%, 90% or 95%, or 100%, homologous with at least one of SEQ ID NO(s): 1-12, 13-20, 21-28, and 32-66 isolated from a pB1 gene area (or a synthesized version thereof); and making a vaccine comprising the components.

A method of making a vaccine is also provided comprising: identifying (1) at least one protein, protein fragment, polypeptide, or peptide of a hemagglutinin protein area in or derived from an isolate of influenza virus having relatively greater infectivity than another isolate of influenza virus or a plurality of isolates of influenza viruses, and (2) at least one protein, protein fragment, polypeptide, or peptide of a pB1 gene area in or derived from an isolate of influenza virus having relatively greater lethality than another isolate of influenza virus or a plurality of isolates of influenza virus; and making a vaccine comprising the at least one protein, protein fragment, polypeptide, or peptide of a hemagglutinin protein area and the at least one protein, protein fragment, polypeptide, or peptide of a pB1 gene area.

The invention also provides a kit for making a vaccine where the kit includes at least one isolated or synthesized peptide of SEQ ID NO(s): 1-12, 13-20, 21-28, and 32-66 or homologues of SEQ ID NO(s): 1-12, 13-20, 21-28, and 32-66. The kit may also include two, three, four, and up to twelve or more peptides of SEQ ID NO(s): 1-12, 13-20, 21-28, and 32-66 or homologues of SEQ ID NO(s): 1-12, 13-20, 21-28, and 32-66.

For the first time, new non-biological software and organic chemical totally synthetic methods have been developed to manufacture vaccines, based on the discovery of Replikins. The centrality of Replikins to influenza infectivity has been recently confirmed by the data of two groups, Harvard-CDC and Scripps-Crucell, demonstrating that inhibitory antibody lands on and binds selectively to previously defined Replikins. Three months to one year in advance of any outbreak, the related FluForecast® software technology warns of the coming emergent disease, as recently demonstrated one year in advance of the current H1N1 outbreak, and defines the Replikins to be synthesized in the vaccine.

The new vaccine technology has been tested and demonstrated to work in independent trials against influenza H5N1 virus in chickens, and against lethal Taura Syndrome virus in shrimp. Both TransFlu™ (the first synthetic cross-strain Pan Flu vaccine) and Taura Syndrome Virus vaccines have been manufactured in 7 days. Kilogram amounts of these vaccines may be manufactured in a few weeks, rather than 6 to 12 months by biological methods. The cost is far less than the cost of vaccines by current biological methods.

The invention further provides preventing or treating influenza in a human or animal by methods comprising administering at least one isolated or synthesized peptide of SEQ ID NO(s): 1-12, 13-20, 21-28, and 32-66 to the animal or human. The at least one isolated or synthesized peptide is administered intravenously, intramuscularly, orally, intranasally, intraocularly, via spray inhalation, or by any method of administration known to one of ordinary skill in the art now or hereafter. The vaccine may be administered intranasally, intraocularly, or via spray inhalation. The vaccine may be administered to a human, a bird, a horse, a ferret, or a pig. The bird may be a domestic bird or a wild bird and may include a chicken, a duck, a goose, or any other domestic or wild bird. The vaccine may be administered to a chicken including to a chicken at 7, 14, and 21 days after hatch.

A non-limiting vaccine of the invention is provided for, among other things, treatment or prevention of all strains of influenza virus. A non-limiting vaccine of the invention may contain sequences that are conserved in strains of Low-Path H5N1, strains of High-Path H5N1, and across other strains of influenza virus including H1N1, H1N2, H2N2, H3N2, H3N8, H5N1, H5N2, H7N7, H7N2, H7N3, H9N2, H10N7, or any other strain of influenza A virus, influenza B virus, or influenza C virus. SEQ ID NO(s): 1-12, 13-20, 21-28, and 32-66 of the invention have been observed to be conserved across many strains of influenza with particular conservation noted in the lysine and histidine residues of the sequences. The lysine and histidine residues of SEQ ID NO(s): 1-12, 13-20, 21-28, and 32-66 are the key amino acid residues that provide the Replikin structure of the sequences. SEQ ID NO(s): 1-12, 13-20, 21-28, and 32-66 have likewise been observed to be conserved in both High-Path and Low-Path H5N1 and are useful in both treatment and prevention for outbreaks of these strains of influenza as well as all other strains of influenza.

Methods of Differentiating Infectivity from Lethality in Influenza Virus

One non-limiting aspect of the present invention provides methods of differentiating the infectivity of an influenza virus isolate or strain of influenza virus from the lethality of the influenza virus isolate or strain of influenza virus. Compounds for diagnostic, therapeutic, and/or preventive purposes in influenza and therapies for the prevention and treatment of influenza are provided based on the disclosed methods of differentiation.

A method of differentiating the relative infectivity of isolate A of influenza virus from the relative infectivity of isolate B of influenza virus and the relative lethality of isolate A of influenza virus from the relative lethality of isolate B of influenza virus is provided comprising: comparing the Replikin Count of the hemagglutinin protein area of isolate A to the Replikin Count of the hemagglutinin protein area of isolate B; and comparing the Replikin Count of the pB1 gene area of isolate A to the Replikin Count of the pB1 gene area of isolate B. The relative infectivity of isolate A may be greater than, less than, or about the same as the relative infectivity of isolate B if the Replikin Count of the hemagglutinin protein area of isolate A is greater than, less than, or about the same as the Replikin Count of the hemagglutinin protein area of isolate B, respectively, and the relative lethality of isolate A may be greater than, less than, or about the same as the relative lethality of isolate B if the Replikin Count of the pB1 gene area of isolate A is greater than, less than, or about the same as the Replikin Count of the pB1 gene area of isolate B, respectively.

The relative infectivity of isolate A may also be greater than, less than, or about the same as the relative infectivity of isolate B and the relative lethality of isolate A may not be concomitantly greater than, less than, or about the same as the relative lethality of isolate B. The relative infectivity of isolate A may likewise be greater than the relative infectivity of isolate B and the relative lethality of isolate A may be less than or about the same as the relative lethality of isolate B. The relative infectivity of isolate A may also be less than the relative infectivity of isolate B and the relative lethality of isolate A may be greater than or about the same as the relative lethality of isolate B. The relative lethality of isolate A may also be greater than, less than, or about the same as the relative lethality of isolate B and the relative infectivity of isolate A may be not concomitantly greater than, less than, or about the same as the relative infectivity of isolate B.

A method of differentiating the relative infectivity and relative lethality of a plurality of isolates A of influenza from a given region or time period from the relative infectivity and relative lethality of an isolate B from a different region or different time period or from the relative infectivity and relative lethality of a plurality of isolates B from a different region or different time period is also provided, comprising: comparing the mean Replikin Count of the hemagglutinin protein area and the mean Replikin Count of the pB1 gene area of the plurality of isolates A to the Replikin Count of the hemagglutinin protein area of isolate B or the mean Replikin Count of the hemagglutinin protein area of the plurality of isolates B, and to the Replikin Count of the pB1 gene area of isolate B or to the mean Replikin Count of the pB1 gene area of the plurality of isolates B. A plurality of isolates A of influenza from a given region or time period may have a relative infectivity that is greater than, less than, or about the same as the relative infectivity of isolate B or the plurality of isolates B if the mean Replikin Count of the hemagglutinin protein area of the plurality of isolates A is greater than, less than, or about the same as the Replikin Count of the hemagglutinin protein area of isolate B or is greater than, less than, or about the same as the mean Replikin Count of the hemagglutinin protein area of the plurality of isolates B, and the relative lethality of the plurality of isolates A is greater than, less than, or about the same as the relative lethality of isolate B or the plurality of isolates B if the mean Replikin Count of the pB1 gene area of the plurality of isolates A is greater than, less than, or about the same as the Replikin Count of the pB1 gene area of isolate B or is greater than, less than, or about the same as the mean Replikin Count of the pB1 gene area of the plurality of isolates B.

The relative infectivity of the plurality of isolates A may also be greater than, less than, or about the same as the relative infectivity of isolate B or the relative infectivity of the plurality of isolates B, and the relative lethality of the plurality of isolates A may be not concomitantly greater than, less than, or about the same as the relative lethality of isolate B or the relative lethality of the plurality of isolates B. The relative infectivity of the plurality of isolates A may also be greater than the relative infectivity of the plurality of isolates B and the relative lethality of isolate A may be less than or about the same as the relative lethality of isolate B or the relative lethality of the plurality of isolates B. The relative infectivity of the plurality A of isolates may also be less than the relative infectivity of isolate B or the relative infectivity of the plurality of isolates B, and the relative lethality of plurality of isolates A may be greater than or about the same as the relative lethality of isolate B or the relative lethality of the plurality of isolates B. The relative lethality of the plurality of isolates A may also be greater than, less than, or about the same as the relative lethality of isolate B or the relative lethality of the plurality of isolates B and the relative infectivity of the plurality of isolates A may be not concomitantly greater than, less than, or about the same as the relative infectivity of isolate B or the relative infectivity of the plurality of isolates B.

A method of differentiating the future relative infectivity of at least one strain A of influenza virus as compared to a time $T_0$ from the future relative lethality of said at least one strain A of influenza virus as compared to time $T_0$ is also provided comprising: comparing a trend of Replikin Counts in the hemagglutinin protein area of a plurality of isolates of strain A ending at time $T_0$, wherein said isolates are isolated at different time periods including time $T_0$, to a trend of Replikin Counts in the pB1 gene area of a plurality of isolates of strain A ending at time $T_0$, wherein said isolates are isolated at different time periods including time $T_0$.

The future relative infectivity of strain A may be predicted to be greater than, less than, or about the same as the relative infectivity of strain A at time $T_0$ if the trend of Replikin Counts in the hemagglutinin protein area of said plurality of isolates of strain A is rising, falling, or remaining about the same and the future relative lethality of strain A may be predicted to be greater than, less than, or about the same as the relative lethality of strain A at time $T_0$ if the trend of Replikin Counts in the pB1 gene area of said plurality of isolates of strain A is rising, falling, or remaining about the same.

The future relative infectivity of strain A may also be predicted to be greater than, less than, or about the same as the relative infectivity of strain A at time $T_0$ and the future relative lethality of strain A may be not concomitantly greater than, less than, or about the same as the relative lethality of strain A at time $T_0$. The future relative infectivity of strain A may also be predicted to be greater than the relative infectivity of strain A at time $T_0$ and the relative lethality of strain A may be predicted to be less than or about the same as the relative lethality of strain A at time $T_0$. The future relative infectivity of strain A may also be predicted to be less than the relative infectivity of strain A at time $T_0$ and the relative lethality of strain A may be predicted to be greater than or about the same as the relative lethality of strain A at time $T_0$.

A vaccine is also provided comprising at least one Replikin amino acid sequence from the hemagglutinin protein area of an isolate of influenza virus and at least one Replikin amino acid sequence from the pB1 gene area of an isolate of influenza virus. The at least one Replikin amino acid sequence from the hemagglutinin protein area may be from an isolate of influenza virus predicted to have a greater infectivity than at least one other isolate of influenza virus and the at least one Replikin amino acid sequence from the pB1 gene area may be from an isolate of influenza virus predicted to have a greater lethality than at least one other isolate of influenza virus. A vaccine may also comprise at least one Replikin amino acid sequence from the hemagglutinin protein area and at least one Replikin amino acid sequence from the pB1 gene area isolated from (or a synthesized version of) an isolate of influenza predicted to have a greater infectivity and a greater lethality than at least one other isolate of influenza. A vaccine may also comprise a plurality of Replikin peptides from the hemagglutinin protein area and a plurality of peptides from the pB1 gene area.

A computer readable storage medium is also provided having stored thereon instructions which, when executed, cause a processor to perform a method of differentiating the relative infectivity of an influenza virus from the relative lethality of an influenza virus. A processor may report the differentiation of the relative infectivity of the influenza virus from the relative lethality of the influenza virus to a display, user, researcher, or other machine or person. The reported differentiation may report whether the relative infectivity of the virus is greater than, less than, or about equal to the relative infectivity of another virus and whether the relative lethality of the virus is greater than, less than, or about equal to the relative lethality of another virus.

Methods of Treating Influenza Across Strains

A method of preventing or treating influenza virus infection across different strains is provided comprising administering at least one isolated or synthesized protein, protein fragment, polypeptide, or peptide comprising a homologue of SEQ ID NO(s): 1-12, 13-20, 21-28, and 32-66 to an animal or human. The isolated or synthesized protein, protein fragment, polypeptide, or peptide may comprise a peptide that is 30%, 40%, 50%, 60%, 70%, 80%, 90% or 95%, or 100%, homologous with at least one of SEQ ID NO(s): 1-12, 13-20, 21-28, and 32-66. A method may comprise administering at least one, two, three, four, five, six, seven, eight, nine, ten, eleven, or twelve or more peptide(s) that is (are) 30%, 40%, 50%, 60%, 70%, 80%, 90% or 95%, or 100%, homologous with at least one of SEQ ID NO(s): 1-12, 13-20, 21-28, and 32-66 or may comprise administering at least one, two, three, four, five, six, seven, eight, nine, ten, eleven, or twelve or more peptide(s) that consist(s) of at least one of SEQ ID NO(s): 1-12, 13-20, 21-28, and 32-66. A method may further comprise administering at least one isolated or synthesized protein fragment, polypeptide, or peptide that consists of at least one peptide A, which is at least 30%, 40%, 50%, 60%, 70%, 80%, 90%, or 95% or more homologous with at least one of the peptides of SEQ ID NO(s): 1-12, 13-20, 21-28, and 32-66.

A method of preventing or treating influenza virus infection across strains may also comprise administering at least one agent that is capable of antagonizing a protein comprising a homologue of SEQ ID NO(s): 1-12, 13-20, 21-28, and 32-66 wherein said agent is capable of binding at least a portion of said homologue that is at least 30%, 40%, 50%, 60%, 70%, 80%, 90% or 95%, or 100%, homologous with at least one of SEQ ID NO(s): 1-12, 13-20, 21-28, and 32-66.

Antibodies as Diagnostics and Therapies for Identified Replikin Sequences

In another aspect of the invention, isolated Replikin peptides may be used to generate antibodies, antibody fragments, or to generate or identify other binding agents, which may be used, for example for diagnostic purposes or to provide passive immunity in an individual. See, e.g., U.S. application Ser. No. 11/355,120, filed Feb. 16, 2006 and U.S. application Ser. No. 12/010,027, filed Jan. 18, 2008 (each incorporated herein by reference in their entirety).

Various procedures known in the art may be used for the production of antibodies to Replikin sequences or to proteins, protein fragments, polypeptides, or peptides comprising Replikin sequences. Such antibodies include, but are not limited to, polyclonal, monoclonal, chimeric, humanized, single chain, Fab fragments and fragments produced by a Fab expression library. Antibodies that are linked to a cytotoxic agent may also be generated. Antibodies may also be administered in combination with an antiviral agent. Furthermore, combinations of antibodies to different Replikins may be administered as an antibody cocktail.

For the production of antibodies, various host animals or plants may be immunized by injection with a Replikin peptide or a combination of Replikin peptides, including, but not limited to, rabbits, mice, rats, and larger mammals. Monoclonal antibodies to Replikins may be prepared using any technique that provides for the production of antibody molecules. These include but are not limited to the hybridoma technique originally described by Kohler and Milstein, (*Nature,* 1975, 256:495-497), the human B-cell hybridoma technique (Kosbor et al., 1983, *Immunology Today,* 4:72), and the EBV hybridoma technique (Cole et al., *Monoclonal Antibodies and Cancer Therapy*, Alan R. Liss, Inc., pp. 77-96). In addition, techniques developed for the production of chimeric antibodies (Morrison et al., 1984, Proc. Nat. Acad. Sci USA, 81:6851-6855) or other techniques may be used. Alternatively, techniques described for the production of single chain antibodies (U.S. Pat. No. 4,946,778) can be adapted to produce Replikin-specific single chain antibodies. Antibody fragments that contain binding sites for a Replikin may be generated by known techniques. For example, such fragments include but are not limited to F(ab')2 fragments which can be produced by pepsin digestion of the antibody molecules and the Fab fragments that can be generated by reducing the disulfide bridges of the F(ab')2 fragments. Alternatively, Fab expression libraries can be generated (Huse et al., 1989, Science, 246:1275-1281) to allow rapid and easy identification of monoclonal Fab fragments with the desired specificity.

Binding agents are provided including an antibody, antibody fragment, or binding agent that binds to at least a portion of an amino acid sequence of at least one protein, protein fragment, polypeptide, or peptide comprising at least one peptide A, where peptide A is at least 30%, 40%, 50%, 60%, 70%, 80%, 90% or 95%, or 100%, homologous with at least one of SEQ ID NO(s): 1-12, 13-20, 21-28, and 32-66. The amino acid sequence of a protein fragment, polypeptide, or peptide may partially match the amino acid sequence of an expressed whole protein where at least one, five, ten, twenty, thirty, forty, fifty, one hundred, two hundred, three hundred, four hundred, five hundred or more amino acid residues of the amino acid sequence of the expressed whole protein are not present in the protein fragment, polypeptide, or peptide. The amino acid sequence of the protein fragment, polypeptide, or peptide may also partially match the amino acid sequence of an expressed whole protein where at least one, ten, twenty, thirty, forty, fifty, sixty, seventy, eighty, ninety, one hundred, one hundred fifty, two hundred, two hundred fifty, three hundred, three hundred fifty, four hundred, four hundred fifty, five hundred, five hundred fifty or more amino acid residues of the amino acid sequence of at least one terminus of the expressed whole protein are not present at least one terminus of said protein fragment, polypeptide, or peptide.

Binding agents are also provided including an antibody, antibody fragment, or binding agent that binds to at least a portion of an amino acid sequence that is 30%, 40%, 50%, 60%, 70%, 80%, 90%, or 95% or more homologous with at least one of the peptides of SEQ ID NO(s): 1-12, 13-20, 21-28, and 32-66. In a non-limiting embodiment, the length of peptide A may be no more than one, five, ten, twenty, thirty, forty, or fifty amino acid residues longer than the sequence of SEQ ID NO(s): 1-12, 13-20, 21-28, and 32-66 with which it is homologous. Binding agents are also provided that bind to at least a portion of an amino acid sequence of at least one of SEQ ID NO(s): 1-12, 13-20, 21-28, and 32-66.

Binding agents may specifically bind to the target protein, protein fragment, polypeptide, or peptide. Binding agents may specifically bind to a homologue of at least one of SEQ ID NO(s): 1-12, 13-20, 21-28, and 32-66. Binding agents may likewise specifically bind to a peptide consisting of any one of SEQ ID NO(s): 1-12, 13-20, 21-28, and 32-66. Binding agents may also specifically bind to a portion of a peptide consisting of any one of SEQ ID NO(s): 1-12, 13-20, 21-28, and 32-66 including a single amino acid within a homologue of SEQ ID NO(s): 1-12, 13-20, 21-28, and 32-66, two amino acids, three amino acids, four amino acids, five amino acids, or any number of amino acids spread within or outside a homologue.

Nucleic Acids and Compositions of Nucleic Acids An isolated or synthesized nucleic acid sequence is also provided that encodes a protein, protein fragment, polypeptide, or peptide comprising at least one peptide A, where peptide A is at least 30%, 40%, 50%, 60%, 70%, 80%, 90% or 95%, or 100%, homologous with at least one of SEQ ID NO(s): 1-12, 13-20, 21-28, and 32-66. A nucleic acid sequence may also encode a protein, a protein fragment, a polypeptide, or a peptide where the amino acid sequence of the protein, protein fragment, polypeptide, or peptide partially matches the amino acid sequence of an expressed whole protein and at least one, two, three, four, five, ten, twenty, thirty, forty, fifty, one hundred, two hundred, three hundred, four hundred, five hundred or more amino acid residues of the amino acid sequence of the expressed whole protein are not present in the protein fragment, polypeptide, or peptide. Further, the amino acid sequence of the protein, protein fragment, polypeptide, or peptide may partially match the amino acid sequence of an expressed whole protein where at least one, two, three, four, five, ten, twenty, thirty, forty, fifty, sixty, seventy, eighty, ninety, one hundred, one hundred fifty, two hundred, two hundred fifty, three hundred, three hundred fifty, four hundred, four hundred fifty, five hundred, five hundred fifty or more amino acid residues of the amino acid sequence of at least one terminus of the expressed whole protein may not be present at least one terminus of the protein, protein fragment, polypeptide, or peptide An isolated or synthesized nucleic acid sequence may also encode a peptide consisting of 7 to about 50 amino acid residues comprising at least one of the peptide sequences of SEQ ID NO(s): 1-12, 13-20, 21-28, and 32-66. It may also encode a peptide that is at least 30%, 40%, 50%, 60%, 70%, 80%, 90%, or 95% or more homologous with at least one of the peptide sequences of SEQ ID NO(s): 1-12, 13-20, 21-28, and 32-66. It may also encode a peptide consisting of at least one of the peptide sequences of SEQ ID NO(s): 1-12, 13-20, 21-28, and 32-66.

The invention further provides an immunogenic composition that comprises an isolated or synthesized nucleic acid provided above. The invention further provides a vaccine against influenza comprising an isolated or synthesized nucleic acid provided above.

Anti-Sense Nucleic Acids and siRNA

The invention further provides a nucleic acid sequence that is antisense to a nucleic acid that encodes for any one of SEQ ID NO(s): 1-12, 13-20, 21-28, and 32-66 or a small interfering nucleic acid sequence that interferes with a nucleic acid sequence that is 30%, 40%, 50%, 60%, 70%, 80%, 90%, or 95% or more homologous with a nucleic acid that encodes any one of SEQ ID NO(s): 1-12, 13-20, 21-28, and 32-66 or is 30%, 40%, 50%, 60%, 70%, 80%, 90%, 95% or more homologous with a nucleic acid that is antisense to a nucleic acid that encodes for any one of SEQ ID NO(s): 1-12, 13-20, 21-28, and 32-66.

The nucleotide sequence of the invention may be used in hybridization assays of biopsied tissue or blood, e.g., Southern or Northern analysis, including in situ hybridization assays, to diagnose the presence of a particular influenza strain in a tissue sample or an environmental sample, for example. The present invention also provides kits containing antibodies specific for particular Replikins that are present in a particular pathogen of interest, or containing nucleic acid molecules (sense or antisense) that hybridize specifically to a particular Replikin, and optionally, various buffers and/or reagents needed for diagnosis.

Also within the scope of the invention are oligoribonucleotide sequences that include antisense RNA and DNA molecules and ribozymes that function to inhibit the translation of Replikin-containing mRNA. Both antisense RNA and DNA molecules and ribozymes may be prepared by any method known in the art. The antisense molecules can be incorporated into a wide variety of vectors for delivery to a subject. The skilled practitioner can readily determine the best route of delivery, although generally intravenous or intramuscular delivery is routine. The dosage amount is also readily ascertainable.

The invention further provides antisense nucleic acid molecules that are complementary to a nucleic acid of the invention, wherein the antisense nucleic acid molecule is complementary to a nucleotide sequence encoding a peptide of the invention. In particular the nucleic acid sequence may be anti-sense to a nucleic acid sequence that has been demonstrated to be conserved over a period of six months to one or more years and/or which are present in a strain of influenza virus shown to have an increase in concentration of Replikins relative to Replikin concentration in other influenza virus strains.

The invention also provides compositions comprising RNAi-inducing entities used to inhibit or reduce influenza virus infection or replication including small interfering RNA, which is a class of about 10 to about 50 and often about 20 to about 25 nucleotide-long double-stranded RNA molecules. siRNA is involved in the RNA interference pathway, where it interferes with the expression of a specific genes such as the hemagglutinin gene or the pB1 gene area of influenza. siRNAs also act in RNAi-related pathways, e.g., as an antiviral mechanism.

An effective amount of an RNAi-inducing entity is delivered to a cell or organism prior to, simultaneously with, or after exposure to influenza virus. A dosage may be sufficient to reduce or delay one or more symptoms of influenza virus infection. Compositions of the invention may comprise a single siRNA species targeted to a target transcript or may comprise a plurality of different siRNA species targeting one or more target transcripts.

The invention provides a small interfering nucleic acid sequence that is about 10 to about 50 nucleic acids in length and is 30%, 40%, 50%, 60%, 70%, 80%, 90%, or 95% or more homologous with a nucleic acid that encodes for any portion of SEQ ID NO(s): 1-12, 13-20, 21-28, and 32-66 or is 30%, 40%, 50%, 60%, 70%, 80%, 90%, or 95% or more homologous with a nucleic acid that is antisense to a nucleic acid that encodes for any portion of one of SEQ ID NO(s): 1-12, 13-20, 21-28, and 32-66. In a further non-limiting embodiment, the nucleic acid sequence is about 15 to about 30 nucleic acids. In a further non-limiting embodiment, the nucleic acid sequence is about 20 to about 25 nucleic acids. In a further non-limiting embodiment, the nucleic acid sequence is about 21 nucleic acids.

Advance Replikin-Based Information on Pathogenic Outbreaks Provides for Rapid Production of Vaccines Advance information concerning Replikin peptides and Replikin Peak Genes in expanding strains of pathogen allows for the rapid production of specific effective synthetic vaccines using one, or a combination, of Replikin peptides or using Replikin Peak Genes. Such synthetic vaccines have been demonstrated in rabbits, chickens, and shrimp. See, e.g., Example 1 herein, Examples 6 and 7 of U.S. application Ser. No. 11/355,120, filed Feb. 16, 2006, and Example 2 of U.S. application Ser. No. 12/108,458, filed Apr. 23, 2008. For example, a mixture of Replikin peptides administered orally to shrimp provided up to a 91% protective effect for shrimp challenged with taura syndrome virus. Taura syndrome virus is an often lethal rapidly-replicating pathogen that has a significant negative impact on the shrimp industry.

Synthetic Replikin vaccines have also been demonstrated in the H5N1 strain of influenza virus in chickens. For example, in a test of chickens administered a mixture of twelve H5N1 Replikin peptides from the hemagglutinin and pB1 gene areas intranasally, intraocularly, and by spray inhalation and challenged with low pathogenic H5N1 influenza isolated from a black duck in the state of North Carolina in the United States, a protective effect was observed at both the entry site of influenza (diminished antibody production in the serum was observed as compared to a control) and at excretion sites of influenza (influenza virus was not observed excreted in feces or saliva from treated chickens as compared to a control). See Example 1 below.

Administration of Replikin peptides in both shrimp and chickens appears to have provided a notable measure of mucosal immunity. For example, in Example 2 of U.S. application Ser. No. 12/108,458, a mixture of Replikin peptides was administered by mouth to shrimp later challenged with taura syndrome virus. The 91% protective effect of the vaccine is expected to have been a result, at least in part, of a mucosal immune-like response in the gut of the shrimp.

Likewise, in chickens, the administration of a mixture of Replikin peptides provided a protective effect against entry of the H5N1 virus. For example, as may be seen in Example 1 below, three of six vaccinated chickens, when inoculated with H5N1 virus, produced no measurable amount of antibodies against H5N1 in their serum. Instead, the virus was apparently blocked by mucosal immunity from even entering the chickens' system. For those three chickens in which a serum immune response was measured (that is, virus did enter their system), the vaccine additionally provided a protective effect against replication of the virus in the chickens' system (no virus was excreted in the feces or saliva of the chickens). As such, mucosal immunity, in addition to other immunities, is an important aspect of the immunity imparted by Replikin-based vaccines.

Differentiation of Infectivity and Lethality in Isolates of Strains of Influenza Virus Provides Advance Information on Influenza Outbreaks One aspect of the present invention provides a method of differentiating the infectivity of a strain of virus from the lethality of the strain of virus. This double differentiation of infectivity and lethality provides advance warning of the future course of strains of influenza virus. For example, double differentiation of the infectivity and lethality in the H1N1 virus from 2004 through 2009 and the H5N1 virus from 2004 through 2008 provides advance warning of the future course of H1N1 and H5N1 (see FIGS. 2-5) and provides for the production of synthetic influenza Replikin vaccines. Synthetic influenza Replikin vaccines include vaccines such as the H5N1 vaccine described in Example 1 herein. Synthetic influenza Replikin vaccines include vaccines that comprise at least one protein, protein fragment, or peptide comprising, consisting of, homologous with, or derived from a Replikin peptide identified in a hemagglutinin protein area (the hemagglutinin protein area may be isolated from an isolate of influenza virus identified as associated with higher infectivity than another isolate of influenza virus) and/or at least one protein, protein fragment, or peptide comprising, consisting of, homologous with, or derived from a Replikin peptide identified in the pB1 gene area of an isolate of influenza virus (the pB1 gene area may be associated with higher lethality than another isolate of influenza virus).

By isolating separate influenza virus genes in silico that differentiate infectivity from lethality, the applicants have now provided a method of differentiating the infectivity and lethality of influenza viruses. The hemagglutinin protein area in influenza virus is now associated with infectivity. For example, high Replikin Counts are associated with outbreaks of various strains of influenza A virus (e.g., H1N1, H2N2, H3N2, H5N1, etc.) in the 20$^{th}$ century.

The pB1 gene area of influenza virus is likewise now associated with lethality. For example, high Replikin Counts in the pB1 gene area are associated with lethality in infections from H5N1 strains of influenza virus and low Replikin Counts in the pB1 gene area are associated with low lethality in infections from influenza. The present method for differentiating the infectivity and lethality of influenza viruses now provides both advance warning of the future course of an outbreak and a basis of production of influenza vaccines comprising synthetic Replikin peptide sequences or comprising a protein fragment, polypeptide, or peptide comprising Replikin peptide sequences or homologues of Replikin peptide sequences.

The applicants have discovered that the properties of infectivity and lethality operate with a measure of independence that is differentiable. As may be seen in FIGS. 2-5 infectivity was observed to change over time in a manner different from that observed in lethality. These data apply to both H5N1 and H1N1. For example, infectivity was observed to increase in H1N1 from 2004 through 2009 while lethality was observed to remain steady or decrease. See FIGS. 3-5. On the other hand, infectivity was observed to remain about the same in H5N1 from 2004 through 2008 while lethality was observed to increase. See FIG. 2. These data reflect the epidemiological information available for each of these strains of influenza over the measured years.

The data demonstrate that Replikin Counts in the hemagglutinin protein area of influenza shift in a manner that can be differentiated from Replikin Counts in the pB1 gene area of influenza. The data further demonstrate that infectivity and lethality are not necessarily linked in influenza viruses and are not necessarily linked in influenza viruses over time. Infectivity and lethality are likewise expected not to be linked between regions.

The results in FIGS. 2-5 and Examples 2-5 below provide a noteworthy verification of the validity and application of the software methods used to determine the concentration of Replikin peptides present in given proteins or gene areas of influenza virus and correlate with observed epidemiological properties in both the H1N1 and the H5N1 strains of influenza virus.

The data in FIG. 5 is derived from the most recent sequence data available on PubMed. A review of the data in FIG. 5 reveals that H1N1 infectivity is predicted to remain high in humans in the immediate future and H1N1 lethality is predicted to remain low in humans for the immediate future. The initial increase in H1N1 lethality in 2005 may be related to an initial high lethality observed in the first cases in the outbreak of H1N1 in or near Mexico in the spring of 2009. This increase in Replikin Count was not sustained, however, as may be seen from the Replikin Count data from 2006 through 2009. In agreement with this data, the mortality rate of subsequent cases has been observed to decline.

A review of FIGS. 2-5 likewise reveals a differentiable pattern of change in infectivity and lethality. As may be seen from the trend in FIG. 2, H5N1 lethality is predicted to continue increasing. Nonetheless, infectivity does not appear to increase in the immediate future. The data suggest that neither H1N1 in FIGS. 3-5 nor H5N1 in FIG. 2 are becoming quiescent. The data from H1N1 in FIGS. 3-5 and for H5N1 in FIG. 2 are different than data for H2N2 influenza virus and for SARS coronavirus. In H2N2 and SARS coronavirus, a decrease in Replikin Count in these infectious agents was followed by an observed quiescence in their respective infectivity and lethality. See, e.g., U.S. application Ser. No. 10/860, 050, filed Jun. 4, 2004 (paragraph 143) and U.S. application Ser. No. 12/010,027, filed Jan. 18, 2008 (paragraph 163).

It has not previously been possible to correlate virus structures with virus outbreaks, let alone to predict an outbreak six to twelve months ahead of its occurrence. Such a correlation was first retrospectively demonstrated by the applicants monitoring Replikin Counts of whole viruses and correlating these Replikin Counts with outbreaks and pandemics of common influenza strains that occurred over the past century. The applicants then isolated in silico, a Replikin Peak Gene in the pB1 gene area of the genome of influenza virus. The Replikin Peak Gene provided advance warning of H5N1 outbreaks over the past ten years, provided advance warning of an increase in human mortality from H5N1 infection, and advance warning that the increase in human mortality would occur in Indonesia.

Additionally, in 2008, while attention was focused on H5N1 as a possible pandemic agent, analysis by the applicants of H1N1 sequences using FluForecast® software (Replikins, Ltd. Boston, Mass.) warned of the coming of an H1N1 influenza outbreak. In April of 2009, the first reports of an outbreak of H1N1 influenza (which would eventually spread globally) were received from Mexico.

Presently, the higher infectivity and lower lethality of the 2009 global outbreak of H1N1 is tracked by relatively higher Replikin Counts in the hemagglutinin protein area of isolates of H1N1 and relatively lower and decreasing Replikin Counts in the pB1 gene area of isolates of H1N1. See FIG. 5 and Table 7 below.

Likewise, the lower infectivity and higher lethality of current cases of H5N1 globally are tracked by relatively lower Replikin Counts in the hemagglutinin protein area of isolates of H5N1 and relatively higher and increasing Replikin Counts in the pB1 gene area of isolates of H5N1. See FIG. 2 and Table 3 below.

Increasing Human H1N1 Lethality Gene Replikin Count as of Jun. 8, 2009 and Sep. 23, 2009

In April 2008, the applicants analyzed genomic information for isolates of H1N1 influenza virus available at www.pubmed.com using FluForecast® software (Replikins, Ltd., Boston, Mass., USA) to determine Replikin Counts for individual isolates in the hemagglutinin protein area and pB1 gene areas. The applicants also determined the mean annual Replikin Count for the hemagglutinin protein area and pB1 gene area. The applicants noted a significant increase in the Replikin Count of H1N1 isolates and on Apr. 7, 2008 predicted an increased likelihood of outbreak and warned in a published press release that the H1N1 had now become a likely candidate for the influenza strain that would cause the next pandemic of influenza. The predicted outbreak was in fact observed in the spring of 2009. In May 2009, the applicants again analyzed genomic information for isolates of H1N1 influenza virus and noted that the Replikin Count of hemagglutinin protein areas in isolates of H1N1 was continuing to rise. See Example 3, Table 4, and FIG. 3. Based on this evidence and the teachings herein, the applicants predicted that the 2009 outbreak would continue as a highly infective outbreak and that H1N1 infections should be expected to be above seasonal norms in the summer of 2009 in the Northern Hemisphere. In June 2009, the World Health Organization declared the 2009 H1N1 outbreak a global pandemic and throughout the summer continued expansion of the pandemic was reported in northern countries such as Japan, China, the U.K, and the U.S.

The applicants have now analyzed genomic information for isolates of H1N1 influenza virus through Sep. 23, 2009. In their analysis, the applicants have revealed that the Replikin Count of the Infectivity Gene in H1N1 (white in FIG. 5) remains elevated, decreasing only 3% in its mean since the high in April 2009. These high means provide no significant sign, as yet, of abatement in the current pandemic. The applicants have further revealed that the H1N1 Lethality Gene (black in FIG. 5), despite some activity, has not increased significantly in Replikin Count between 2001 and 2008. This absence of a significant increase in Replikin Count in the Lethality Gene is in contrast to the large increases seen in the Infectivity Gene between 2001 and 2008.

Concerning the pB1 gene area, the applicants note that the Standard Deviation of the Mean (SD) (represented by capped lines in FIG. 5) increased five-fold between 2001 and December 2008. The applicants further note that the Standard Deviation of the Mean increased forty-five fold between 2001 and April 2009. This increase in standard deviation of the mean Replikin Count indicates that some viruses in the H1N1 population are engaging in high replication rates and higher lethality.

As may be seen in FIG. 5, Replikin Count in the pB1 gene area of H1N1 has gradually decreased by 38% from its high in April 2009 through to Sep. 23, 2009 ($p<0.001$). Nevertheless, the mean Replikin Count remains 15% higher and the standard deviation of the mean remains nineteen times greater than the level of Replikin Count seen in 2001. These higher Replikin Counts indicate that there are still individual active viruses within the currently circulating H1N1 virus population that contain increased Replikin Counts in their Lethality Genes. The overall trend seen in FIG. 5 since April 2009, nevertheless, is clearly toward a return to the lower "resting" Replikin Count of about two, which predominated from 1980 to 2008 (or less than two, which predominated from 1934 to 1979). See Table 8 below. These low Replikin Counts from 1934 to 2008 were accompanied by low clinical H1N1 lethality.

Reproducibility of Replikin Counts in H1N1

Mean Replikin Counts in a wide range of viruses and organisms have been correlated with rapid replication and virulence. See, e.g., U.S. application Ser. No. 12/010,027, filed Jan. 18, 2008. The data in FIGS. 2-5 contribute to the evidence in support of this Replikin Count phenomenon. In addition, the data in FIGS. 2-5 provide unmistakable evidence of the reproducibility of the Replikin analysis as it correlates with rapid replication, infectivity, and lethality in viruses and organisms. This reproducibility is particularly evident in FIG. 5 where data is provided for many specific days between April and September of 2009.

As described in Example 5 below, data in FIG. 5 was gathered on a frequent (sometimes daily) basis between April 2009 and September 2009. The consistent reproducibility of the Replikin Count in the hemagglutinin and pB1 gene areas over that time demonstrates measurable trends in changes in Replikin Count such that the progression of the outbreak and pandemic has been quantitatively observed. As may be seen in FIG. 5, these quantitative observations in concert with clinical data from the CDC and WHO provide further evidence of the quantitative accuracy of Replikin Counts in viruses such as influenza. The observations and clinical data also provide evidence of the ability of the Replikin algorithm to identify clinical changes in a pathogenic population.

Synthetic Replikin Vaccine Against H1N1 and H5N2 and Other Influenza Strains of Virus The differentiation of infectivity and lethality in the influenza virus genome through the identification of concentrations of Replikin sequences in those gene areas that correlate independently with infectivity and lethality (hemagglutinin and pB1 gene area, respectively) provides a system for attacking both the mechanics of infectivity and the mechanics of lethality in influenza in one anti-virus therapy. In view of this new understanding, the applicants have created synthetic Replikin vaccines based on homologues of conserved Replikin sequences identified in the hemagglutinin protein area and homologues of conserved Replikin sequence identified in the pB1 gene area of influenza.

One vaccine was initially engineered from sequences identified in the Low-Path H5N1 isolated from the black duck in North Carolina, USA and confirmed to be conserved in both Low-Path and High-Path H5N1 strains as well as across influenza strains with conservation particularly noted in the key amino acid residues of the Replikin sequence, namely, lysine and histidine amino acid residues. The vaccine was designed to deliver an approximately equal-parts-by-weight mixture of twelve Replikin peptides to the immune system of an animal or human. Six of the peptides were isolated in silico from the hemagglutinin protein area and six of the peptides were isolated in silico from the pB1 gene area. All twelve peptides were then synthesized, and combined in a vaccine.

As described in Example 1 below, a vaccine has now successfully protected chickens from low-pathogenic H5N1 infection and has successfully blocked excretion of low-pathogenic H5N1 virus from infected chickens. The vaccine was developed from influenza Replikin peptides shared between influenza strains and conserved for decades within influenza strains and was engineered as a mixture of twelve Replikin peptides identified as expressed from the genome of H5N1 virus. Six of the Replikin peptides were synthesized according to sequences isolated from the hemagglutinin protein area of H5N1, which is involved in attachment and entry of influenza virus into a cell. Six of the Replikin peptides were synthesized according to sequences isolated from the pB1 gene area of H5N1, which has been identified as involved in replication of influenza virus in a host cell.

Another exemplary vaccine has been designed from sequences identified as conserved in H1N1 isolates. The sequences are likewise conserved across strains with conservation particularly noted in the key amino acid residues of the Replikin sequence, namely, lysine and histidine amino acid residues. The vaccine was designed to deliver an approximately equal-parts-by-weight mixture of eight Replikin peptides to the immune system of an animal or human. All eight peptides are synthesized, and combined in a vaccine.

The peptide mixture may be administered in any manner known to one of skill in the art including with a pharmaceutically acceptable carrier. Administration may be intraocularly, intranasally, transdermally, intramuscularly, or via any method of administration known now or hereafter to one of skill in the art. Because the vaccine is based on influenza Replikin peptides shared between influenza strains and conserved for decades within influenza strains, the vaccine may be administered as a therapy against infection by any influenza virus infection harboring conserved Replikin peptides sharing homology with at least one peptide of the vaccine. Such strains include any strain of influenza A, B, or C. The vaccine may be administered, for example, against H1N1, H1N2, H2N2, H3N2, H3N8, H5N1, H5N2, H7N7, H7N2, H7N3, H9N2, or H10N7 strains of influenza virus. The vaccine may be further administered against H5N1, H5N2, H3N2, H9N2, or H1N1.

Therapies Against Possible Combination of H1N1 and H5N1

In both H1N1 and H5N1, the applicants have observed that Replikin sequences are distributed unevenly throughout the genome. Instead of an even distribution, Replikin sequences are concentrated in two regions of the genome, the hemagglutinin protein area and the pB1 gene area. These gene areas are associated with infectivity and lethality, respectively, in H1N1 as well as H5N1 and other influenza strains. Clinically, H1N1 is known to have high infectivity and low lethality in 2009 while H5N1 is known to have low infectivity and high lethality (for example, H5N1 lethality in humans has reached 80% in recent outbreaks).

FIGS. 2-5 provide examples of the association of Replikin Count in hemagglutinin with infectivity and Replikin Count in the pB1 gene area with lethality. The principle that Replikin Count in a genome could be associated with lethality has been quantitatively measured in a predictive study of the relative lethality of four strains of Taura Syndrome virus. See U.S. application Ser. No. 12/010,027, filed Jan. 18, 2008. The applicability of this principle to antiviral therapies was demonstrated when Taura Syndrome virus was blocked by a specific synthetic Replikin sequence vaccine, protecting 91% of challenged shrimp from pathogenic mortality. In another example, an increase in the lethality of H5N1 in human cases in 2007 and 2008 was predicted in advance by the strain-specific Replikin Count of the Lethality Gene of H5N1. See id. Similarly, by comparing the Replikin Counts of the pB1 gene area of H5N1 Genes in eight Asian countries in 2006, the geographic site which would be first and worst struck in 2007 was correctly predicted as Indonesia. See id.

Because of the known ability of segments of the genomic sequences to transfer between influenza strains, public health officials are concerned about a possibility that the high infectivity of H1N1 might be combined with the high lethality of H5N1. At present, there is apparently no method available to predict the probability of this occurrence. Nevertheless, to prepare in advance for the possibility of an H1N1-H5N1 combination, the applicants have developed a synthetic Replikin sequence vaccine based on Replikin structures shared in the common Influenza A strains.

Example 1

Synthetic Replikin Vaccines Block H5N1 in Chickens

A synthetic Replikin vaccine containing an approximately equal-parts-by-weight mixture of twelve H5N1 Replikin peptides was tested in chickens against a low pathogenic strain of H5N1 isolated from a black duck in North Carolina, USA. Low-Path H5N1 strains infect migratory birds and impair health and productivity of commercial flocks of U.S. chickens, usually with little mortality in the commercial flocks. These Low-Path H5N1 strains are very closely related in virus structure to their more lethal High-Path H5N1 relatives in Eurasia. A mutation from a Low-Path to a High-Path strain has so far not been observed but mutations of this type over time may be expected by one of skill in the art.

The tested vaccine was engineered from sequences identified in the Low-Path H5N1 and confirmed to be conserved in both Low-Path and High-Path H5N1 strains over decades as well as across influenza strains with conservation particularly noted in the key amino acid residues of the Replikin sequence, namely, lysine and histidine amino acid residues. The tested vaccine was engineered to block both the entry site of H5N1 virus and the replication site of those H5N1 viruses that manage to enter into host cells. As such, the vaccine is called the TWO-PUNCH vaccine. As demonstrated below, evidence from the described test of the TWO-PUNCH vaccine in chickens suggests that both mechanisms for which the vaccine was designed were effective: (1) virus entry into inoculated chickens was diminished by immunity from the vaccine and (2) virus replication within infected cells was sufficiently limited by immunity from the vaccine to block excretion of the virus in feces of tested birds.

The vaccine comprises a mixture of twelve Replikin peptides. Six of the Replikin peptides are synthesized according to sequences isolated from the hemagglutinin protein area of H5N1, which is involved in attachment and entry of influenza virus into a cell. Six of the Replikin peptides are synthesized according to sequences isolated from the pB1 gene area of H5N1, which has been identified as involved in replication of influenza virus in a host cell.

The following six Replikin sequences contained in the vaccine were isolated from the hemagglutinin protein area:

```
(1) HAQDILEKEHNGKLCSLKGVRPLILK;        (SEQ ID NO: 1)

(2) KEHNGKLCSLKGVRPLILK;               (SEQ ID NO: 2)

(3) KKNNAYPTIKRTYNNTNVEDLLIIWGIHH;     (SEQ ID NO: 3)

(4) HHSNEQGSGYAADKESTQKAIDGITNK;       (SEQ ID NO: 4)

(5) HDSNVKNLYDKVRLQLRDNAK;             (SEQ ID NO: 5)
and (6) KVRLQLRDNAKELGNGCFEFYH.            (SEQ ID NO: 6)
```

The following six Replikin sequences contained in the vaccine were isolated from the pB1 gene area:

```
                                       (SEQ ID NO: 7)
    (1) KDVMESMDKEEMEITTH;

(SEQ ID NO: 8)
    (2) HFQRKRRVRDNMTKK;

(SEQ ID NO: 9)
    (3) KKWSHKRTIGKKKQRLNK;

(SEQ ID NO: 10)
    (4) HKRTIGKKKQRLNK;

(SEQ ID NO: 11)
    (5) HEGIQAGVDRFYRTCKLVGINMSKKK;
and (SEQ ID NO: 12)
    (6) HSWIPKRNRSILNTSQRGILEDEQMYQKCCNLFEK.
```

The vaccine comprises an approximate equal-parts-by-weight mixture of the twelve peptides. The following peptide amounts were combined to create an initial mixture of the vaccine:

| | |
|---|---|
| HAQDILEKEHNGKLCSLKGVRPLILK (SEQ ID NO: 1) | 239.6 mg |
| KEHNGKLCSLKGVRPLILK (SEQ ID NO: 2) | 200.8 mg |
| KKNNAYPTIKRTYNNTNVEDLLIIWGIHH (SEQ ID NO: 3) | 213.0 mg |
| HHSNEQGSGYAADKESTQKAIDGITNK (SEQ ID NO: 4) | 135.6 mg |
| HDSNVKNLYDKVRLQLRDNAK (SEQ ID NO: 5) | 170.8 mg |
| KVRLQLRDNAKELGNGCFEFYH (SEQ ID NO: 6) | 188.3 mg |
| KDVMESMDKEEMEITTH (SEQ ID NO: 7) | 161.9 mg |
| HFQRKRRVRDNMTKK (SEQ ID NO: 8) | 138.3 mg |
| KKWSHKRTIGKKKQRLNK (SEQ ID NO: 9) | 217.8 mg |
| HKRTIGKKKQRLNK (SEQ ID NO: 10) | 178.0 mg |
| HEGIQAGVDRFYRTCKLVGINMSKKK (SEQ ID NO: 11) | 159.2 mg |
| HSWIPKRNRSILNTSQRGILEDEQMYQKCCNLFEK (SEQ ID NO: 12) | 233.8 mg |

The total amount of the mixture was 2237.1 mg.

The peptide mixture was then divided into three equal parts for administration of the vaccine on three different days following hatch (days 1, 7, and 28). After dissolution with water, the three equal parts were administered to individual birds in two groups of 20 birds each for a total administration on each day of 40 birds. The total amount of active peptide ingredient administered to each bird at the time of administration (either intranasally and intraocularly or via spray inhalation) was about 18.6 mg per bird per administration. The vaccine solution was administered to chickens intranasally at a first administration on day 1 after hatch, intraocularly at a second administration on day 7 after hatch, and via fine spray inhalation at a third administration on day 14 after hatch.

Chickens on the first day of life were separated into four groups with twenty chickens per group. The first group was a control group not vaccinated and not challenged with Low-Path H5N1. The second group was vaccinated and not challenged with Low-Path H5N1. The third group was vaccinated and subsequently challenged with Low-Path H5N1 on day 28 after hatch. The fourth group was not vaccinated and was challenged with Low-Path H5N1 on day 28 after hatch.

Vaccinated chickens were subject to the vaccine on days 1, 7, and 21 after hatch as described above. Challenged chickens were inoculated with Low-Path H5N1 virus in the soft palate on day 28 after hatch. Serum from selected chickens was analyzed in all groups for antibodies against the H5N1 virus on days 7, 14, and 21 following challenge (days 35, 42, and 49 after hatch). PCR for virus fecal excretion was also analyzed for all groups.

Unvaccinated control chickens demonstrated both an expected high virus entry (as indicated by a high titer of antibodies against H5N1) and an expected high virus replication (as indicated by high fecal and salival excretion of the virus detected by PCR). In contrast, the vaccinated chickens demonstrated lower virus entry (as indicated by a low titer of antibodies against H5N1 or by the observation of no antibodies against H5N1 in serum) and an absence of fecal or salival excretion of virus indicating low or no virus replication in the vaccinated chickens. The data suggest, therefore, that the virus was partially blocked on entry by the chickens' immune response to the vaccine and the limited amount of virus that did enter the chickens' system was blocked from sufficient replication in the chickens' host cells to excrete virus in the feces or saliva.

The data in Table 1 below provide the numbers of chickens tested in each of the four groups (Negative Control, Vaccinated, Vaccinated and Challenged with Low-Path H5N1, and Challenged with Low-Path H5N1 (not vaccinated)) on a particular test day and the numbers of chickens in which production of antibodies to H5N1 was detected with a serum titer.

TABLE 1

Serum Antibody Test of Low-Path H5N1
Challenge of Vaccinated Chickens

| GROUP | Day 7 (Chickens Producing Antibody to H5N1) | Day 14 (Chickens Producing Antibody to H5N1) | Day 21 (Chickens Producing Antibody to H5N1) |
|---|---|---|---|
| Negative Control | 0 of 7 | 0 of 7 | 0 of 7 |
| Vaccinated | 0 of 7 | 6 of 6 | 0 of 5 |
| Vaccinated and Challenged with Low-Path H5N1 | 1 of 7 | 3 of 6 | 2 of 7 |
| Challenged with Low-Path H5N1 | 4 of 7 | 7 of 9 | 3 of 9 |

The data in Table 2 below provide the number of chickens tested for H5N1 virus in their saliva and feces in each of the four groups (Negative Control, Vaccinated, Vaccinated and Challenged with Low-Path H5N1, and Challenged with Low-Path H5N1 (not vaccinated)) on a particular test day and the numbers of chickens in which H5N1 was detected in their feces and saliva based on PCR analysis.

TABLE 2

PCR Test for Excreted H5N1 Virus from
Low-Path H5N1 Challenge of Chickens

| GROUP | Day 7 (Chickens in which H5N1 was detected in feces and saliva) | Day 14 (Chickens in which H5N1 was detected in feces and saliva) | Day 21 (Chickens in which H5N1 was detected in feces and saliva) |
|---|---|---|---|
| Negative Control | 0 of 10 | 0 of 7 | 0 of 7 |
| Vaccinated | 0 of 10 | 0 of 7 | 0 of 7 |
| Vaccinated and Challenged with Low-Path H5N1 | 0 of 7 | 0 of 7 | 0 of 7 |
| Challenged with Low-Path H5N1 | 3 of 7 | 2 of 9 | 1 of 7 |

The data in Tables 1 and 2, demonstrate the effectiveness of the double-protective mechanism of the TWO-PUNCH vaccine. First, while several non-vaccinated chickens challenged with H5N1 excreted virus in their feces and saliva, no vaccinated chickens challenged with H5N1 excreted virus in their feces or saliva. See Table 2. These data demonstrate that the vaccine provided a protective effect against replication of the virus. Second, while four of seven unvaccinated chickens challenged with H5N1 were producing serum antibodies against H5N1 on day 7, seven of nine unvaccinated chickens challenged with H5N1 were producing serum antibodies against H5N1 on day 14, and three of nine unvaccinated chickens challenged with H5N1 were producing serum antibodies against H5N1 on day 28, only one of seven vaccinated and challenged chickens was producing serum antibodies against H5N1 on day 7, only three of six vaccinated and challenged chickens were producing serum antibodies against H5N1 on day 14, and only two of seven vaccinated and challenged chickens were producing serum antibodies against H5N1 on day 21. See Table 1. These data demonstrate that for some of the vaccinated chickens, the H5N1 virus challenge was stopped prior to entry into the chicken's system (likely by antibodies produced at the mucus membranes). These data further demonstrate that for those vaccinated and challenged chickens in which the virus entered the system (resulting in production of serum antibodies), the virus was nonetheless not excreted in feces or saliva.

As may be seen from the data in Table 1, almost all of the non-vaccinated challenged birds seroconverted (producing detectable antibody). This demonstrates infection of the non-vaccinated birds. On the other hand, only some of the vaccinated challenged birds seroconverted. Further, for those vaccinated birds that did seroconvert, the antibody titers were low. Additionally, the negative control group had no seroconversion. These data demonstrate a protective effect of the vaccine on the birds. Additionally, Table 2 demonstrates the absence of detectable influenza in the feces and saliva of vaccinated birds. That viral excretion was blocked by this influenza Replikins vaccine is particularly significant because it is generally acknowledged that the maintenance of reservoirs of H5N1 virus in flocks of migratory birds and domestic chickens in both Asia and the U.S. (and the regional spread of H5N1 virus from these reservoirs) is dependent on viral excretions picked up by neighboring chickens and birds. Regardless of the level of lethality of a strain of H5N1 virus, absent excretion of virus, there is expected to be no spread of the virus. As such, data observed from administration of the TWO-PUNCH Replikin peptide vaccine in chickens demonstrates the efficacy of the vaccine as (1) a barrier to entry of the virus, (2) a block of replication of the virus, and (3) a block of fecal spread of the virus.

In a recent peer-reviewed publication by Jackwood et al. concerning the vaccine (Avian Diseases," Publication Online: http://avdi.allenpress.com/avdionline/?request=get-abstract&doi=10.1637%2F8892-042509-ResNote.1; Hard copy Article in Press. Jul. 4, 2009), the authors conclude: "Taken together, these data indicate that a Replikin peptide vaccine specifically made against the H5N1 Black Duck/NC/674-964/06 and administered three times to the upper-respiratory tract, was capable of protecting chickens from infection and shedding of the homologous virus, which is extremely important because reduced virus shedding and transmission decreases the potential for H5 LPAI viruses to become HPAI viruses. The study is also important because it shows that the vaccine can be effectively mass delivered to the upper-respiratory tract." Id.

Because of shared sequences, the vaccine may likewise be administered against H5N2, H1N1, H9N2, H3N2 or any other influenza strain having Replikin sequences that share homology with the peptides of the vaccine.

Example 2

Differentiation of Infectivity and Lethality in H5N1 Isolates from 2004 Through 2008

The infectivity and lethality of isolates of the H5N1 influenza virus from between 2004 and 2008 was differentiated by analyzing the Replikin Counts of sequences of the hemagglutinin protein area of isolates publicly available at www.pubmed.com for the years 2004 to 2008 and the Replikin Counts of sequences of the pB1 gene area of isolates publicly available at www.pubmed.com for the years 2004 to 2008.

The Replikin Count (number of Replikin sequences per 100 amino acid residues of a sequence) of the publicly available hemagglutinin sequences and the publicly available pB1 gene area sequences were analyzed using FLUFORECAST® software (Replikins, Ltd., Boston, Mass.). The results of the analysis are provided below in Table 3.

TABLE 3

H5N1 Influenza Virus Infectivity and Lethality

| Year | Hemagglutinin Mean Annual Replikin Count (Infectivity) | Standard Deviation | Hemagglutinin Sequences Analyzed | pB1 Gene Area Mean Annual Replikin Count (Lethality) | Standard Deviation | pB1 Gene Area Sequences Analyzed |
|---|---|---|---|---|---|---|
| 2004 | 4.2 | 0.6 | 17 | 2 | 0.1 | 14 |
| 2005 | 3.8 | 0.2 | 14 | 1.8 | 0.1 | 6 |
| 2006 | 3.8 | 0.4 | 29 | 5.9 | 7.0 | 24 |
| 2007 | 4.6 | 0.5 | 27 | 12.2 | 7.9 | 33 |
| 2008 | 4.5 | 0.4 | 6 | 15.1 | 6.5 | 6 |

As may be seen from the data in Table 3 and the illustration of the data in FIG. 2, analysis of the Replikin Counts of hemagglutinin protein area sequences and pB1 gene area sequences for isolates of H5N1 from 2004 through 2008 reveal that Replikin Counts in the hemagglutinin protein area and Replikin Counts in the pB1 gene area are independent from one another in isolates from a given year and Replikin Counts in these areas of the genome trend in directions that are independent from one another. As may be observed, mean annual Replikin Counts in the pB1 gene area trended upward while mean annual Replikin Counts in the hemagglutinin protein area remained about the same.

Replikin Counts in the pB1 gene area are associated with lethality and Replikin Counts in the hemagglutinin protein area are associated with infectivity. As such, the data in Table 3 as illustrated in FIG. 2 demonstrate that lethality was increasing from 2004 through 2008 while infectivity was fairly steady. The data correlate with epidemiological data in H5N1. For example, H5N1 has continued to cause high rates of mortality in humans. The highest presently recorded lethality was predicted by the applicants following analysis of publicly available H5N1 pB1 sequences from isolates in 2005 and 2006. In 2006 the applicants predicted that mortality rates would increase in H5N1 infections in response to increasing Replikin Counts in the pB1 gene area of the virus. The Applicants further predicted that increased mortality rates would particularly affect Indonesia because Replikin Counts were notably rising in that country. As predicted, H5N1 viral infection resulted in the death of as many as 80% of infected hosts in Indonesia in 2007.

These high rates of lethality have not greatly diminished globally. In fact, the World Health Organization estimates the mortality rate of the present H5N1 outbreak at around 60%. The lethality of the virus, as such, remains high and epidemiological data agrees with the Replikin Count data illustrated in FIG. 2 in that neither set of data suggests that lethality will decrease in the near future.

The infectivity of H5N1 influenza virus has apparently remained steady over the years from 2004 through 2008 with very low rates of infection and very low rates of possible transmission between humans. In particular, because of infrequent infections in humans, the H5N1 virus produced less than 300 World Health Organization confirmed deaths over the 10 years through the spring of 2008 even though the virus killed as many as 60% of those infected. For H5N1, the high human mortality rate, in combination with a low infectivity, appear to limit the ability of H5N1 to presently produce an influenza pandemic.

Nevertheless, the data illustrated in FIG. 2 predict that H5N1 is not entering a quiescent phase but will continue with high lethality and low infectivity in the near future. This prediction of continued lethality is in contrast to previous predictions of quiescence in the H2N2 strain of influenza virus and in SARS. See U.S. application Ser. No. 10/860,050, filed Jun. 4, 2004 (paragraph 143) and U.S. application Ser. No. 12/010,027, filed Jan. 18, 2008 (paragraph 163).

Example 3

Differentiation of Infectivity and Lethality at Outset of 2009 Global Outbreak of H1N1 Influenza Virus (Spring 2009)

The infectivity and lethality of the H1N1 influenza virus causing the 2009 global outbreak of H1N1 influenza virus was differentiated by analyzing the Replikin Counts of sequences of the hemagglutinin protein area of isolates of H1N1 publicly available at www.pubmed.com for the years 2004 through the spring of 2009 and the Replikin Counts of sequences of the pB1 gene area publicly available at www.pubmed.com for the years 2004 through the spring of 2009.

The Replikin Count (number of Replikin sequences per 100 amino acid residues of a sequence) of the publicly available hemagglutinin sequences and the publicly available pB1 gene area sequence were analyzed using FLUFORECAST® software (Replikins, Ltd., Boston, Mass.). The results of the analysis are provided below in Table 4.

TABLE 4

H1N1 Influenza Virus Infectivity and Lethality

| Year | Hemagglutinin Mean Annual Replikin Count (Infectivity) | Standard Deviation | Hemagglutinin Sequences Analyzed | pB1 Gene Area Mean Annual Replikin Count (Lethality) | Standard Deviation | pB1 Gene Area Sequences Analyzed |
|---|---|---|---|---|---|---|
| 2004 | 5.3 | 1.4 | 51 | 2 | 0.0 | 1 |
| 2005 | 6.2 | 2.1 | 160 | 4.6 | 6.5 | 6 |
| 2006 | 6.2 | 1.9 | 234 | 2.2 | 0.4 | 3 |
| 2007 | 6.2 | 1.5 | 680 | 2.1 | 0.1 | 15 |
| 2008 | 7 | 0.9 | 491 | 2 | 0.0 | 25 |
| 2009 | 10 | 2.4 | 29 | 2 | 0.0 | 1 |

As may be seen from the data in Table 4 and the illustration of the data in FIG. 3, analysis of the Replikin Counts of hemagglutinin protein area sequences and the pB1 gene area sequences for isolates of H1N1 from 2004 through 2009 reveal Replikin Counts in the hemagglutinin protein area and Replikin Counts in the pB1 gene area are independent from one another in isolates from a given year and Replikin Counts in these areas of the genome trend in directions that are independent from one another. Mean Replikin Counts in the hemagglutinin protein area trended upward while mean annual Replikin Counts in the pB1 gene area stayed about the same with a noticeable spike in mean annual Replikin Count in the pB1 gene area in 2005.

Replikin Counts in the hemagglutinin protein area are associated with infectivity and Replikin Counts in the pB1 gene area are associated with lethality. As such, the data illustrated in FIG. 3 demonstrate that infectivity was on the increase from 2004 through 2009 while lethality was fairly steady with a noticeable increase around 2005. The data correlate with epidemiological data from the global 2009 outbreak of H1N1. For example, the global outbreak of the H1N1 strain of influenza virus in the spring of 2009 has been observed to have high infectivity with effective transmission from host to host and the potential for an efficient and rapid spread of the virus internationally. See www.cdc.gov/mmwr/preview/mmwrhtml/mm5817a1.htm. Despite rapid global transmission of the virus, the case-fatality rate remains low and infection by the virus generally has been observed to be mild, self-limited, and uncomplicated. Id. Nevertheless, because the H1N1 virus has not been wide-spread in the population over the past years, some cases of severe disease and death have been reported in previously healthy young adults and children. Id.

By monitoring the Replikin Count in the whole genome of H1N1 in the spring of 2008, the inventors predicted the outbreak of H1N1 in the spring of 2009, which has now become the global outbreak of 2009. In particular, a review of publicly available sequences from isolates of the H1N1 strain of influenza virus in the spring of 2008 revealed an increase in mean Replikin Count (Replikin sequences per 100 amino acids in the publicly available sequence) in the hemagglutinin protein area of isolates of H1N1 to a mean of 7.6 with a standard deviation of plus/minus 1.4. The mean Replikin Count of 7.6 represented the highest Replikin Count in H1N1 influenza virus since the 1918 H1N1 pandemic. The p value for the observation that the Replikin Count was the highest since the 1918 H1N1 pandemic was less than 0.001. The applicants noted that the increase in Replikin Count in isolates of H1N1 appeared to be specific to H1N1 in that a concurrent 80% decline in the Replikin Count of H3N2 was observed.

The applicants noted in concert with the historically high Replikin Count that H1N1 influenza virus appeared to be rapidly replicating simultaneously in the U.S. and Austria. Based on the observed-historically-high Replikin Counts, the applicants predicted that H1N1 should succeed H5N1 as the leading candidate for the next expected and overdue pandemic. The applicants noted, however, that certain virus Replikin structures detected in all three previous pandemics, namely, 1918 H1N1, 1957 H2N2, and 1968 H3N2, as well as in H5N1, had not yet been detected in the evolving H1N1 isolates in the spring of 2008. The applicants noted that the 1918 H1N1 outbreak had an estimated human mortality rate of about 2.5 to 10%. Despite this moderate mortality rate, a very high infectivity rate in the 1918 pandemic produced an estimated 50 million deaths worldwide.

The lethality of H1N1 influenza virus has apparently remained generally steady over the years from 2004 through 2009. There appears to have been a spike in lethality in Mexico, however, just at the beginning of the spring 2009 outbreak. This spike in lethality appears to have waned as the outbreak spread in Mexico and globally. This initial spike may be related to H1N1 isolates carrying a high Replikin Count in the pB1 gene area as reflected in the 2005 isolates disclosed in Table 4 above. However, as the outbreak spread, the 2005 increase in Replikin Count in the pB1 gene area was apparently lost and the mortality rate of subsequent cases also declined.

The data in Table 4, additionally predict that H1N1 is not entering a quiescent phase but will continue with high infectivity in the near future.

Example 4

Double Differentiation of Infectivity and Lethality in 2009 Global Outbreak of H1N1 Influenza Virus Through Jun. 8, 2009

The infectivity and lethality of the H1N1 influenza virus causing the 2009 global outbreak of H1N1 influenza virus was differentiated by analyzing the Replikin Counts of sequences of the hemagglutinin protein area of isolates of H1N1 publicly available at www.pubmed.com from 2001 through Jun. 8, 2009 and the Replikin Counts of sequences of the pB1 gene area publicly available at www.pubmed.com from 2001 through Jun. 8, 2009.

The Replikin Count (number of Replikin sequences per 100 amino acid residues of a sequence) of the publicly available hemagglutinin sequences and the publicly available pB1 gene area sequences were analyzed using FLUFORECAST® software (Replikins, Ltd., Boston, Mass.). The results of the analysis are provided below in Table 5.

TABLE 5

H1N1 Influenza Virus Infectivity and Lethality in Humans

| Year | Hemagglutinin Mean Annual Replikin Count (Infectivity) | Standard Deviation | Hemagglutinin Sequences Analyzed | pB1 Gene Area Mean Annual Replikin Count (Lethality) | Standard Deviation | pB1 Gene Area Sequences Analyzed |
|---|---|---|---|---|---|---|
| 2001 | 4.3 | 1.9 | 144 | 2 | 0.1 | 122 |
| 2002 | 3.5 | 1.9 | 62 | 2 | 0.1 | 4 |
| 2003 | 4.8 | 1.3 | 88 | 2 | 0.2 | 25 |
| 2004 | 3.1 | 3 | 15 | 2 | 0.1 | 6 |
| 2005 | 5.1 | 2.9 | 68 | 2.6 | 3.7 | 19 |
| 2006 | 5.6 | 1.5 | 102 | 2.1 | 0.7 | 27 |
| 2007 | 6 | 1.6 | 537 | 2.1 | 1.1 | 318 |
| 2008 | 6.7 | 1.3 | 320 | 2 | 0.2 | 41 |
| 2009 | 9.7 | 1.9 | 357 | 3.2 | 3.7 | 177 |

As may be seen from the data in Table 5 and the illustration of the data in FIG. 4, analysis of the Replikin Counts of hemagglutinin protein area sequences and the pB1 gene area sequences for isolates of H1N1 from 2001 through Jun. 8, 2009 reveal Replikin Counts in the hemagglutinin protein area and Replikin Counts in the pB1 gene area are independent from one another in isolates from a given year and Replikin Counts in these areas of the genome trend in directions that are independent from one another. As may further be seen in Table 5 and FIG. 4, mean annual Replikin Counts in the hemagglutinin protein area trended upward from 2001 through 2009 while mean annual Replikin Counts in the pB1 gene area stayed about the same with a small spike in mean annual Replikin Count in 2005 that was not statistically significant ($p<0.40$) and a notable spike in mean annual Replikin Count in 2009 that is statistically significant ($p<0.001$).

The data in Table 5 demonstrate that infectivity was on the increase from 2001 through 2009 while lethality was fairly steady through 2008. The same pattern of steady Replikin Counts related to lethality is also seen in the 2004 through May 18, 2009 data provided in Example 3 above.

An increase is additionally observed in the data from 2009 in Table 5, which demonstrate a notable increase in mean annual Replikin Count for the pB1 gene area from 2 (+/−0.2) in 2008 to 3.2 (+/−3.7) in 2009. In analyzing 836 isolates of H1N1 influenza virus isolated over the past 76 years, the applicants have observed that the Replikin Count of the pB1 gene area has generally been in the range of about two Replikin sequences per 100 amino acids for around 76 years. See Table 6. The 2008 through 2009 increase from 2 to 3.2 (with a large increase in standard deviation) represents, therefore, a notable change in the lethality of the H1N1 influenza virus.

The infectivity and lethality data for 2009 differs in Table 5 above from the data in Table 4 above in that the data in Table 5 represent the most recent genomic sequences published at www.pubmed.com as of Jun. 8, 2009. The data in Table 4 above represent a much smaller number of genomic sequences published at www.pubmed.com only through May 18, 2009.

While the data in Table 5 demonstrate an increase in mean annual Replikin Count for the pB1 gene area from 2 (+/−0.2) in 2008 to 3.2 (+/−3.7) in 2009, the data in Table 4 demonstrate a steady mean annual Replikin Count for the pB1 gene area from 2 (+/−0) in 2008 to 2 (+/−0) in 2009. As such, the increase in Replikin Count in Table 5 above, as compared to Table 4, reflects an increase in mean Replikin Count for isolates published at www.pubmed.com between May 18, 2009 and Jun. 8, 2009. This increase in Replikin Count for genomic information published over a three week period demonstrates a rise in lethality in the evolving virus. The data in Table 5, predicted that H1N1 was not entering a quiescent phase but would continue with high infectivity and possible increasing lethality in the future.

The following accession numbers disclosed in Table 6 were queried by the applicants at www.pubmed.com using FLUFORECAST® software (Replikins, Ltd., Boston, Mass.) through Jun. 8, 2009. Mean annual Replikin Count, standard deviation, and statistical p-values for each year are reported. The Replikin Counts from these accession numbers are generally reflected in the data in Table 5 and FIG. 4.

TABLE 6

H1N1 Annual Mean Replikin Count

| Year | PubMed Accession Number-Replikin Count | No. of Isolates per year | Mean Replikin Count per year | S.D. | Significance |
|---|---|---|---|---|---|
| 1933 | ABD77804; ACF54606; ABF47963 | 3 | 2.4 | 0.0 | low $p<.001$ |
| 1934 | ACF41842; ABD77683 | 2 | 1.6 | 0.0 | low $p<.001$, prev $p<.001$ |
| 1935 | ABD62789; ABO38392; ABN59420 | 3 | 1.6 | 0.2 | low $p<.20$, prev $p>.50$ |
| 1936 | ABO38359 | 1 | 1.5 | 0.0 | prev $p<.20$ |
| 1940 | ABI20834 | 1 | 1.5 | 0.0 | |
| 1942 | ABD62850 | 1 | 1.2 | 0.0 | |
| 1943 | ABD79109; ABO38381; ABO38062 | 3 | 1.5 | 0.0 | low $p>.50$, prev $p<.001$ |

TABLE 6-continued

H1N1 Annual Mean Replikin Count

| Year | PubMed Accession Number-Replikin Count | No. of Isolates per year | Mean Replikin Count per year | S.D. | Significance |
|---|---|---|---|---|---|
| 1945 | ABP49335 | 1 | 1.5 | 0.0 | prev p > .50 |
| 1946 | ABD79120 | 1 | 1.5 | 0.0 | |
| 1947 | ABD77815 | 1 | 1.5 | 0.0 | |
| 1948 | ABN59409 | 1 | 1.6 | 0.0 | |
| 1949 | ABN59442 | 1 | 1.6 | 0.0 | |
| 1950 | ABD61743; ABP49324 | 2 | 1.6 | 0.0 | low p < .001 |
| 1951 | ABR15816; ABQ44479; ABQ01319; ABP49489 | 4 | 1.6 | 0.0 | low p < .001 |
| 1954 | ABD60974; ABO52288 | 2 | 1.5 | 0.0 | prev p < .001 |
| 1957 | ABD15267 | 1 | 1.6 | 0.0 | prev p < .001 |
| 1976 | ACQ99829; ABV45846; ABQ44402 | 3 | 1.9 | 0.2 | low p < .02, prev p < .05 |
| 1977 | ABD95358; ABD60952; ABD60941; ABO44142 | 4 | 1.5 | 0.1 | low p < .30, prev p < .002 |
| 1978 | ABY81357; ABP49456; ABP49346; ABO38073; ABO33000; ABO32989; ABN59431; ABK79956; ABG26821; ABF47745; ABF4; 7734; ABF47723; ABF47712; ABF47701 | 14 | 1.4 | 0.3 | low p < .40, prev p < .20 |
| 1979 | ABW36319; ABQ01330; ABN50764 | 3 | 1.8 | 0.0 | low p < .001, prev p < .001 |
| 1980 | ABO38370; ABO33017; ABF47756; | 3 | 2.0 | 0.0 | low p < .001, prev p < .001 |
| 1981 | ABO52266 | 1 | 2.0 | 0.0 | prev p > .50 |
| 1982 | ABD95347; ABD77826; ABO52805 | 3 | 2.2 | 0.2 | low p < .02, prev p < .10 |
| 1983 | ABW91193; ABO38348; ABO37996; ABO33033; ABN50925; ABN50908; ABM66894; ABM66916; ABM66905; ABM22243; ABM22232; ABM22221; ABM22210; ABM22199; ABM22188; ABM22177; ABM22166; ABL67272; ABL67261; ABK80055; ABK80044; ABK80033; ABK40609; ABK40598; ABK40587; ABK40576; ABK40565; ABK40554; ABK40543; ABK40518; ABI92310; ABI30386; ABI20867; ABG88352; ABG88341; ABF47833; ABF47778; ABG79960; ABF47855; ABF47844; ABF47767; ABF47800; ABG26843; ABG26832; ABF47822; ABF47811; ABF47789 | 47 | 2.0 | 0.1 | low p < .001, prev p < .05 |
| 1984 | ABP49357; ABO38414 | 2 | 2.0 | 0.0 | low p < .001, prev p < .04 |
| 1986 | P03430; P03431; ABP49368; ABO44131; ABO38403; ABM22254; P03427 | 7 | 2.0 | 0.3 | low p < .001, prev p > .50 |
| 1987 | ABQ44424; ABN50948; ABN50936 | 3 | 2.0 | 0.0 | low p < .001, prev p > .50 |
| 1988 | ABU80408 | 1 | 2.1 | 0.0 | prev p < .001 |
| 1989 | ACL12269; ACK99451 | 2 | 2.0 | 0.0 | low p < .001, prev p < .001 |
| 1990 | P16512; P16510; P16514; P18882; P16502 | 5 | 2.1 | 0.4 | low p < .02, prev p > .50 |
| 1991 | ABD60963; ACQ84485; ACF41941; ACF41930 | 4 | 1.9 | 0.2 | low p < .02, prev p < .30 |
| 1993 | NP_040985; AAA43643; AAA43641; AAA43640; AAA43639; AAA43582; AAA43581 | 7 | 2.1 | 0.4 | low p < .002, prev p < .20 |
| 1995 | ACK99473; ACF41875; ABG88330; ABG26799; ABF47646; ABJ53446; ABI92321; ABI30375; ABI20878; ABI20845; ABG88319; ABG88308; ABF47635; ABG47848; ABG26788; ABF47613; ABE26999; ABE12040; ABE11968; ABE11930; ABE11908; ABE11897; ABE11886; ABE11875 | 24 | 2.0 | 0.1 | low p < .001, prev p < .30 |
| 1996 | ABO52233; ABO38018; ABN51074; ABN50981; ABN50970; ABN50959; ABF47657; ABM22298; ABM22287; ABM22276; ABM22265; ABJ53512; ABJ53501; ABI95291; ABI95280; ABI95269; ABI95258; ABI93036; ABI21582; ABI21571; ABI21560; ABI21549; ABI21538; ABI21527; ABI20856; ABG47837; ABF47668 | 27 | 2.0 | 0.1 | low p < .001, prev p > .50 |
| 1999 | ACR15312; ACF41886; ABK40014; ABJ16617 | 4 | 2.1 | 0.3 | low p < .01, prev p < .20 |
| 2000 | Q82571; AAF99677; AAF99676; AAX56539; ABV45857; ABU80317; ABU80306; ABS49995; ABS49984; ABR28809; ABR28787 ABR28776; ABR15926; ABR15915; ABR15904; ABR15893; ABP49390; ABP49313; ABP49225; ABO44054; ABM22034; ABL67217; ABL67195; ABK79978; ABK40058; ABK40047; ABK40036; ABJ53523; ABJ53457; ABJ16738; ABJ16727; ABJ16650; ABJ09335; ABI95302; ABI95225; ABG88561; ABG88550; ABG80191; ABG80180; ABG67488; ABG48057; ABG37370; ABF47899; ABF47888; ABF47877; ABG47826; ABG47815; ABE11676; ABE11665; ABD95039; ABD95028; ABD95017; ABD95006; ABD94995 ABD94984; ABD94973; ABD94764; ABD78046; ABD78035; ABD78024; ABD78013; ABD78002; ABD77991; ABD77980; ABD77969; ABD77958; ABD77947; ABD77936; ABD77925; ABD77738; ABD77727; ABD77716; ABD63071; ABD61548; ABD61526; ABD60908; | 82 | 2.0 | 0.1 | low p < .001, prev p < .40 |

TABLE 6-continued

H1N1 Annual Mean Replikin Count

| Year | PubMed Accession Number-Replikin Count | No. of Isolates per year | Mean Replik TABLE 6-continued H1N1 Annual Mean Replikin Count

| Year | PubMed Accession Number-Replikin Count | No. of Isolates per year | Mean Replikin Count per year | S.D. | Significance |
|---|---|---|---|---|---|
| | ABW40617; ABW40606; ABW40584; ABW40573; ABW40562; ABW40551; ABW40540; ABW40529; ABW40518; ABW40507; ABW40496; ABW40485; ABW40474; ABW40463; ABW40452; ABW40441; ABW40430; ABW40419; ABW40408; ABW40397; ABW40375; ABW40364; ABW40353; ABW40342; ABW40320; ABW40309; ABW40298; ABW40287; ABW40265; ABW40243; ABW40232; ABW40221; ABW40210; ABW40188; ABW40166; ABW40155; ABW40133; ABW40122; ABW40111; ABW40100; ABW40078; ABW40067; ABW40056; ABW40045; ABW40023; ABW40012; ABW40001; ABW39990; ABW39979; ABW39968; ABW39957; ABW39935; ABW39924; ABW39913; ABW39902; ABW39891; ABW39869; ABW39858; ABW39847; ABW39836; ABW39825; ABW39814; ABW39785; ABW36308; ABW36297; ABW36286; ABW36275; ABW36264; ABW36253; ABW36242; ABW36231; ABW36220; ABW36209; ABW36198; ABW36187; ABV82559; ABV45967; ABV45956; ABV45945; ABV45934; ABV45923; ABV45901; ABV45890; ABV45879; ABV30632; ABV30621; ABV30610; ABV30599; ABV30588; ABV30577; ABV30566; ABV30555; ABV30544; ABV30533; ABV30511; ABV30500; ABV30467; ABV30379; ABV30368; ABV30357; ABV30346; ABV30335; ABV30324; ABV30313; ABV30302; ABV30291; ABV30203; ABV30192; ABV30181; ABV30170; ABV30159; ABV30148; ABV30137; ABV30115; ABV30104; ABV30093; ABV30060; ABV30049; ABV30038; ABV30027; ABV30016; ABV30005; ABV29994; ABV29983; ABV29972; ABV29961; ABV29950; ABV29928; ABV29895; ABV29884; ABV29873; ABV29862; ABV29851; ABV29840; ABV29807; ABV29796; ABV29785; ABV29774; ABV29763; ABV29752; ABV29741; ABV29708; ABV29697; ABV29686; ABV29675; ABV29664; ABV29653; ABV29642; ABV29620; ABV29609; ABV29587; ABV29576; ACN72614; ACR61674; ACR61663; P0C574; Q20MH0; Q1WP00; ABS00328; Q8JSD9 | | | | |
| 2008 | ACP20229; ACP20218; ABV01075; ACR15521; ACR15510; ACR15499; ACR15488; ACR15477; ACR15466; ACR15455; ACR15444; ACR15433; ACR15378; ACR15367; ACR15345; ACR15279; ACR15268; ACR15246; ACQ65766; ACP44233; ACP44222; ACP44211; ACP44200; ACO95423; ACO95412; ACO95401; ACO95390; ACO95379; ACO94878; ACO94867; ACO94713; ACO36405; ACN33153; ACN33131; ACN32520; ACN32509; ACL12159; ACI26447; ACF54595; ABV01079; ABV01076; ABV01074; ABV01073; ABV01070; ABV01069; ABV01068; ACR58560; ACR58549 | 49 | 2.0 | 0.2 | low p < .001, prev p < .04 |
| 2009 | A4GCI3; A4GCK5; A4GBY5; B3EUR4; Q0HD52; ACP41103; ACR47013; ACR08608; ACR55002; ACR08503; ACR09394; ACR09393; ACR09392; ACR09391; ACR08590; ACR08588; ACR08586; ACR08585; ACQ99679; ACQ99678; ACQ99677; ACQ99676; ACQ99675; ACQ83306; ACQ76409; ACQ76378; ACQ76372; ACQ76357; ACQ76349; ACQ76320; ACQ76306; ACQ76296; ACQ76289; ACQ63280; ACQ63255; ACQ63247; ACQ63231; ACQ55362; ACP44176; ACP44169; ACP44165; ACP41958; ACP41941; ACP41933; ACR46669; ACR46660; ACR20067; ACR78576; ACR67252; ACR67242; ACR54992; ACR54982; ACR54972; ACR54962; ACR52496; ACR52486; ACR52476; ACR52466; ACR52456; ACR52446; ACR52436; ACR52426; ACR52416; ACR39501; ACR39461; ACR52396; ACR52386; ACR52376; ACR51073; ACR51063; ACR51053; ACR51043; ACR51033; ACR51023; ACR51013; ACR51003; ACR40306; ACR40396; ACR40386; ACR40376; ACR40366; ACR40356; ACR40346; ACR40336; ACR40326; ACR40316; ACR40296; ACR39491; ACR39481; ACR39471; ACR39451; ACR39441; ACR39431; ACR39421; ACR39411; ACR39401; ACR39362; ACR38881; ACR18922; ACR15356; ACR10219; ACR10218; ACR10194; ACR08589; ACR08587; ACR08584; ACQ84475; ACQ84465; ACR08467; ACR08457; ACR08447; ACR08437; ACR08427; ACQ73409; ACQ73411; ACQ73410; ACQ89953; ACQ89952; ACQ89951; ACQ89950; ACQ89949; ACQ89948; ACO94845; ACO94834; ACR54044; ACR49313; ACR49312; ACR49311; ACR49310; ACR49309; ACR49308; ACR49307; ACR49306; ACR49305; ACR15750; ACR15613; ACR77506; ACR77496; ACR77486; ACR77476; ACR77466; ACR77456; ACR77446; ACR67121; ACR67120; ACR67119; ACR67118; ACR56458; ACR56448; ACR56438; ACR56428; ACR56418; ACR56408; ACR56398; ACR56388; ACR38797; ACR38796; ACR38795; ACR78469; ACR54049; A4GCI4; | 177 | 3.2 | 3.7 | low p < .001, prev p < .001 |

TABLE 6-continued

H1N1 Annual Mean Replikin Count

| Year | PubMed Accession Number-Replikin Count | No. of Isolates per year | Mean Replikin Count per year | S.D. | Significance |
|---|---|---|---|---|---|
| | A4GCK6; A4GBY6; B3EUR5; Q0HD51; A3DRP9; A8C8X2; A4K152; A4U7B5; A4U6W1; A4GCL7; A4GCJ5; A4GCM8; A8C8K3; B4URE5; Q289L8; Q07FH6 | | | | |

Example 5

Double Differentiation of Infectivity and Lethality in 2009 Global Outbreak of H1N1 Influenza Virus Through Sep. 23, 2009

The infectivity and lethality of the H1N1 influenza virus causing the 2009 global outbreak of H1N1 influenza virus was differentiated by analyzing the Replikin Counts of sequences of the hemagglutinin protein area and pB1 gene area of isolates of H1N1 publicly available at www.pubmed.com from 2001 through Sep. 23, 2009.

The Replikin Count (number of Replikin sequences per 100 amino acid residues of a sequence) of the publicly available hemagglutinin sequences and the publicly available pB1 gene area sequences were analyzed using FLUFORECAST® software (Replikins, Ltd., Boston, Mass.). The results of the analysis are provided below in Table 7.

TABLE 7

H1N1 Influenza Virus Infectivity and Lethality in Humans
1 Jan. 2001 through 23 Sep. 2009

| Date | Hemagglutinin Mean Annual Replikin Count (Infectivity) | Standard Deviation | Hemagglutinin Sequences Analyzed | pB1 Gene Area Mean Annual Replikin Count (Lethality) | Standard Deviation | pB1 Gene Area Sequences Analyzed |
|---|---|---|---|---|---|---|
| 2001 | 4.3 | 2 | 144 | 2 | 0.1 | 122 |
| 2002 | 3.5 | 1.9 | 62 | 2 | 0.1 | 4 |
| 2003 | 4.8 | 1.3 | 88 | 2 | 0 | 25 |
| 2004 | 5 | 3.1 | 15 | 2 | 0 | 6 |
| 2005 | 5.2 | 2.7 | 68 | 1.8 | 0.4 | 19 |
| 2006 | 5 | 2.3 | 102 | 2.2 | 0.7 | 27 |
| 2007 | 6 | 1.6 | 537 | 2.1 | 1.1 | 318 |
| 30 JUN. 2008 | 6.7 | 1.2 | 320 | 2 | 0.2 | 41 |
| 31 DEC. 2008 | 7 | 1.3 | 491 | 2 | 0.5 | 118 |
| 30 APR. 2009 | 10 | 2.4 | 29 | 3.7 | 4.5 | 155 |
| 6 JUN. 2009 | 9.7 | 2.4 | 357 | 3.3 | 4 | |
| 13 JUN. 2009 | 10 | 1.9 | | 3 | 3.6 | |
| 15 JUN. 2009 | 9.7 | 2.4 | | 3 | 3.5 | |
| 16 JUN. 2009 | 9.7 | 1.8 | | 3 | 3.5 | 203 |
| 20 JUN. 2009 | 9.8 | 1.8 | 415 | 3 | 3.5 | 203 |
| 21 JUN. 2009 | 9.8 | 1.8 | 425 | 3 | 3.5 | 254 |
| 23 JUN. 2009 | 9.8 | 1.8 | 425 | 2.8 | 3.2 | 209 |
| 26 JUN. 2009 | 9.9 | 1.8 | 532 | 3 | 3.5 | 226 |
| 29 JUN. 2009 | 9.9 | 1.6 | 553 | 2.9 | 3.3 | 226 |
| 30 JUN. 2009 | 9.9 | 1.6 | 553 | 2.9 | 3.3 | 230 |
| 2 JUL. 2009 | 9.9 | 1.6 | 559 | 2.6 | 2.8 | 231 |
| 4 JUL. 2009 | 10 | 1.6 | 563 | 2.9 | 3.3 | 223 |
| 6 JUL. 2009 | 10 | 1.6 | 519 | 2.9 | 3.3 | 222 |
| 8 JUL. 2009 | 10 | 1.6 | 585 | 2.9 | 3.4 | 254 |
| 10 JUL. 2009 | 9.6 | 1.3 | 627 | 2.7 | 3 | 254 |
| 12 JUL. 2009 | 9.6 | 2.2 | 627 | 2.8 | 3.2 | 265 |
| 14 JUL. 2009 | 9.6 | 2.1 | 652 | 2.8 | 3.2 | 261 |
| 18 JUL. 2009 | 9.6 | 2.1 | 652 | 2.8 | 3.1 | 275 |
| 22 JUL. 2009 | 9.6 | 2.1 | 654 | 2.7 | 3 | 295 |
| 24 JUL. 2009 | 9.7 | 2.1 | 654 | 2.7 | 3.1 | 295 |
| 25 JUL. 2009 | 9.7 | 2.1 | 683 | 2.7 | 3 | 326 |
| 3 AUG. 2009 | 9.6 | 2.1 | 747 | 2.6 | 2.8 | 319 |
| 6 AUG. 2009 | 9 | 2.8 | 820 | 2.6 | 2.8 | 345 |
| 8 AUG. 2009 | 9 | 2.8 | 820 | 2.6 | 2.7 | 340 |
| 10 AUG. 2009 | 9.6 | 2.1 | 771 | 2.6 | 2.7 | 345 |
| 12 AUG. 2009 | 9.6 | 2.1 | 777 | 2.6 | 2.7 | 373 |
| 14 AUG. 2009 | 9.6 | 2.1 | 804 | 2.5 | 2.6 | 373 |
| 15 AUG. 2009 | 9.6 | 2.1 | 812 | 2.5 | 2.6 | 373 |
| 16 AUG. 2009 | 9.5 | 2.1 | 803 | 2.5 | 2.6 | 373 |
| 17 AUG. 2009 | 9.5 | 2.1 | 812 | 2.5 | 2.6 | 373 |
| 18 AUG. 2009 | 9.6 | 2.1 | 812 | 2.5 | 2.6 | 371 |
| 20 AUG. 2009 | 9.6 | 2.1 | 810 | 2.1 | 2.7 | 376 |
| 22 AUG. 2009 | 9.6 | 2.1 | 817 | 2.5 | 2.6 | 378 |

TABLE 7-continued

H1N1 Influenza Virus Infectivity and Lethality in Humans
1 Jan. 2001 through 23 Sep. 2009

| Date | Hemagglutinin Mean Annual Repl by a high level of infections throughout the 2009 summer in the U.S., U.K., China and many other Northern Hemisphere countries. The pandemic also continued unabated in the Southern Hemisphere in its 2009 winter season.

As may be seen from FIG. 5, a peak in Replikin Count in both the hemagglutinin protein area and in the pB1 gene area is observed between December 2008 and April 2009. As would be expected with peaks in Replikin Count, the December 2008 to April 2009 peak was followed (two to six months later) in the U.S. by a peak in pediatric deaths in June of 2009. See CDC FluView, Week 36 ending Sep. 12, 2009 available at http://www.cdc.gov/flu/weekly/. To our knowledge, prior to the discovery of Replikin sequences, no virus structure had been reported that quantitatively correlated with or predicted virus outbreaks or the clinical course of virus outbreaks. FIG. 5 demonstrates a quantitative correlation with and prediction of both outbreaks and their clinical course.

FIG. 5 shows that for the H1N1 Infectivity Gene (hemagglutinin protein area in white), the Mean Replikin Count increased from 4.3 (+/−2) in 2001 to 6.7 (+/−1.2) in 2008 ($p<0.001$). At that time, the applicants published their warning that H1N1 was the leading candidate for a pandemic. The Mean Replikin Count then continued to increase 43% to a mean count of 10 by April 2009. At that point, the clinical H1N1 outbreak in Mexico and California was reported. By June 2009, the World Health Organization stated that the outbreak had sufficiently spread globally to be declared a pandemic.

As of September 2009, the Infectivity Gene Count (hemagglutinin in white) remains elevated, decreasing only 3% in its mean since the high in April 2009, thus giving no significant sign of abatement (as yet) in the current pandemic. If the Replikin Count were to decrease significantly, an abatement such as that which occurred in SARS would be expected. In the SARS outbreak of 2003, a sharp drop in the Replikin Count of the spike protein in 2003 signaled the abrupt end of the clinical outbreak. See U.S. application Ser. No. 12/010,027, filed Jan. 18, 2008, FIG. 9.

FIG. 5 also shows that for the H1N1 Lethality Gene (pB1 gene area, in black), the Mean Replikin Count between 2001 to 2008, despite some activity, did not increase significantly (in contrast to the Infectivity Gene—hemagglutinin protein area). However, the Standard Deviation of the Mean (SD) in the pB1 gene area (represented by capped lines) increased five-fold between 2001 and December 2008 and forty-five fold between 2001 and April 2009. An increase in standard deviation of mean Replikin Count indicates that some viruses in a virus population have high Replikin Counts and are engaging in high replication rates.

As may be seen in FIG. 5, mean Replikin Count in the pB1 gene area of H1N1 isolates has gradually decreased by 38% from its high in April 2009 through to Sep. 23, 2009 ($p<0.001$). However, the mean Replikin Count is still 15% higher, and the standard deviation of the mean is still 19 times greater, than the level of Replikin Count seen in 2001, which may be considered a "resting rate" for purposes of FIG. 5. These higher Replikin Counts indicate that there are still active individual viruses within the currently circulating H1N1 virus population that contain increased Replikin Counts in their Lethality Genes. The overall trend seen in FIG. 5 since April 2009, however, is clearly towards a return to the lower "resting" Replikin Count of about two, which predominated from 1980 to 2008 (or less than two, which predominated from 1934 to 1979). These low Replikin Counts from 1934 to 2008 were accompanied by low clinical H1N1 lethality.

The recent increase in the Replikin Count of the Replikin Infectivity Gene of H1N1 (which gave warning of the H1N1 pandemic of 2009) together with the current statistically significant decline in the Replikin Count of the Lethality Gene (which was followed by a sharp drop in H1N1 pediatric mortality since June 2009) raise the possibility that, although high infectivity will persist, there is no indication at present that a high mortality rate is to be expected. Nevertheless, as the Replikin Count is further monitored, the status of the infectivity and lethality of the current H1N1 pandemic (as determined by Replikin Count) may change at any time, as the lethality gene Replikin Count did at the beginning of 2009.

Example 6

Replikin Count by Year for H1N1 from 1933 Through 2008

The applicants reviewed publicly available pB1 gene area sequences from isolates of H1N1 influenza virus isolated between 1933 and 2000 at www.pubmed.com. The data is provided in Table 8 below. After a high Replikin Count in the pB1 gene area of influenza isolates in 1933 (associated with the H1N1 outbreak of that year), the data demonstrate a remarkable consistency from 1934 through 1980 (Replikin Counts generally below two) and a remarkable consistency from 1981 through 2000 (Replikin Counts generally around two). (1933 was the last significant outbreak of H1N1 prior to the present pandemic. The small and limited outbreak of 1976, was marked by a Replikin Count of 1.9+/−0.2, and never developed further, as would be expected from the low Replikin Count, either in its Count or clinically. Had the Replikins been known at that time, the hurried vaccination of millions of people because of the fear of another H1N1 pandemic might have been avoided.) This consistency in Replikin Count in the pB1 gene area continued through 2008. See FIG. 5. It was broken, however, beginning in December of 2008 when it rose from 2 to 3.7 between December 2008 and April 2009. See Table 7 above and FIG. 5. This significant rise in the Replikin Count of the pB1 gene area (Lethality Gene) corresponds to the outbreak of the present pandemic.

TABLE 8

H1N1 Annual Mean Replikin Count in pB1 Gene Area

| Year | PubMed Accession Number-Replikin Count | No. of Isolates per year | Mean Replikin Count per year | S.D. | Significance |
|---|---|---|---|---|---|
| 1933 | ABD77804 18 ACV49542 18 ACF54606 18 ABF47963 18 | 4 | 2.4 | 0.0 | low p < 0.001 |
| 1934 | ACV49553 12 ACF41842 12 ABD77683 12 | 3 | 1.6 | 0.0 | low p < 0.001, prev p < 0.001 |
| 1935 | ABD62789 14 ABO38392 11 ABN59420 12 | 3 | 1.6 | 0.2 | low p < 0.20, prev p > 0.50 |

TABLE 8-continued

H1N1 Annual Mean Replikin Count in pB1 Gene Area

| Year | PubMed Accession Number-Replikin Count | No. of Isolates per year | Mean Replikin Count per year | S.D. | Significance |
|---|---|---|---|---|---|
| 1940 | ABI20834 11 | 1 | 1.5 | 0.0 | |
| 1940 | ABI20834 | 1 | 1.5 | 0.0 | |
| 1942 | ABD62850 9 | 1 | 1.2 | 0.0 | |
| 1943 | ABO38381 11 ABO38062 11 | 2 | 1.5 | 0.0 | prev p < 0.001 |
| 1945 | ABP49335 11 | 1 | 1.5 | 0.0 | |
| 1946 | ABD79120 11 ACV49564 14 | 2 | 1.7 | 0.3 | low p > 0.50, prev p > 0.50 |
| 1947 | ABD77815 11 ACV49575 11 | 2 | 1.5 | 0.0 | prev p < 0.40 |
| 1948 | ABN59409 12 | 1 | 1.6 | 0.0 | prev p < 0.001 |
| 1949 | ABN59442 12 | 1 | 1.6 | 0.0 | |
| 1950 | ABD61743 12 ABP49324 12 | 2 | 1.6 | 0.0 | low p < 0.001 |
| 1951 | ABR15816 12 ABQ44479 12 ABQ01319 12 ABP49489 12 | 4 | 1.6 | 0.0 | low p < 0.001 |
| 1954 | ABD60974 11 ABO52288 11 | 2 | 1.5 | 0.0 | prev p < 0.001 |
| 1957 | ABD15267 12 | 1 | 1.6 | 0.0 | prev p < 0.001 |
| 1976 | ACU80022 14 ACQ99829 14 ABV45846 16 ABQ44402 14 | 3 | 1.9 | 0.2 | low p < 0.02, prev p < 0.05 |
| 1977 | ABD95358 11 ABD60941 11 ABO44142 12 | 4 | 1.5 | 0.1 | low p < 0.30, prev p < 0.002 |
| 1978 | ABY81357 14 ABP49456 8 ABP49346 14 ABO38073 8 ABO33000 8 ABO32989 11 ABN59431 8 ABK79956 11 ABG26821 11 ABF47745 11 ABF47734 11 ABF47723 11 ABF47712 11 ABF47701 11 | 14 | 1.4 | 0.3 | low p < 0.40, prev p < 0.20 |
| 1979 | ABW36319 14 ABQ01330 14 ABN50764 14 | 3 | 1.8 | 0.0 | low p < 0.001, prev p < 0.001 |
| 1980 | ABO38370 15 ABO33017 15 ABF47756 15 | 3 | 2.0 | 0.0 | low p < 0.001, prev p < 0.001 |
| 1981 | ABO52266 15 | 1 | 2.0 | 0.0 | prev p > 0.50 |
| 1982 | ABD95347 18 ABO52805 15 | 2 | 2.2 | 0.3 | low p < 0.10, prev p < 0.50 |
| 1983 | ABW91193 15 ABO38348 15 ABO37996 15 ABO33033 15 ABN50925 15 ABN50908 18 ABM66894 15 ABM66916 15 ABM66905 15 ABM22243 15 ABM22232 15 ABM22221 15 ABM22210 15 ABM22199 15 ABM22188 15 ABM22177 15 ABM22166 15 ABL67272 15 ABL67261 15 ABK80055 15 ABK80044 15 ABK80033 15 ABK40609 15 ABK40598 15 ABK40587 15 ABK40576 15 ABK40565 15 ABK40554 15 ABK40543 15 ABK40518 15 ABI92310 18 ABI30386 15 ABI20867 15 ABG88352 18 ABG88341 18 ABF47833 15 ABF47778 15 ABG79960 15 ABF47855 15 ABF47844 15 ABF47767 15 ABF47800 15 ABG26843 15 ABG26832 15 ABF47822 15 ABF47811 15 ABF47789 15 | 47 | 2.0 | 0.1 | low p < 0.001, prev p < 0.40 |
| 1984 | ABP49357 15 ABO38414 15 | 2 | 2.0 | 0.0 | low p < 0.001, prev p < 0.04 |
| 1986 | P03430 18 P03431 12 ABP49368 15 ABO44131 15 ABO38403 15 ABM22254 15 P03427 18 | 7 | 2.0 | 0.3 | low p < 0.001, prev p > 0.50 |
| 1987 | ACV49674 15 ABQ44424 15 ABN50948 15 ABN50936 15 | 4 | 2.0 | 0.0 | low p < 0.001, prev p > 0.50 |
| 1988 | ABU80408 16 | 1 | 2.1 | 0.0 | prev p < 0.001 |
| 1989 | ACL12269 15 ACK99451 15 | 2 | 2.0 | 0.0 | low p < 0.001, prev p < 0.001 |
| 1990 | P16512 20 P16510 17 P16514 16 P18882 14 P16502 12 | 5 | 2.1 | 0.4 | low p < 0.02, prev p > 0.50 |
| 1991 | ABD60963 15 ACQ84485 15 ACF41941 15 ACF41930 12 | 4 | 1.9 | 0.2 | low p < 0.02, prev p < 0.30 |
| 1993 | AAA43643 16 AAA43641 12 AAA43640 20 AAA43639 17 AAA43582 18 AAA43581 14 | 6 | 2.1 | 0.4 | low p < 0.005, prev p < 0.20 |
| 1995 | ACK99473 15 ACF41875 15 ABG88330 15 ABG26799 15 ABF47646 15 ABJ53446 15 ABI92321 15 ABI30375 15 ABI20878 15 ABI20845 15 ABG88319 15 ABG88308 15 ABF47635 15 ABG47848 15 ABG26788 15 ABF47613 15 ABE26999 15 ABE12040 15 ABE11968 13 ABE11930 15 ABE11908 15 ABE11897 15 ABE11886 15 ABE11875 15 | 24 | 2.0 | 0.1 | low p < 0.001, prev p < 0.20 |
| 1996 | ABO52233 15 ABO38018 15 ABN51074 15 ABN50981 15 ABN50970 15 ABN50959 15 ABF47657 15 ABM22298 15 ABM22287 15 ABM22276 15 ABM22265 15 ABJ53512 15 ABJ53501 15 ABI95291 15 ABI95280 15 ABI95269 15 ABI95258 15 ABI93036 15 ABI21582 15 ABI21571 15 ABI21560 15 ABI21549 15 ABI21538 15 ABI21527 15 ABI20856 11 ABG47837 15 ABF47668 15 | 27 | 2.0 | 0.1 | low p < 0.001, prev p > 0.50 |
| 1999 | ACR15312 19 ACF41886 15 ABK40014 15 ABJ16617 15 | 4 | 2.1 | 0.3 | low p < 0.01, prev p < .20 |
| 2000 | Q82571 11 AAF99677 17 AAF99676 17 ABV45857 15 ABU80317 15 ABU80306 15 ABS49995 15 ABS49984 15 | 81 | 2.0 | 0.1 | low p < 0.001, prev p < 0.40 |

TABLE 8-continued

H1N1 Annual Mean Replikin Count in pB1 Gene Area

| Year | PubMed Accession Number-Replikin Count | No. of Isolates per year | Mean Replikin Count per year | S.D. | Significance |
|---|---|---|---|---|---|
| | ABR28809 15 ABR28787 15 ABR28776 15 ABR15926 15 ABR15915 15 ABR15904 15 ABR15893 15 ABP49390 15 ABP49313 18 ABP49225 15 ABO44054 15 ABM22034 15 ABL67217 15 ABL67195 15 ABK79978 15 ABK40058 15 ABK40047 15 ABK40036 15 ABJ53523 15 ABJ53457 15 ABJ16738 15 ABJ16727 15 ABJ16650 15 ABJ09335 17 ABI95302 15 ABI95225 15 ABG88561 15 ABG88550 15 ABG80191 15 ABG80180 15 ABG67488 15 ABG48057 15 ABG37370 19 ABF47899 15 ABF47888 15 ABF47877 15 ABG47826 15 ABG47815 15 ABE11676 17 ABE11665 15 ABD95039 15 ABD95028 15 ABD95017 15 ABD95006 15 ABD94995 15 ABD94984 17 ABD94973 15 ABD94764 15 ABD78046 12 ABD78035 15 ABD78024 15 ABD78013 15 ABD78002 15 ABD77991 15 ABD77980 15 ABD77969 15 ABD77958 15 ABD77947 15 ABD77936 15 ABD77925 15 ABD77738 15 ABD77727 15 ABD77716 18 ABD63071 15 ABD61548 15 ABD61526 15 ABD60908 15 ABD60897 15 ABD60886 15 ABD60875 15 ABD60864 15 ABA08505 15 ABA08494 15 | | | | |
| 2001 | ABR28853 15 ABR28842 15 ABO38337 15 ABO38326 15 ABO38051 15 ABO38040 17 ABO38029 15 ABO32967 15 ABO32956 15 ABN51151 15 ABN51085 15 ABM66872 15 ABJ09159 15 ABG67499 15 ABG37403 15 ABG37392 15 ABG26953 15 ABF82948 15 ABF82937 15 ABF82926 15 ABF82915 18 ABF82904 15 ABF82893 15 ABF82882 15 ABF82871 15 ABF82860 15 ABF82849 15 ABF82838 15 ABF82827 15 ABF47679 15 ABF47580 15 ABF47569 15 ABG37128 15 ABF82692 15 ABF82681 15 ABF82670 15 ABF47591 18 ABE12292 15 ABE11864 15 ABE11853 15 ABE11842 15 ABE11831 15 ABE11820 15 ABE11742 15 ABE11731 15 ABE11720 15 ABE11709 15 ABE11698 15 ABE11687 15 ABD95336 15 ABD95325 15 ABD95314 15 ABD95303 15 ABD95292 15 ABD95281 15 ABD95270 15 ABD95259 15 ABD95248 15 ABD95237 15 ABD95226 15 ABD95215 15 ABD95204 15 ABD95193 15 ABD95182 15 ABD95171 15 ABD95160 15 ABD95149 15 ABD95138 15 ABD95127 15 ABD95116 15 ABD95105 15 ABD95094 15 ABD95083 15 ABD95072 15 ABD95061 15 ABD95050 15 ABD94819 15 ABD94808 15 ABD94797 15 ABD94786 15 ABD78101 15 ABD78090 15 ABD78079 15 ABD78068 15 ABD60919 18 ABC86245 15 ABC40541 15 ABB02822 15 ABA87239 15 ABA87099 15 ABC02285 15 ABB82202 15 ABB80053 15 ABB79998 15 ABB79987 15 ABB53715 15 ABB02944 15 ABB02932 15 ABB02921 15 ABB02833 15 ABA87053 15 ABA43197 15 ABA42583 15 ABA42332 18 ABA42266 15 ABA42244 15 ABA18045 15 ABA12726 15 ABA08527 15 ABA08472 15 AAZ85134 15 AAZ83307 15 AAZ79612 15 AAZ38635 15 AAK18014 14 AAK18013 15 | 116 | 2.0 | 0.1 | low p < 0.001, prev p > 0.50 |
| 2002 | ACR15334 15 ACR15323 15 ACR15224 15 ABA87088 15 ABB82224 15 AAZ83261 15 | 6 | 2.0 | 0.0 | low p < 0.001, prev p < 0.02 |
| 2003 | AAO88267 15 ABN51096 15 ABM67059 15 ABD60787 15 ABD15523 15 ABC41722 19 ABB03131 15 ABA87065 15 AAZ83985 15 ABB82213 15 ABB80111 15 ABB53748 15 ABB03153 14 ABB02811 15 ABB02800 15 ABA42255 15 ABA18153 15 ABA12737 15 ABA12716 15 ABA12704 15 ABA08483 15 ABK40003 12 CAD58687 6 | 23 | 2.0 | 0.1 | low p < 0.001, prev p > 0.50 |
| 2004 | ABC42758 15 | 1 | 2.0 | 0.0 | prev p > 0.50 |
| 2005 | ABR28908 15 ABP49401 15 ABO32978 15 ABO32686 8 ABK40697 8 ABJ16694 15 ABJ16683 15 ABJ16672 15 ABJ16661 15 ABJ09192 15 ABI92387 15 ABI30573 15 ABI22156 15 ABI21241 15 ABI21230 8 ABI21219 15 ABI21208 15 ABI21197 15 ACG50704 15 P0C0U1 13 | 20 | 2.4 | 3.0 | low p < 0.10, prev p < 0.40 |
| 2006 | ABD59820 19 ABD59818 15 ABD59816 15 ABB86941 15 ABB86958 16 ABB86955 13 ABB86954 17 ABB86950 14 ABB86901 15 ABB86871 14 ACO94812 15 ACI26458 15 ABX58687 15 ABX58247 15 ABW71302 15 ABV29565 15 ABV29554 15 ABV29543 17 ABK79967 15 ACN72626 20 ABB86921 14 ABB86911 12 ABB86891 16 ABG88887 14 2HN8_A 2 | 25 | 2.1 | 0.7 | low p < 0.001, prev p > 0.50 |
| 2007 | Q3HM40 14 Q1WP01 11 ABS00317 15 ACU80176 15 ACU80000 15 ACR61674 15 ACR61663 15 ACR15202 15 ACN43000 17 ACN42989 17 ACN33109 15 ACN33098 15 ACN32845 15 ACN32834 15 ACN32823 15 ACN32812 15 | 318 | 2.1 | 1.1 | low p < 0.001, prev p > 0.50 |

TABLE 8-continued

H1N1 Annual Mean Replikin Count in pB1 Gene Area

| Year | PubMed Accession Number-Replikin Count | No. of Isolates per year | Mean Replikin Count per year | S.D. | Significance |
|---|---|---|---|---|---|
| | ACN32801 15 ACL12071 15 ACF41688 15 ACD56288 15 | | | | |
| | ACD56132 19 ACD56121 15 ACC61994 15 ACC61983 15 | | | | |
| | ACC61972 15 ACA96527 15 ACA24532 15 ACA24521 15 | | | | |
| | ABY81423 15 ABY81412 15 ABY81401 17 ABY81390 15 | | | | |
| | ABY81368 15 ABY51267 15 ABY51256 15 ABY51245 15 | | | | |
| | ABY51201 15 ABY51190 15 ABY51179 15 ABY51168 15 | | | | |
| | ABY51157 15 ABY51146 17 ABY51124 15 ABY51113 15 | | | | |
| | ABY51102 15 ABY51091 17 ABY51080 15 ABY51069 15 | | | | |
| | ABY51058 15 ABY51047 15 ABY51025 15 ABX58720 15 | | | | |
| | ABX58709 17 ABX58698 15 ABX58643 15 ABX58632 15 | | | | |
| | ABX58621 15 ABX58610 15 ABX58599 15 ABX58588 15 | | | | |
| | ABX58577 15 ABX58566 15 ABX58555 15 ABX58544 17 | | | | |
| | ABX58533 17 ABX58522 15 ABX58511 15 ABX58500 15 | | | | |
| | ABX58489 17 ABX58478 15 ABX58467 17 ABX58456 15 | | | | |
| | ABX58445 15 ABX58434 15 ABX58423 17 ABX58412 15 | | | | |
| | ABX58401 15 ABX58390 15 ABX58379 15 ABX58368 15 | | | | |
| | ABX58357 17 ABX58346 15 ABX58324 15 ABX58313 17 | | | | |
| | ABX58302 15 ABX58291 15 ABX58280 15 ABX58269 15 | | | | |
| | ABX58258 15 ABW91644 15 ABW91633 15 ABW91622 15 | | | | |
| | ABW91611 17 ABW91600 15 ABW91589 15 ABW91578 15 | | | | |
| | ABW91567 15 ABW91545 15 ABW91534 15 ABW91523 17 | | | | |
| | ABW91512 15 ABW91501 15 ABW91490 17 ABW91468 17 | | | | |
| | ABW91457 17 ABW91435 15 ABW91424 15 ABW91413 17 | | | | |
| | ABW91391 15 ABW91380 15 ABW91369 15 ABW91358 15 | | | | |
| | ABW91347 15 ABW91336 15 ABW91325 15 ABW91314 15 | | | | |
| | ABW91303 15 ABW91281 15 ABW91226 15 ABW86614 15 | | | | |
| | ABW86549 15 ABW86538 15 ABW86527 15 ABW86516 15 | | | | |
| | ABW86505 17 ABW86494 15 ABW86483 15 ABW86472 15 | | | | |
| | ABW86461 15 ABW86450 15 ABW86439 15 ABW86428 15 | | | | |
| | ABW86417 15 ABW86406 17 ABW86395 15 ABW86384 15 | | | | |
| | ABW86373 15 ABW86362 15 ABW86351 15 ABW86340 15 | | | | |
| | ABW86329 17 ABW71478 15 ABW71467 15 ABW71456 15 | | | | |
| | ABW71445 15 ABW71434 15 ABW71423 15 ABW71412 15 | | | | |
| | ABW71401 15 ABW71390 15 ABW71379 15 ABW71368 17 | | | | |
| | ABW71346 15 ABW71335 15 ABW71324 15 ABW71313 17 | | | | |
| | ABW40683 15 ABW40672 17 ABW40650 15 ABW40628 15 | | | | |
| | ABW40617 15 ABW40606 17 ABW40584 15 ABW40573 15 | | | | |
| | ABW40562 15 ABW40551 15 ABW40540 15 ABW40529 15 | | | | |
| | ABW40518 17 ABW40507 15 ABW40496 15 ABW40485 15 | | | | |
| | ABW40474 15 ABW40463 15 ABW40452 15 ABW40441 17 | | | | |
| | ABW40430 15 ABW40419 15 ABW40408 15 ABW40397 15 | | | | |
| | ABW40375 15 ABW40364 15 ABW40353 17 ABW40342 17 | | | | |
| | ABW40320 15 ABW40309 15 ABW40298 15 ABW40287 15 | | | | |
| | ABW40265 15 ABW40243 15 ABW40232 15 ABW40221 15 | | | | |
| | ABW40210 15 ABW40188 15 ABW40166 12 ABW40155 15 | | | | |
| | ABW40133 15 ABW40122 15 ABW40111 15 ABW40100 15 | | | | |
| | ABW40078 15 ABW40067 15 ABW40056 15 ABW40045 15 | | | | |
| | ABW40023 17 ABW40012 15 ABW40001 15 ABW39990 15 | | | | |
| | ABW39979 15 ABW39968 15 ABW39957 15 ABW39935 15 | | | | |
| | ABW39924 15 ABW39913 15 ABW39902 15 ABW39891 19 | | | | |
| | ABW39869 15 ABW39858 15 ABW39847 15 ABW39836 15 | | | | |
| | ABW39825 15 ABW39814 15 ABW39785 15 ABW36308 15 | | | | |
| | ABW36297 15 ABW36286 15 ABW36275 15 ABW36264 15 | | | | |
| | ABW36253 15 ABW36242 15 ABW36231 15 ABW36220 15 | | | | |
| | ABW36209 15 ABW36198 15 ABW36187 15 ABV82559 15 | | | | |
| | ABV45967 15 ABV45956 15 ABV45945 15 ABV45934 15 | | | | |
| | ABV45923 15 ABV45901 15 ABV45890 15 ABV45879 15 | | | | |
| | ABV30632 15 ABV30621 15 ABV30610 15 ABV30599 15 | | | | |
| | ABV30588 15 ABV30577 15 ABV30566 15 ABV30555 15 | | | | |
| | ABV30544 15 ABV30533 15 ABV30511 15 ABV30500 15 | | | | |
| | ABV30467 15 ABV30379 15 ABV30368 15 ABV30357 15 | | | | |
| | ABV30346 15 ABV30335 17 ABV30324 15 ABV30313 15 | | | | |
| | ABV30302 17 ABV30291 15 ABV30203 15 ABV30192 15 | | | | |
| | ABV30181 15 ABV30170 15 ABV30159 15 ABV30148 17 | | | | |
| | ABV30137 15 ABV30115 12 ABV30104 15 ABV30093 15 | | | | |
| | ABV30060 15 ABV30049 15 ABV30038 15 ABV30027 15 | | | | |
| | ABV30016 15 ABV30005 15 ABV29994 15 ABV29983 15 | | | | |
| | ABV29972 15 ABV29961 15 ABV29950 15 ABV29928 15 | | | | |
| | ABV29895 15 ABV29884 15 ABV29873 15 ABV29862 15 | | | | |
| | ABV29851 15 ABV29840 15 ABV29807 15 ABV29796 15 | | | | |
| | ABV29785 15 ABV29774 15 ABV29763 15 ABV29752 15 | | | | |
| | ABV29741 15 ABV29708 15 ABV29697 15 ABV29686 15 | | | | |
| | ABV29675 15 ABV29664 15 ABV29653 15 ABV29642 15 | | | | |

TABLE 8-continued

H1N1 Annual Mean Replikin Count in pB1 Gene Area

| Year | PubMed Accession Number-Replikin Count | No. of Isolates per year | Mean Replikin Count per year | S.D. | Significance |
|---|---|---|---|---|---|
| | ABV29620 15 ABV29609 15 ABV29587 15 ABV29576 15 ACN72614 15 P0C574 12 Q20MH0 13 Q1WP00 7 ABS00328 15 Q8JSD9 10 | | | | |
| 2008 | ACP20229 15 ACP20218 15 ABV01075 15 ACV49684 15 ACU80454 15 ACU80418 15 ACU80286 19 ACU80275 15 ACU80242 18 ACU80099 15 ACU80088 15 ACU80077 15 ACU80055 15 ACU80033 15 ACU79989 15 ACU12601 15 ACU12590 15 ACU12579 15 ACU12568 15 ACU12513 15 ACR15466 15 ACR58560 15 ACR58549 15 ACR15521 15 ACR15510 15 ACR15499 15 ACR15488 15 ACR15477 15 ACR15455 15 ACR15444 15 ACR15433 15 ACR15378 15 ACR15367 15 ACR15345 15 ACR15279 15 ACR15268 15 ACR15246 15 ACQ65766 15 ACP44233 15 ACP44222 15 ACP44211 15 ACP44200 15 ACO95423 15 ACO95412 15 ACO95401 15 ACO95390 15 ACO95379 15 ACO94878 15 ACO94867 15 ACO94713 15 ACO36405 15 ACN33153 15 ACN33131 15 ACN32520 15 ACN32509 15 ACL12159 12 ACI26447 12 ACF54595 12 ABV01079 15 ABV01076 15 ABV01074 15 ABV01073 15 ABV01070 15 ABV01069 15 ABV01068 15 2ZNL_A 15 | 66 | 2.0 | 0.2 | low p < 0.001, prev p < 0.05 |
| 2009 | A3DRP8 15 A4GCI3 15 A4GCK5 15 A4GBY5 8 A8C8X1 22 B3EUR4 14 A4K151 11 A4U7B4 12 A4U6W0 11 A4GCL6 11 A4GCJ4 11 A4GCM7 11 A8C8K2 15 B4URE4 12 Q0HD52 11 Q289L9 15 Q07FH7 15 ACV42016 15 ACV41999 15 ACV41989 15 ACP41103 15 ACV53907 15 ACV53897 15 ACV53887 15 ACV53498 15 ACV53488 15 ACV53478 15 ACV53468 15 ACV53458 15 ACV53448 14 ACV53439 15 ACV41979 15 ACU30101 15 ACU30091 15 ACU30081 15 ACU30071 11 ACU30017 15 ACU30007 15 ACU29997 15 ACU29987 15 ACU29977 15 ACU29967 15 ACU29957 15 ACU29947 15 ACU00950 15 ACU00940 15 ACU00930 15 ACT79181 15 ACT79171 15 ACT79161 15 ACT79151 15 ACT79141 15 ACT22502 15 ACT21570 15 ACT11055 15 ACR54049 15 ACR47013 15 ACR46669 15 ACR46660 15 ACR08608 15 ACV82595 15 ACU27039 15 ACS54299 15 ACR78576 15 ACR67252 15 ACR67242 15 ACR55002 15 ACR54992 15 ACR54982 15 ACR54972 15 ACR54962 15 ACR38881 15 ACR08503 15 ACS92610 15 ACU31122 15 ACT36526 15 ACS73568 15 ACS73560 15 ACS73552 15 ACS69027 15 ACS36640 15 ACS36639 15 ACS36637 15 ACT36534 15 ACT36503 15 ACS50086 15 ACR09394 15 ACR09392 15 ACR08588 15 ACR08585 15 ACQ99679 15 ACQ99678 15 ACQ99676 15 ACQ76409 15 ACQ76378 15 ACQ76357 15 ACQ76349 15 ACQ76320 15 ACQ76306 15 ACQ76289 15 ACQ63280 15 ACQ63255 15 ACQ63247 15 ACQ55362 15 ACP44176 15 ACP44169 15 ACP44165 15 ACP41941 15 ACR49313 15 ACR49312 15 ACR49311 15 ACR49307 15 ACR49306 15 ACR20067 15 ACV71012 15 ACV71002 15 ACV70982 15 ACV70972 15 ACV70962 15 ACV70952 15 ACV70942 14 ACV70932 15 ACV70922 15 ACV70912 15 ACV70902 15 ACV70892 15 ACV70882 15 ACV70872 15 ACV70862 15 ACV70852 15 ACV70842 15 ACV70832 15 ACV70822 15 ACV70812 15 ACV70802 15 ACV70792 15 ACV70782 15 ACV70772 15 ACV70762 15 ACV70752 15 ACV70742 15 ACV70732 15 ACV70722 15 ACV70712 15 ACV70702 15 ACV70692 15 ACV70682 15 ACV70672 15 ACV70662 15 ACV70652 15 ACV70642 15 ACV70632 15 ACV70622 15 ACV70612 15 ACV70602 15 ACV70592 15 ACV70582 15 ACV70572 15 ACV70562 15 ACV70552 15 ACV70542 15 ACV70532 15 ACV70522 14 ACV70512 15 ACV70502 15 ACV70492 15 ACV70482 15 ACV70472 15 ACV70462 15 ACV70452 15 ACV70442 15 ACV70432 15 ACV70422 15 ACV70412 15 ACV70402 15 ACV70392 15 ACV70382 15 ACV70372 15 ACV70362 15 ACV70352 15 ACV70342 15 ACV70332 15 ACV70322 15 ACV70312 15 ACV70302 15 ACV70292 15 ACV70282 15 ACV70272 15 ACV70262 15 ACV70252 15 ACV70242 15 ACV70232 15 ACV70222 15 ACV70212 15 ACV70202 15 ACV70192 15 ACV70182 15 ACV70172 15 ACV70162 15 ACV70131 15 ACV70121 14 ACV70111 15 ACV70101 15 ACV70091 15 ACV70081 15 ACV33182 15 ACV33172 15 ACV33162 15 ACV33152 15 ACV33142 15 ACV33132 15 ACV33122 15 ACV33112 15 ACV33102 15 ACV33092 15 | 506 | 2.3 | 1.9 | low p < 0.001, prev p < 0.002 |

TABLE 8-continued

H1N1 Annual Mean Replikin Count in pB1 Gene Area

| Year | PubMed Accession Number-Replikin Count | No. of Isolates per year | Mean Replikin Count per year | S.D. | Significance |
|---|---|---|---|---|---|
| | ACV04587 15 ACV04577 15 ACV04567 15 ACV04557 15 | | | | |
| | ACV04547 15 ACV04537 15 ACV04527 15 ACV04517 15 | | | | |
| | ACV04507 15 ACV04497 15 ACV04471 15 ACV04416 15 | | | | |
| | ACV04406 15 ACV04396 15 ACV04386 15 ACV04376 15 | | | | |
| | ACV04366 15 ACV04356 15 ACV04346 15 ACV04336 15 | | | | |
| | ACV04326 15 ACV04316 15 ACV04306 15 ACV04296 15 | | | | |
| | ACV04286 15 ACV04276 15 ACV04266 18 ACV04256 15 | | | | |
| | ACV04246 15 ACV04236 15 ACU79945 15 ACU31248 15 | | | | |
| | ACU31247 15 ACU31246 15 ACU31245 15 ACU31244 15 | | | | |
| | ACU31243 15 ACU31242 15 ACU31241 15 ACU31240 15 | | | | |
| | ACU31239 15 ACU31238 15 ACU31237 15 ACU27055 15 | | | | |
| | ACU27054 15 ACU17531 15 ACU17461 15 ACU17399 15 | | | | |
| | ACU17332 15 ACU17269 15 ACU17198 15 ACU17136 15 | | | | |
| | ACU17069 15 ACU17004 15 ACU16941 15 ACU16868 15 | | | | |
| | ACU16806 15 ACU13113 15 ACU13112 15 ACU13111 15 | | | | |
| | ACU00159 15 ACT86147 15 ACT86137 15 ACT86127 15 | | | | |
| | ACT86117 15 ACT86107 15 ACT86097 15 ACT86087 15 | | | | |
| | ACT86077 15 ACT86067 15 ACT86057 15 ACT86047 15 | | | | |
| | ACT86037 15 ACT86027 15 ACT86017 15 ACT86007 15 | | | | |
| | ACT83883 15 ACT83873 15 ACT83863 15 ACT83853 15 | | | | |
| | ACT83843 15 ACT83833 15 ACT83823 15 ACT83813 15 | | | | |
| | ACT83803 15 ACR52406 15 ACT79635 14 ACT68280 15 | | | | |
| | ACT68279 14 ACT68278 15 ACT68277 15 ACT68276 15 | | | | |
| | ACT68275 14 ACT68274 15 ACT68273 15 ACT68272 15 | | | | |
| | ACT68271 15 ACT68270 14 ACT68269 15 ACT68268 15 | | | | |
| | ACT68267 15 ACT68266 15 ACT68265 15 ACT68264 15 | | | | |
| | ACT68263 15 ACT68262 15 ACT68261 15 ACR40396 15 | | | | |
| | ACT67249 15 ACT67248 15 ACT67247 15 ACT67246 15 | | | | |
| | ACT67245 15 ACT67244 15 ACT67125 15 ACT67120 15 | | | | |
| | ACT21986 15 ACT21985 15 ACT21984 15 ACT21983 15 | | | | |
| | ACT21982 15 ACS92608 15 ACS92587 15 ACS92577 15 | | | | |
| | ACT66153 15 ACT54604 15 ACT52683 15 ACT36636 15 | | | | |
| | ACT36635 15 ACT36634 14 ACT36633 15 ACT36632 15 | | | | |
| | ACS92598 15 ACT21981 15 ACT22056 15 ACT10305 15 | | | | |
| | ACT09117 15 ACR67121 15 ACS78054 15 ACS78044 15 | | | | |
| | ACS78034 15 ACS78024 15 ACS78014 15 ACS78004 15 | | | | |
| | ACS77994 15 ACS77984 15 ACS77974 15 ACS77964 15 | | | | |
| | ACS77954 15 ACS77944 15 ACS77934 15 ACS75829 15 | | | | |
| | ACR40366 15 ACS68821 15 ACS66828 15 ACS27257 15 | | | | |
| | ACS27247 15 ACS27237 15 ACS27227 15 ACS27217 15 | | | | |
| | ACS27207 15 ACS27197 15 ACS14744 15 ACS14734 15 | | | | |
| | ACS14724 15 ACS14714 15 ACS14704 15 ACS14694 15 | | | | |
| | ACS14684 15 ACS14674 15 ACR40386 15 ACR83536 15 | | | | |
| | ACR77506 15 ACR77496 15 ACR77486 15 ACR77476 15 | | | | |
| | ACR77466 15 ACR77456 15 ACR77446 15 ACR67120 15 | | | | |
| | ACR67119 15 ACR67118 15 ACR56458 15 ACR56448 15 | | | | |
| | ACR56438 15 ACR56428 15 ACR56418 15 ACR56408 15 | | | | |
| | ACR56398 15 ACR56388 15 ACR52496 15 ACR52486 15 | | | | |
| | ACR52476 15 ACR52466 15 ACR52456 15 ACR52446 15 | | | | |
| | ACR52436 15 ACR52426 15 ACR52416 15 ACR39501 15 | | | | |
| | ACR39461 15 ACR52396 15 ACR52386 15 ACR52376 15 | | | | |
| | ACR51073 15 ACR51063 15 ACR51053 15 ACR51043 15 | | | | |
| | ACR51033 15 ACR51023 15 ACR51013 15 ACR51003 15 | | | | |
| | ACR40306 15 ACR40376 15 ACR40356 15 ACR40346 15 | | | | |
| | ACR40336 15 ACR40326 15 ACR40316 15 ACR40296 15 | | | | |
| | ACR39491 15 ACR39481 15 ACR39471 15 ACR39451 15 | | | | |
| | ACR39441 15 ACR39431 15 ACR39421 15 ACR39411 15 | | | | |
| | ACR39401 15 ACR39362 15 ACR38797 15 ACR38796 15 | | | | |
| | ACR38795 15 ACR18922 15 ACR15356 12 ACR10219 15 | | | | |
| | ACR10218 15 ACR10194 15 ACR08589 15 ACR08587 15 | | | | |
| | ACR08584 15 ACQ84475 15 ACQ84465 15 ACR08467 15 | | | | |
| | ACR08457 15 ACR08447 15 ACR08437 15 ACR08427 15 | | | | |
| | ACQ73409 15 ACQ73411 15 ACQ73410 15 ACQ89953 15 | | | | |
| | ACQ89952 15 ACQ89951 15 ACQ89950 15 ACQ89949 15 | | | | |
| | ACQ89948 15 ACO94845 12 ACO94834 12 ACU87262 15 | | | | |
| | ACU64816 15 ACU64797 15 ACU64796 15 ACT66142 15 | | | | |
| | ACS34704 15 ACR78469 15 ACR54044 15 ACR15750 15 | | | | |
| | ACR15613 15 ACR67254 15 ACV67253 15 ACV67252 15 | | | | |
| | ACV67251 15 ACV67250 15 ACV67249 15 ACV67248 15 | | | | |
| | ACT35523 15 3A1G_B 1 2ZTT_B 1 A3DRP9 7 A4K152 9 | | | | |
| | A4U7B5 9 A4U6W1 19 A4GCJ5 13 A4GCM8 13 A8C8K3 7 | | | | |
| | B4URE5 9 Q07FH6 7 A4GCI4 7 A4GBY6 7 B3EUR5 9 | | | | |

Example 7

Synthetic Vaccine Against H1N1

A synthetic Replikin vaccine containing an approximately equal-parts-by-weight mixture of eight H1N1 Replikin peptides is tested in pigs. The tested vaccine is engineered from sequences identified in H1N1 in humans from 1918 to the present and confirmed to be conserved in H1N1 over decades as well as across influenza strains with conservation particularly noted in the key amino acid residues of the Replikin sequence, namely, lysine and histidine amino acid residues. The tested vaccine is engineered to block both the entry site of H1N1 virus and the replication site of those H1N1 viruses that manage to enter into host cells. As such, the vaccine is called the TWO-PUNCH vaccine. The vaccine comprises a mixture of the following twenty Replikin peptides in sterile water:

(1)     HAQDILEKEHNGKLCSLKGVRPLILK;               (SEQ ID NO: 1)

(2)  (2) KEHNGKLCSLKGVRPLILK;                     (SEQ ID NO: 2)

(3)  (3) KKNNAYPTIKRTYNNTNVEDLLIIWGIHH;           (SEQ ID NO: 3)

(4)  (4) HHSNEQGSGYAADKESTQKAIDGITNK;             (SEQ ID NO: 4)

(5)  (5) HDSNVKNLYDKVRLQLRDNAK;                   (SEQ ID NO: 5)
and (6)  (6) KVRLQLRDNAKELGNGCFEFYH.                  (SEQ ID NO: 6)

(7)  (1) KDVMESMDKEEMEITTH;                       (SEQ ID NO: 7)

(8)  (2) HFQRKRRVRDNMTKK;                         (SEQ ID NO: 8)

(9)  (3) KKWSHKRTIGKKKQRLNK;                      (SEQ ID NO: 9)

(10) (4) HKRTIGKKKQRLNK;                          (SEQ ID NO: 10)

(11) (5) HEGIQAGVDRFYRTCKLVGINMSKKK;              (SEQ ID NO: 11)

(12)     HSWIPKRNRSILNTSQRGILEDEQMYQKCCNLFEK.     (SEQ ID NO: 12)

(13)     KKGSSYPKLSKSYVNNKGKEVLVLWGVHH,           (SEQ ID NO: 21)

(14)     HPVTIGECPKYVRSTK,                        (SEQ ID NO: 22)

(15)     KFEIFPKTSSWPNH,                          (SEQ ID NO: 23)

(16)     HNGKLCKLKGIAPLQLGK,                      (SEQ ID NO: 24)

(17)     KSYVNNKGKEVLVLWGVHH,                     (SEQ ID NO: 25)

(18)     KMNTQFTAVGKEFNH,                         (SEQ ID NO: 26)

(19)     KSQLKNNAKEIGNGCFEFYH,                    (SEQ ID NO: 27)

(20)     KHSNGTVK.                                (SEQ ID NO: 28)

Four groups of pigs are created. The first group is a control group which is neither vaccinated nor inoculated with H1N1 influenza virus. The second group is vaccinated. The third group is vaccinated and inoculated with influenza virus. The fourth group is not vaccinated but is nevertheless inoculated with H1N1 influenza virus.

The vaccine is administered to all pigs in groups 2 and 3 on days 7, 14, and 21. All pigs in groups 3 and 4 are inoculated with H1N1 on day 28. Thereafter, antibody production is monitored in the serum of selected pigs in each group. Additionally, the pigs are monitored for symptoms of influenza infections. External body fluids are also tested via PCR for shedding of H1N1 influenza. The pigs in group 2, 3, and 4 produce antibodies to H1N1. The pigs in group 2 demonstrate no symptoms of influenza and shed no influenza virus detected by PCR. The pigs in group 4 demonstrate significant symptoms of influenza and shed influenza virus detected by PCR. The pigs in group 3 demonstrate reduced symptoms of influenza and shed considerably less influenza virus detected by PCR than do the pigs in group 4.

Example 8

Peptide Sequences Conserved Across Strains

Table 9 provides examples of Replikin peptides that have been identified as conserved in various strains of influenza.

TABLE 9

| Sequences Identified as Conserved across Strains | | | | |
|---|---|---|---|---|
| Conserved Replikin Sequences | Position of first amino acid of Replikin sequence in H1N1 | Shared in H5N1 pB1 Gene Area | Shared in H9N1 pB1 Gene Area | Shared in H3N2 pB1-F2 Gene Area |
| HYQKTMNQVVMPK (SEQ ID NO: 15) | 41 | Yes | | |
| HCQKTMNQVVMPK (SEQ ID NO: 14) | 41 | Yes | | Yes |
| KRWRLFSKH (SEQ ID NO: 16) | 78 | | | Yes |

TABLE 9-continued

Sequences Identified as Conserved across Strains

| Conserved Replikin Sequences | Position of first amino acid of Replikin sequence in H1N1 | Shared in H5N1 pB1 Gene Area | Shared in H9N1 pB1 Gene Area | Shared in H3N2 pB1-F2 Gene Area |
|---|---|---|---|---|
| HFQRKRRVRDNVTK (SEQ ID NO: 13) | 184 | Yes | | |
| HFQRKRRVRDNMTK (SEQ ID NO: 19) | 184 | Yes | Yes | |
| HFQRKRRVRDNMTKKMVTQRTIGK KKQRLNK (SEQ ID NO: 20) | 184 | Yes | | |
| KKKHKLDK (SEQ ID NO: 17) | 207 | Yes | | |
| KKKQRLTKX$_{n=49}$H$^{253}$ (SEQ ID NO: 18) | 207 | Yes | | |

Example 9

Replikin Peptide Sequences Conserved in H1N1 Isolates

The applicants surveyed hemagglutinin protein areas from H1N1 isolates available at www.pubmed.com for Replikin peptides conserved between 1918 and October of 2009. Applicants searched only for Replikin peptides where the hemagglutinin protein area of more than one isolate contained the exact peptide (that is, a peptide that is 100% homologous with another peptide from a different isolate). An exemplary list of conserved Replikin peptides and the years in which isolates having the conserved Replikin peptides were identified is provided below:

1) $^{170}$KKGNSYPKLSKSYINDKGKEVLVLWGIHH$^{179}$ (SEQ ID NO: 32) conserved in isolates from 2009
2) $^{170}$KNGLYPNLSKSYANNKEKEVLVLWGVHH$^{197}$ (SEQ ID NO: 33) observed as conserved in isolates from 2009
3) KLSKSYVNNKGKEVLVLWGVHH (SEQ ID NO: 34) observed as conserved in isolates from 1918, 1930, 1991, and 2009
4) KFEIFPKTSSWPNH (SEQ ID NO: 35) observed as conserved in isolates from 1918, 1930, 1991, and 2009
5) KSYVNNKGKEVLVLWGVHH (SEQ ID NO: 36) observed as conserved in isolates from 1918, 1930, 1991, 1997, 1999, 2009
6) HPVTIGECPKYVRSTK (SEQ ID NO: 37) observed as conserved in isolates from 1918, 1933, 1942, 1943, 1945, 1948, 1949, 1950, 1951, 1954, 1957, 1977-1984, 1986-1989, 1991, 1994-1997, 1999-2001, 2003, 2004, 2006-2009 on the C-terminal portion of the protein
7) KEFNHLEK (SEQ ID NO: 38) observed as conserved in isolates from 1976, 1988, 1991, 1997, 1998, 2003, 2004, 2009
8) HLEKRIENLNKK (SEQ ID NO: 39) observed as conserved in isolates from 1976, 1988, 1991, 1997, 1998, 2003, 2004, 2009
9) KMNTQFTAVGKEFNH (SEQ ID NO: 40) observed as conserved in isolates from 1976, 1988, 1991, 1997, 1998, 2003, 2004, 2009
10) KHSNGTVK (SEQ ID NO: 41) observed as conserved in isolates from 2009
11) KSYINDKGKEVLVLWGIHH (SEQ ID NO: 42) observed as conserved in isolates from 2009
12) HPITIGKCPKYVK (SEQ ID NO: 43) observed as conserved in isolates from 2009
13) KHNGKLCK (SEQ ID NO: 44) observed as conserved in isolates from 2009
14) HAGAKSFYKNLIWLVKK (SEQ ID NO: 45) observed as conserved in isolates from 2009
15) HKCDNTCMESVK (SEQ ID NO: 46) observed as conserved in isolates from 2009
16) HSVNLLEDKHNGKLCK (SEQ ID NO: 47) observed as conserved in isolates from 2009
17) HSVNILEDKHNGKLCK (SEQ ID NO: 48) observed as conserved in isolates from 2009
18) KHSNGTVK (SEQ ID NO: 49) observed as conserved in isolates from 1918, 1933, 1934, 1940, 1947, 1977, 1978, 1979, 1980, 1983, 1985
19) HNGKLCKLKGIAPLQLGK (SEQ ID NO: 50) observed as conserved in isolates from 1918, 1933, 1934, 1982-1984, 2009
20) HNGKLCKLKGIAPLQLGK (SEQ ID NO: 51) observed as conserved in isolates from 1918, 1933, 1934, 1982, 1983, 1984, 2009
21) KSQLKNNAKEIGNGCFEFYH (SEQ ID NO: 52) observed as conserved in isolates from 2009
22) HPVTIGECPKYVKSTK (SEQ ID NO: 53) observed as conserved in isolates from 1930-2008
23) HDSNVKNLYEKVK (SEQ ID NO: 54) observed as conserved in isolates from 1934-2008
24) HDSNVKNLYEKVKSQLK (SEQ ID NO: 55) observed as conserved in isolates from 1934-2008
25) HPVTIGECPKYVRSAK (SEQ ID NO: 56) observed as conserved in isolates from 1934-2008
26) HKCNNECMESVK (SEQ ID NO: 57) observed as conserved in isolates from 1940-2008
27) KSYVNNKEKEVLVLWGVH (SEQ ID NO: 58) observed as conserved in isolates from 1947-2008
28) HPITIGECPKYVKSTK (SEQ ID NO: 59) observed as conserved in isolates from 1976-2008

29) HKCDDECMESVK (SEQ ID NO: 60) observed as conserved in isolates from 1976-2008
30) HNGKSSFYKNLLWLTGK (SEQ ID NO: 61) observed as conserved in isolates from 1996-2008
31) HKCNDECMESVK (SEQ ID NO: 62) observed as conserved in isolates from 1996, 2001, 2002, 2003, 2004, 2005, 2006, 2007, 2008
32) KSYANNKEKEVLVLWGVHH (SEQ ID NO: 63) observed as conserved in isolates from 1999-2008
33) HYSRKFTPEIAK (SEQ ID NO: 64) observed as conserved in isolates from 2000-2008
34) HNGESSFYRNLLWLTGKNGLYPNLSK (SEQ ID NO: 65) observed as conserved in isolates from 2003-2008
35) KESWSYIVEKPNPENGTCYPGH (SEQ ID NO: 66) observed as conserved in isolates from 2004-2008

Example 10

Conservation of SEQ ID NO: 8 in H9N2 Isolates

The applicants surveyed SEQ ID NO: 8 (HFQRKRRVRD-NMTKK, originally identified in H5N1) in isolates of H9N2 influenza virus available at www.pubmed.com and found the sequence in the following accession numbers at the listed positions in the following years:

| Year | PubMed Accession Number |
|---|---|
| 1966 | Q0A451 position 184, AAD49039 position 184. |
| 1976 | ABB88306 position 184. |
| 1978 | AAP49097 position 184. |
| 1979 | ABB20321 position 184. |
| 1992 | AAD49034 position 184. |
| 1993 | AAD49038 position 184. |
| 1994 | AAD49033 position 184, AAD49032 position 184. |
| 1995 | AAQ04911 position 124, AAQ04907 position 171. |
| 1996 | AAD49037 position 184, AAD49036 position 184, AAQ04928 position 184, AAQ04924 position 183, AAD49035 position 184. |
| 1997 | Q9WLS3 position 184, AAD49031 position 184, BAB39507 position 184, BAF46425 position 184, AAD49027 position 184, AAQ04927 position 184, AAQ04926 position 184, AAQ04923 position 177, AAQ04920 position 180, AAQ04918 position 184, AAQ04914 position 116, AAD49030 position 184, AAD49029 position 184, AAD49026 position 184, CAB95863 position 184, AAD49028 position 184, AAK49362 position 184, AAK49356 position 184, AAK49358 position 184, AAK49357 position 184. |
| 1998 | BAB39508 position 184, AAP04506 position 184, AAQ04919 position 184, AAQ04916 position 184, AAQ04910 position 171, AAL14089 position 184, AAL14088 position 184, ACG59798 position 152, AAT65269 position 184, AAT65267 position 184, AAT65253 position 184. |
| 1999 | CAB95865 position 184, CAB95864 position 184, ABU63965 position 184, ABK59029 position 184, BAE96031 position 184, AAK49355 position 184, AAK49354 position 184, AAQ04925 position 184, AAQ04922 position 184, AAQ04915 position 179, AAQ04913 position 138, AAQ04912 position 156, AAQ04909 position 86, AAQ04908 position 124, AAL32491 position 178, ABI94772 position 184, CAC19698 position 184, AAG48199 position 170, AAG48198 position 170, AAG48196 position 170, AAG48195 position 170, AAG48194 position 170, AAG48193 position 170, AAG48192 position 170, AAG48191 position 170, AAG48190 position 170. |
| 2000 | AAP49085 position 184, AAP49084 position 184, AAP49100 position 76, AAP49093 position 184, AAP49091 position 184, AAP49090 position 184, AAP49089 position 184, AAP49087 position 184, AAP49086 position 184, ABQ57376 position 184, ABF56630 position 184, ABF56639 position 184, ABF56621 position 184, ABV31865 position 184, ABV48111 position 184, ABV47990 position 184, ABV47869 position 184, ABV46313 position 184, AAQ04921 position 184, AAQ04917 position 179, AAG48197 position 170, ABB90211 position 184, ABB90200 position 184, AAN84435 position 177, AAN84404 position 177, AAN84382 position 177. |
| 2001 | AAP49099 position 179, AAP49092 position 184, AAP49088 position 184, ABM46527 position 184, ABV48571 position 184, ABV47605 position 173, ABV46829 position 184, ABV46626 position 184, BAF46525 position 184, BAF46515 position 184, BAF46505 position 184, BAF46495 position 184, BAF46465 position 184, BAF46455 position 184, BAF46445 position 184, BAF46435 position 184, ABJ15707 position 87, ABI96775 position 93, ABG27054 position 184, ABG27037 position 184, ACG59796 position 152, ABM46591 position 184, ABM46590 position 184, ABM46589 position 184, ABM46588 position 184, ABM46587 position 184, ABM46586 position 184, ABM46585 position 184, ABM46584 position 184, ABM46583 position 184, ABM46582 position 184, ABM46581 position 184, ABM46580 position 184, ABM46579 position 184, ABM46578 position 184, ABM46577 position 184, ABM46576 position 184, ABM46575 position 184, ABM46574 position 184, ABM46573 position 184, ABM46572 position 184, ABM46571 position 184, ABM46570 position 184, ABM46569 position 184, ABM46568 position 184, ABM46567 position 184, ABM46566 position 184, ABM46565 position 184, ABM46564 position 184, ABM46563 position 184, ABM46562 position 184, ABM46561 position 184, ABM46560 position 184, ABM46559 position 184, ABM46558 position 184, ABM46557 position 184, ABM46556 position 184, ABM46555 position 184, ABM46554 position 184, ABM46553 position 184, ABM46552 position 184, ABM46551 position 184, ABM46550 position 184, ABM46549 position 184, ABM46548 position 184, ABM46547 position 184, ABM46546 position 184, ABM46545 position 184, ABM46544 position 184, ABM46543 position 184, ABM46542 position 184, ABM46541 position 184, ABM46540 position 184, ABM46539 position 184, ABM46538 position 184, ABM46537 position 184, ABM46536 position 184, ABM46535 position 184, ABM46534 position 184, ABM46533 position 184, ABM46532 position 184, ABM46531 position 184, ABM46530 position 184, ABM46529 position 184, ABM46528 position 184, ABM46526 position 184, ABM46525 position 184, ABM46524 position 184, ABM46523 position 184, ABM46522 position 184, ABM46521 position 184, ABM46520 position 184, ABM46519 position 184, AAN84413 position 177, AAN84412 position 177. |

| Year | PubMed Accession Number |
|---|---|
| 2002 | ABV47385 position 184, ABV47770 position 184, ABV47682 position 184, ABV47649 position 184, ABV47550 position 184, ABV47429 position 184, ABV47308 position 184, ABV47187 position 184, ABV47066 position 184, BAF46485 position 184, BAF46475 position 184, ABI97312 position 184, ABI94786 position 103. |
| 2003 | ABV48012 position 177, ABV48001 position 184, ABV47968 position 184, ABV47957 position 184, ABV47924 position 184, ABV47913 position 184, ABV47891 position 184, ABV47880 position 184, ABV47858 position 184, ABV47825 position 184, ABV47814 position 184, ABV47792 position 184, ABV47704 position 184, ABB58993 position 184, ABB58989 position 184, ABK00142 position 184, ACA42426 position 184, ABB19963 position 184, ABB58999 position 184, ABB58998 position 184, ABB58997 position 184, ABB58996 position 184, ABB58995 position 184, ABB58994 position 184, ABB58992 position 184, ABB58991 position 184, ABB58990 position 184, AAV65823 position 184, AAU11278 position 184, AAU11277 position 184, AAU11276 position 184, AAU11275 position 184, AAU11274 position 184, AAU11273 position 184, AAU11272 position 184, AAU11271 position 184, AAU11270 position 184, AAU11269 position 184, AAU11268 position 184, AAU11267 position 184, AAU11266 position 184, AAU11265 position 184, AAU11264 position 184, AAU11263 position 184, AAU11262 position 184, AAU11261 position 184, AAV30834 position 184, AAW78094 position 184, AAW78093 position 184, AAW78092 position 184, AAW78091 position 184, AAW78090 position 184, AAW78089 position 184, AAW78088 position 184, AAW78087 position 184, AAW78086 position 184. |
| 2004 | ACF37318 position 184, ABL61403 position 175, ABE28411 position 184, ABV48364 position 184, ABV46895 position 184, ABV46797 position 184, ABV46787 position 184, ABV46766 position 184, ABV46670 position 184, ABV48342 position 184, ABV48331 position 172, ABV48320 position 172, ABV48287 position 171, ABV48254 position 171, ABV48221 position 184, ABV48210 position 184, ABV48144 position 177, ABV48133 position 184, ABV48122 position 184, ABV48100 position 184, ABV48089 position 184, ABV48078 position 184, ABV48067 position 184, ABV48056 position 184, ABV48045 position 184, ABV48034 position 184, ABV48023 position 172, ABV46862 position 184, ABV46776 position 184, ABV46659 position 184, ABV46648 position 184, ABV46637 position 184, ACA25366 position 184, ACA25356 position 184, ABC48846 position 184, ABC48836 position 184, ABC48826 position 184, ABC48816 position 184, ABC48806 position 148, ACA42436 position 184, AAV68029 position 184, AAV68004 position 184, AAV67998 position 184, AAV68012 position 184, AAV67990 position 184. |
| 2005 | ABS57525 position 184, ABS57521 position 184, ABS57517 position 184, ACG59800 position 152, ABV48374 position 184, ABV47023 position 184, ABV46958 position 184, ABV46937 position 184, ABV46905 position 184, ABV31976 position 184, ABV31975 position 184, ABV31955 position 184, ABV31933 position 184, ABV31913 position 184, ABV31912 position 184, ABV31887 position 184, ABV48395 position 184, ABV48384 position 184, ABV46915 position 184, ABQ51943 position 184, ABI96712 position 184, ABV31888 position 184, ABV31851 position 184 |
| 2006 | ACF37316 position 184, ABV31956 position 184, ABV31935 position 184, ABV31934 position 184, ABX11498 position 184. |
| 2007 | ACG59794 position 152, ACG59790 position 152, ACF37320 position 184. |
| 2008 | ACJ67530 position 184, ACG80390 position 184, ACG59786 position 152, ACG80392 position 184, ACJ68807 position 152. |

Example 11

Conservation of SEQ ID NO: 16 in H1N1 Isolates

The applicants surveyed SEQ ID NO: 16 KRWRLFSKH in isolates of H1N1 influenza virus available at www.pubmed.com and found the sequence in the following accession numbers at the listed positions in the following years:

| Year | PubMed Accession Number |
|---|---|
| 1918 | id = 160417491 position 78. |
| 1933 | id = 123824486 position 78. |
| 1934 | id = 119389936 position 29, id = 83288375 position 78. |
| 1935 | id = 229891356 position 78, id = 133754204 position 78. |
| 1936 | id = 229891357 position 78, id = 133754147 position 78. |
| 1942 | id = 89152229 position 78. |
| 1943 | id = 89903071 position 78. |
| 1945 | id = 229891359 position 78, id = 145278825 position 78. |
| 2008 | id = 229891354 position 78. |

Example 12

Conservation of SEQ ID NO: 14 in H1N1 Isolates

The applicants surveyed SEQ ID NO: 14 (HCQKTMN-QVVMPK) in isolates of H1N1 influenza virus available at www.pubmed.com and found the sequence in the following accession numbers at the listed positions in the following years:

| Year | PubMed Accession Number |
|---|---|
| 1918 | id = 160417491 position 41. |
| 1933 | id = 123824486 position 41. |
| 1934 | id = 83288375 position 41. |
| 1935 | id = 229891356 position 41, id = 133754204 position 41. |
| 1936 | id = 229891357 position 41, id = 133754147 position 41. |
| 1940 | id = 123807038 position 41, id = 112787561 position 41. |
| 1942 | id = 89152229 position 41. |
| 1943 | id = 229891358 position 41, id = 133754185 position 41, id = 133752897 position 41. |
| 1947 | id = 89782408 position 41. |

Example 13

Conservation of SEQ ID NO: 15 in H1N1 Isolates

The applicants surveyed SEQ ID NO: 15 (HYQKTMN-QVVMPK) in isolates of H1N1 influenza virus available at www.pubmed.com and found the sequence in the following accession numbers at the listed positions in the following years:

| Year | PubMed Accession Number |
|---|---|
| 1951 | id = 229891360 position 41. |
| 1954 | id = 229891361 position 41. |
| 1977 | id = 123822361 position 41. |
| 1978 | id = 229891364 position 41. |
| 1980 | id = 229891365 position 41. |
| 1983 | id = 229891366 position 41. |

Example 14

Conservation of SEQ ID NO: 17 in H1N1 Isolates

The applicants surveyed SEQ ID NO: 17 (KKKHKLDK) in isolates of H1N1 influenza virus available at www.pubmed.com and found the sequence in the following accession numbers at the listed positions in the following years:

| Year | PubMed Accession Number |
|---|---|
| 1991 | id = 89112485 position 207, id = 194304989 position 207. |
| 1995 | id = 218664225 position 207, id = 194304875 position 207, id = 110733483 position 207, id = 109159406 position 207, id = 94959681 position 207, id = 116069900 position 207, id = 115289364 position 207, id = 113170555 position 207, id = 112787646 position 207, id = 112787580 position 207, id = 110733464 position 207, id = 110733445 position 207, id = 94959662 position 207, id = 109914493 position 207, id = 109159386 position 207, id = 94959624 position 207, id = 91177643 position 207, id = 91124046 position 207, id = 91123250 position 207, id = 91122472 position 207, id = 91122065 position 207, id = 91121655 position 207, id = 91121316 position 207. |
| 1996 | id = 89033025 position 207, id = 134047404 position 207, id = 133752821 position 207, id = 125664153 position 207, id = 125663990 position 207, id = 125663971 position 207, id = 125663952 position 207, id = 94959700 position 207, id = 120434227 position 207, id = 120434208 position 207, id = 120434189 position 207, id = 120434170 position 207, id = 116070014 position 207, id = 116069995 position 207, id = 115344695 position 207, id = 115344676 position 207, id = 115344657 position 207, id = 115344638 position 207, id = 115291099 position 207, id = 112789522 position 207, id = 112789503 position 207, id = 112789484 position 207, id = 112789465 position 207, id = 112789446 position 207, id = 112789427 position 207, id = 109914473 position 207, id = 94959719 position 207. |
| 1997 | id = 89033028 position 207. |
| 1999 | id = 89033031 position 207, id = 237689032 position 207, id = 194304894 position 207, id = 117571163 position 207, id = 115607704 position 207. |
| 2000 | id = 70907655 position 207, id = 157367781 position 207, id = 156536333 position 207, id = 156536314 position 207, id = 152963303 position 207, id = 152963284 position 207, id = 149780459 position 207, id = 149780411 position 207, id = 149780392 position 207, id = 148898156 position 207, id = 148898137 position 207, id = 148898118 position 207, id = 148898099 position 207, id = 145278920 position 207, id = 145278787 position 207, id = 145278633 position 207, id = 133981790 position 207, id = 120433771 position 207, id = 119365477 position 207, id = 119365439 position 207, id = 118313529 position 207, id = 117571239 position 207, id = 117571220 position 207, id = 117571201 position 207, id = 116070033 position 207, id = 116069919 position 207, id = 115607913 position 207, id = 115607894 position 207, id = 115607761 position 207, id = 115521746 position 207, id = 115344714 position 207, id = 115344581 position 207, id = 110733901 position 207, id = 110733882 position 207, id = 110629421 position 207, id = 110629402 position 207, id = 110332401 position 207, id = 109914854 position 207, id = 109675833 position 207, id = 94960118 position 207, id = 94960099 position 207, id = 94960080 position 207, id = 109914454 position 207, id = 109914435 position 207, id = 91119004 position 207, id = 91118985 position 207, id = 90572065 position 207, id = 90572046 position 207, id = 90572027 position 207, id = 90572008 position 207, id = 90571989 position 207, id = 90571970 position 207, id = 90571951 position 207, id = 90571588 position 207, id = 89787876 position 207, id = 89787681 position 207, id = 89787454 position 207, id = 89787205 position 207, id = 89787093 position 207, id = 89786825 position 207, id = 89786625 position 207, id = 89786451 position 207, id = 89786282 position 207, id = 89786036 position 207, id = 89785839 position 207, id = 89785636 position 207, id = 89780995 position 207, id = 89780774 position 207, id = 89780574 position 207, id = 89161178 position 207, id = 89113879 position 207, id = 89113841 position 207, id = 89112390 position 207, id = 89112371 position 207, id = 89112352 position 207, id = 89112333 position 207, id = 89112314 position 207, id = 74477261 position 207, id = 74477242 position 207. |
| 2001 | id = 149780572 position 207, id = 149780543 position 207, id = 133754109 position 207, id = 133754001 position 207, id = 133752878 position 207, id = 133752859 position 207, id = 133752840 position 207, id = 131058547 position 207, id = 131058280 position 207, id = 125664286 position 207, id = 125664172 position 207, id = 122851250 position 207, id = 115521442 position 207, id = 110332529 position 207, id = 109675891 position 207, id = 109675872 position 207, id = 109159726 position 207, id = 106896547 position 207, id = 106896528 position 207, id = 106896509 position 207, id = 106896490 position 207, id = 106896471 position 207, id = 106896452 position 207, id = 106896433 position 207, id = 106896414 position 207, id = 106896395 position 207, id = 106896376 position 207, id = 106896357 position 207, id = 106896338 position 207, id = 94959738 position 207, id = 94959567 position 207, id = 94959548 position 207, id = 109675409 position 207, id = 106896006 position 207, id = 106895987 position 207, id = 106895968 position 207, id = 94959586 position 207, id = 91125115 position 207, id = 91120873 position 207, id = 91120604 position 207, id = 91120229 position 207, id = 91119868 position 207, id = 91119452 position 207, id = 91119118 position 207, id = 91119099 |

| Year | PubMed Accession Number |
|---|---|
| | position 207, id = 91119080 position 207, id = 91119061 position 207, id = 91119042 position 207, id = 91119023 position 207, id = 90572578 position 207, id = 90572559 position 207, id = 90572540 position 207, id = 90572521 position 207, id = 90572502 position 207, id = 90572483 position 207, id = 90572464 position 207, id = 90572445 position 207, id = 90572426 position 207, id = 90572407 position 207, id = 90572388 position 207, id = 90572369 position 207, id = 90572350 position 207, id = 90572331 position 207, id = 90572312 position 207, id = 90572293 position 207, id = 90572274 position 207, id = 90572255 position 207, id = 90572236 position 207, id = 90572217 position 207, id = 90572198 position 207, id = 90572179 position 207, id = 90572160 position 207, id = 90572141 position 207, id = 90572122 position 207, id = 90572103 position 207, id = 90572084 position 207, id = 90571683 position 207, id = 90571664 position 207, id = 90571645 position 207, id = 90571626 position 207, id = 89789031 position 207, id = 89788757 position 207, id = 89788489 position 207, id = 89788291 position 207, id = 89112409 position 207, id = 85857138 position 207, id = 83658790 position 207, id = 77746869 position 207, id = 77543658 position 207, id = 77543378 position 207, id = 83314233 position 207, id = 82542615 position 207, id = 82501517 position 207, id = 82494727 position 207, id = 82494708 position 207, id = 80974058 position 207, id = 77747109 position 207, id = 77747088 position 207, id = 77747069 position 207, id = 77746888 position 207, id = 77543257 position 207, id = 76446835 position 205, id = 76443542 position 207, id = 76411282 position 207, id = 76366065 position 207, id = 76366027 position 207, id = 75213057 position 207, id = 75171465 position 207, id = 74477301 position 207, id = 74477204 position 207, id = 73765608 position 207, id = 73761573 position 207, id = 73665800 position 207, id = 71564895 position 207. |
| 2002 | id = 237689070 position 207, id = 237689051 position 207, id = 237688878 position 207, id = 77543357 position 207, id = 82546790 position 207, id = 73761489 position 207. |
| 2003 | id = 125664191 position 207, id = 122855965 position 207, id = 89112181 position 207, id = 86806725 position 207, id = 83727857 position 207, id = 77747437 position 207, id = 77543313 position 207, id = 82546771 position 207, id = 82501662 position 207, id = 80974115 position 207, id = 77747475 position 207, id = 77746850 position 207, id = 77746831 position 207, id = 76366046 position 207, id = 75216236 position 207, id = 75173042 position 207, id = 75171320 position 207, id = 75168430 position 207, id = 74477223 position 207. |
| 2004 | id = 83744850 position 207. |
| 2005 | id = 149780710 position 207, id = 145278939 position 207, id = 131058820 position 207, id = 115607837 position 207, id = 115607818 position 207, id = 115607799 position 207, id = 115607780 position 207, id = 115289478 position 207, id = 113170897 position 207, id = 112791707 position 207, id = 112788933 position 207, id = 112788895 position 207, id = 112788876 position 207, id = 112788857 position 207. |
| 2006 | id = 226954762 position 207, id = 208344099 position 207, id = 161139460 position 207, id = 161138698 position 207, id = 158524916 position 207, id = 157281311 position 207, id = 157281292 position 207, id = 157281273 position 207, id = 118313208 position 207. |
| 2007 | id = 238837391 position 207, id = 238837372 position 207, id = 237688840 position 207, id = 224400125 position 207, id = 224392744 position 207, id = 224027182 position 207, id = 224027163 position 207, id = 224022190 position 207, id = 224022171 position 207, id = 224022152 position 207, id = 224022130 position 207, id = 224022042 position 207, id = 224020945 position 207, id = 218874700 position 207, id = 194304552 position 207, id = 188504346 position 207, id = 188504008 position 207, id = 188503989 position 207, id = 183396126 position 207, id = 183396107 position 207, id = 183396088 position 207, id = 168480586 position 207, id = 168480897 position 207, id = 168480878 position 207, id = 166079425 position 207, id = 166079406 position 207, id = 166079387 position 207, id = 166079368 position 207, id = 166079330 position 207, id = 163964751 position 207, id = 163964732 position 207, id = 163964713 position 207, id = 163964637 position 207, id = 163964618 position 207, id = 163964599 position 207, id = 163964580 position 207, id = 163964561 position 207, id = 163964542 position 207, id = 163964504 position 207, id = 163964485 position 207, id = 163964466 position 207, id = 163964447 position 207, id = 163964428 position 207, id = 163964409 position 207, id = 163964390 position 207, id = 163964371 position 207, id = 163964333 position 207, id = 161139517 position 207, id = 161139498 position 207, id = 161139479 position 207, id = 161139384 position 207, id = 161139365 position 207, id = 161139346 position 207, id = 161139327 position 207, id = 161139308 position 207, id = 161139289 position 207, id = 161139270 position 207, id = 161139251 position 207, id = 161139232 position 207, id = 161139213 position 207, id = 161139194 position 207, id = 161139175 position 207, id = 161139156 position 207, id = 161139137 position 207, id = 161139118 position 207, id = 161139099 position 207, id = 161139080 position 207, id = 161139061 position 207, id = 161139042 position 207, id = 161139023 position 207, id = 161139004 position 207, id = 161138985 position 207, id = 161138966 position 207, id = 161138947 position 207, id = 161138928 position 207, id = 161138909 position 207, id = 161138890 position 207, id = 161138871 position 207, id = 161138852 position 207, id = 161138833 position 207, id = 161138814 position 207, id = 161138795 position 207, id = 161138776 position 207, id = 161138757 position 207, id = 161138738 position 207, id = 161138717 position 207, id = 161138270 position 207, id = 159150251 position 207, id = 159150232 position 207, id = 159150213 position 207, id = 159150194 position 207, id = 159150175 position 207, id = 159150156 position 207, id = 159150137 position 207, id = 159150099 position 207, id = 159150080 position 207, id = 159150061 position 207, id = 159150042 position 207, id = 159150023 position 207, id = 159150004 position 207, id = 159149985 position 207, id = 159149966 position 207, id = 159149947 position 207, id = 159149909 position 207, id = 159149890 position 207, id = 159149871 position 207, id = 159149833 position 207, id = 159149814 position 207, id = 159149795 position 207, id = 159149776 position 207, id = 159149757 position 207, id = 159149738 position 207, id = 159149719 position 207, id = 159149700 position 207, id = 159149681 position 207, id = 159149662 position 207, id = 159149643 position 207, id = 159149548 position 207, id = 158958091 position 207, id = 158957995 position 207, |

| Year | PubMed Accession Number |
|---|---|
| | id = 158957976 position 207, id = 158957957 position 207, id = 158957938 position 207, id = 158957919 position 207, id = 158957900 position 207, id = 158957881 position 207, id = 158957862 position 207, id = 158957843 position 207, id = 158957824 position 207, id = 158957805 position 207, id = 158957786 position 207, id = 158957767 position 207, id = 158957748 position 207, id = 158957729 position 207, id = 158957710 position 207, id = 158957691 position 207, id = 158957672 position 207, id = 158957653 position 207, id = 158957634 position 207, id = 158957615 position 207, id = 158957596 position 207, id = 158525220 position 207, id = 158525201 position 207, id = 158525182 position 207, id = 158525163 position 207, id = 158525144 position 207, id = 158525125 position 207, id = 158525106 position 207, id = 158525087 position 207, id = 158525068 position 207, id = 158525049 position 207, id = 158524992 position 207, id = 158524973 position 207, id = 158524954 position 207, id = 158524935 position 207, id = 158454518 position 207, id = 158454499 position 207, id = 158454461 position 207, id = 158454423 position 207, id = 158454404 position 207, id = 158454385 position 207, id = 158454347 position 207, id = 158454328 position 207, id = 158454309 position 207, id = 158454290 position 207, id = 158454271 position 207, id = 158454252 position 207, id = 158454233 position 207, id = 158454214 position 207, id = 158454195 position 207, id = 158454176 position 207, id = 158454157 position 207, id = 158454138 position 207, id = 158454119 position 207, id = 158454100 position 207, id = 158454081 position 207, id = 158454062 position 207, id = 158454043 position 207, id = 158454024 position 207, id = 158453986 position 207, id = 158453967 position 207, id = 158453948 position 207, id = 158453929 position 207, id = 158453891 position 207, id = 158453872 position 207, id = 158453853 position 207, id = 158453834 position 207, id = 158453796 position 207, id = 158453758 position 207, id = 158453739 position 207, id = 158453720 position 207, id = 158453701 position 207, id = 158453663 position 207, id = 158453625 position 207, id = 158453606 position 207, id = 158453568 position 207, id = 158453549 position 207, id = 158453530 position 207, id = 158453511 position 207, id = 158453473 position 207, id = 158453454 position 207, id = 158453435 position 207, id = 158453416 position 207, id = 158453378 position 207, id = 158453359 position 207, id = 158453340 position 207, id = 158453321 position 207, id = 158453302 position 207, id = 158453283 position 207, id = 158453264 position 207, id = 158453226 position 207, id = 158453207 position 207, id = 158453188 position 207, id = 158453169 position 207, id = 158453150 position 207, id = 158453112 position 207, id = 158453093 position 207, id = 158453074 position 207, id = 158453055 position 207, id = 158453036 position 207, id = 158453017 position 207, id = 158452916 position 207, id = 158344906 position 207, id = 158344887 position 207, id = 158344868 position 207, id = 158344849 position 207, id = 158344830 position 207, id = 158344811 position 207, id = 158344792 position 207, id = 158344773 position 207, id = 158344754 position 207, id = 158344735 position 207, id = 158344716 position 207, id = 158344697 position 207, id = 157829226 position 207, id = 157368180 position 207, id = 157368161 position 207, id = 157368142 position 207, id = 157368123 position 207, id = 157368104 position 207, id = 157368066 position 207, id = 157368047 position 207, id = 157368028 position 207, id = 157283155 position 207, id = 157283136 position 207, id = 157283117 position 207, id = 157283098 position 207, id = 157283079 position 207, id = 157283060 position 207, id = 157283041 position 207, id = 157283022 position 207, id = 157283003 position 207, id = 157282984 position 207, id = 157282946 position 207, id = 157282927 position 207, id = 157282870 position 207, id = 157282718 position 207, id = 157282699 position 207, id = 157282680 position 207, id = 157282661 position 207, id = 157282642 position 207, id = 157282623 position 207, id = 157282604 position 207, id = 157282585 position 207, id = 157282566 position 207, id = 157282414 position 207, id = 157282395 position 207, id = 157282376 position 207, id = 157282357 position 207, id = 157282338 position 207, id = 157282319 position 207, id = 157282300 position 207, id = 157282262 position 207, id = 157282243 position 207, id = 157282224 position 207, id = 157282167 position 207, id = 157282148 position 207, id = 157282129 position 207, id = 157282110 position 207, id = 157282091 position 207, id = 157282072 position 207, id = 157282053 position 207, id = 157282034 position 207, id = 157282015 position 207, id = 157281996 position 207, id = 157281977 position 207, id = 157281939 position 207, id = 157281882 position 207, id = 157281863 position 207, id = 157281844 position 207, id = 157281825 position 207, id = 157281806 position 207, id = 157281787 position 207, id = 157281730 position 207, id = 157281711 position 207, id = 157281692 position 207, id = 157281673 position 207, id = 157281654 position 207, id = 157281635 position 207, id = 157281616 position 207, id = 157281558 position 207, id = 157281539 position 207, id = 157281520 position 207, id = 157281501 position 207, id = 157281482 position 207, id = 157281463 position 207, id = 157281444 position 207, id = 157281406 position 207, id = 157281387 position 207, id = 157281349 position 207, id = 157281330 position 207, id = 224979373 position 207. |
| 2008 | id = 227293800 position 207, id = 227293763 position 207, id = 256386502 position 207, id = 256386426 position 207, id = 256386730 position 207, id = 256386844 position 207, id = 256386483 position 207, id = 256386217 position 207, id = 256385698 position 207, id = 256385679 position 207, id = 256385660 position 207, id = 256385622 position 207, id = 256385584 position 207, id = 256385527 position 207, id = 256385508 position 207, id = 255529241 position 207, id = 255529222 position 207, id = 255529203 position 207, id = 255529124 position 207, id = 255529029 position 207, id = 255529298 position 207, id = 238821837 position 207, id = 238821818 position 207, id = 237689393 position 207, id = 237689374 position 207, id = 237689355 position 207, id = 237689336 position 207, id = 237689317 position 207, id = 237689279 position 207, id = 237689260 position 207, id = 237689241 position 207, id = 237689146 position 207, id = 237689127 position 207, id = 237689089 position 207, id = 237688975 position 207, id = 237688956 position 207, id = 237688916 position 207, id = 229433780 position 207, id = 227977250 position 207, |

-continued

| Year | PubMed Accession Number |
|---|---|
| | id = 227977231 position 207, id = 227977212 position 207, id = 227977193 position 207, id = 226957774 position 207, id = 226957755 position 207, id = 226957736 position 207, id = 226957717 position 207, id = 226957698 position 207, id = 226954876 position 207, id = 226954857 position 207, id = 226954591 position 207, id = 225907760 position 207, id = 224027258 position 207, id = 224027220 position 207, id = 224021250 position 207. |
| 2009 | id = 256385432 position 207. |

Example 15

Conservation of SEQ ID NO: 13 in H1N1 Isolates

The applicants surveyed SEQ ID NO: 13 (HFQRKRRVRDNVTK) in isolates of H1N1 influenza virus available at www.pubmed.com and found the sequence in the following accession numbers at the listed positions in the following years:

| Year | PubMed Accession Number-Replikin Count |
|---|---|
| 1948 | id = 125976177 position 184. |
| 1949 | id = 125976234 position 184. |
| 1950 | id = 89114311 position 184, id = 145278806 position 184. |
| 1951 | id = 148897966 position 184, id = 146760100 position 184, id = 146133749 position 184, id = 145279092 position 184. |
| 1954 | id = 89112504 position 184, id = 134047499 position 184. |
| 1957 | id = 86793313 position 184. |
| 1977 | id = 90572616 position 184, id = 89112466 position 184, id = 89112447 position 184, id = 133982646 position 184. |
| 1978 | id = 145279034 position 184, id = 133752916 position 184, id = 131059321 position 184, id = 131059087 position 184, id = 125976215 position 184, id = 118313024 position 184, id = 109159444 position 184, id = 94959852 position 184, id = 94959833 position 184, id = 94959814 position 184, id = 94959795 position 184, id = 94959776 position 184. |
| 1980 | id = 133754166 position 184, id = 131059487 position 184, id = 94959871 position 184. |
| 1981 | id = 134047461 position 184. |
| 1982 | id = 90572597 position 184, id = 89782573 position 184, id = 134048464 position 184. |
| 1983 | id = 159149491 position 184, id = 133754128 position 184, id = 133752766 position 184, id = 131059712 position 184, id = 125663865 position 184, id = 125663843 position 184, id = 122852130 position 184, id = 122853012 position 184, id = 122852616 position 184, id = 120434132 position 184, id = 120434113 position 184, id = 120434094 position 184, id = 120434075 position 184, id = 120434056 position 184, id = 120434037 position 184, id = 120434018 position 184, id = 120433999 position 184, id = 119365572 position 184, id = 119365553 position 184, id = 118314391 position 184, id = 118314277 position 184, id = 118314219 position 184, id = 117572802 position 184, id = 117572783 position 184, id = 117572764 position 184, id = 117572728 position 184, id = 117572678 position 184, id = 117572220 position 184, id = 117572162 position 184, id = 117571402 position 184, id = 115289345 position 184, id = 113170574 position 184, id = 112787618 position 184, id = 110733529 position 184, id = 110733510 position 184, id = 94960004 position 184, id = 94959909 position 184, id = 110629007 position 184, id = 94960042 position 184, id = 94960023 position 184, id = 94959890 position 184, id = 94959947 position 184, id = 109159523 position 184, id = 109159499 position 184, id = 94959985 position 184, id = 94959966 position 184, id = 94959928 position 184. |
| 1984 | id = 145278863 position 184, id = 133754242 position 184. |
| 1986 | id = 145278882 position 184, id = 133982626 position 184, id = 133754223 position 184, id = 120434151 position 184. |
| 1987 | id = 146760005 position 184, id = 125663917 position 184, id = 125663890 position 184. |
| 1989 | id = 218664187 position 184. |
| 1991 | id = 89112485 position 184, id = 194304989 position 184. |
| 1995 | id = 218664225 position 184, id = 194304875 position 184, id = 110733483 position 184, id = 109159406 position 184, id = 94959681 position 184, id = 116069900 position 184, id = 115289364 position 184, id = 113170555 position 184, id = 112787646 position 184, id = 112787580 position 184, id = 110733464 position 184, id = 110733445 position 184, id = 94959662 position 184, id = 109914493 position 184, id = 109159386 position 184, id = 94959624 position 184, id = 91177643 position 184, id = 91124046 position 184, id = 91123653 position 184, id = 91123250 position 184, id = 91122472 position 184, id = 91122065 position 184, id = 91121655 position 184, id = 91121316 position 184. |
| 1996 | id = 89033025 position 184, id = 134047404 position 184, id = 133752821 position 184, id = 125664153 position 184, id = 125663990 position 184, id = 125663971 position 184, id = 125663952 position 184, id = 94959700 position 184, id = 120434227 position 184, id = 120434208 position 184, id = 120434189 position 184, id = 120434170 position 184, id = 116070014 position 184, id = 116069995 position 184, id = 115344695 position 184, id = 115344676 position 184, id = 115344657 position 184, id = 115344638 position 184, id = 115291099 position 184, id = 112789522 position 184, id = 112789503 position 184, id = 112789484 position 184, id = 112789465 position 184, id = 112789446 position 184, id = 112789427 position 184, id = 109914473 position 184, id = 94959719 position 184. |

-continued

| Year | PubMed Accession Number-Replikin Count |
|---|---|
| 1997 | id = 89033028 position 184. |
| 1999 | id = 89033031 position 184, id = 237689032 position 184, id = 194304894 position 184, id = 117571163 position 184, id = 115607704 position 184. |
| 2000 | id = 70907655 position 184, id = 157367781 position 184, id = 156536333 position 184, id = 156536314 position 184, id = 152963303 position 184, id = 152963284 position 184, id = 149780459 position 184, id = 149780411 position 184, id = 149780392 position 184, id = 148898156 position 184, id = 148898137 position 184, id = 148898118 position 184, id = 148898099 position 184, id = 145278920 position 184, id = 145278787 position 184, id = 145278633 position 184, id = 133981790 position 184, id = 120433771 position 184, id = 119365477 position 184, id = 119365439 position 184, id = 118313529 position 184, id = 117571239 position 184, id = 117571220 position 184, id = 117571201 position 184, id = 116070033 position 184, id = 116069919 position 184, id = 115607913 position 184, id = 115607894 position 184, id = 115607761 position 184, id = 115521746 position 184, id = 115344714 position 184, id = 115344581 position 184, id = 110733901 position 184, id = 110733882 position 184, id = 110629421 position 184, id = 110629402 position 184, id = 110332401 position 184, id = 109914854 position 184, id = 109675833 position 184, id = 94960118 position 184, id = 94960099 position 184, id = 94960080 position 184, id = 109914454 position 184, id = 109914435 position 184, id = 91119004 position 184, id = 91118985 position 184, id = 90572065 position 184, id = 90572046 position 184, id = 90572027 position 184, id = 90572008 position 184, id = 90571989 position 184, id = 90571970 position 184, id = 90571951 position 184, id = 90571588 position 184, id = 89787876 position 184, id = 89787681 position 184, id = 89787454 position 184, id = 89787205 position 184, id = 89787093 position 184, id = 89786825 position 184, id = 89786625 position 184, id = 89786451 position 184, id = 89786282 position 184, id = 89786036 position 184, id = 89785839 position 184, id = 89785636 position 184, id = 89780995 position 184, id = 89785774 position 184, id = 89780574 position 184, id = 89161178 position 184, id = 89113879 position 184, id = 89113841 position 184, id = 89112390 position 184, id = 89112371 position 184, id = 89112352 position 184, id = 89112333 position 184, id = 89112314 position 184, id = 74477261 position 184, id = 74477242 position 184. |
| 2001 | id = 149780572 position 184, id = 149780543 position 184, id = 133754109 position 184, id = 133754001 position 184, id = 133752878 position 184, id = 133752859 position 184, id = 133752840 position 184, id = 131058547 position 184, id = 131058280 position 184, id = 125664286 position 184, id = 125664172 position 184, id = 122851250 position 184, id = 115521442 position 184, id = 110332529 position 184, id = 109675891 position 184, id = 109675872 position 184, id = 109159726 position 184, id = 106896547 position 184, id = 106896528 position 184, id = 106896509 position 184, id = 106896490 position 184, id = 106896471 position 184, id = 106896452 position 184, id = 106896433 position 184, id = 106896414 position 184, id = 106896395 position 184, id = 106896376 position 184, id = 106896357 position 184, id = 106896338 position 184, id = 94959738 position 184, id = 94959567 position 184, id = 94959548 position 184, id = 109675409 position 184, id = 106896006 position 184, id = 106895987 position 184, id = 106895968 position 184, id = 94959586 position 184, id = 91125115 position 184, id = 91120873 position 184, id = 91120604 position 184, id = 91120229 position 184, id = 91119868 position 184, id = 91119452 position 184, id = 91119181 position 184, id = 91119099 position 184, id = 91119080 position 184, id = 91119061 position 184, id = 91119042 position 184, id = 90572578 position 184, id = 90572559 position 184, id = 90572540 position 184, id = 90572521 position 184, id = 90572502 position 184, id = 90572483 position 184, id = 90572464 position 184, id = 90572445 position 184, id = 90572426 position 184, id = 90572407 position 184, id = 90572388 position 184, id = 90572369 position 184, id = 90572350 position 184, id = 90572331 position 184, id = 90572312 position 184, id = 90572293 position 184, id = 90572274 position 184, id = 90572255 position 184, id = 90572236 position 184, id = 90572217 position 184, id = 90572198 position 184, id = 90572179 position 184, id = 90572160 position 184, id = 90572141 position 184, id = 90572122 position 184, id = 90572103 position 184, id = 90572084 position 184, id = 90571683 position 184, id = 90571664 position 184, id = 90571645 position 184, id = 90571626 position 184, id = 89789031 position 184, id = 89788757 position 184, id = 89788489 position 184, id = 89788291 position 184, id = 89112409 position 184, id = 85857138 position 184, id = 83658790 position 184, id = 77746869 position 184, id = 77543658 position 184, id = 77543378 position 184, id = 83314233 position 184, id = 82542615 position 184, id = 82501517 position 184, id = 82494727 position 184, id = 82494708 position 184, id = 80974058 position 184, id = 77747109 position 184, id = 77747088 position 184, id = 77747069 position 184, id = 77746888 position 184, id = 77543257 position 184, id = 76446835 position 182, id = 76443542 position 184, id = 76411282 position 184, id = 76366065 position 184, id = 76366027 position 184, id = 75213057 position 184, id = 75171465 position 184, id = 74477301 position 184, id = 74477204 position 184, id = 73765608 position 184, id = 73761573 position 184, id = 73665800 position 184, id = 71564895 position 184. |
| 2002 | id = 237689070 position 184, id = 237689051 position 184, id = 237688878 position 184, id = 77543357 position 184, id = 82546790 position 184, id = 73761489 position 184. |
| 2003 | id = 125664191 position 184, id = 122855965 position 184, id = 89112181 position 184, id = 86806725 position 184, id = 83727857 position 184, id = 77747437 position 184, id = 77543313 position 184, id = 73763210 position 184, id = 82546771 position 184, id = 82501662 position 184, id = 80974115 position 184, id = 77747475 position 184, id = 77746850 position 184, id = 77746831 position 184, id = 76366046 position 184, id = 75216236 position 184, id = 75173042 position 184, id = 75171320 position 184, id = 75168430 position 184, id = 74477223 position 184. |
| 2004 | id = 83744850 position 184, id = 151335599 position 184. |
| 2005 | id = 149780710 position 184, id = 145278939 position 184, id = 131058820 position 184, id = 131052868 position 184, id = 117572954 position 184, id = 115607837 position 184, id = 115607799 position 184, id = 115607780 position 184, id = 115521499 position 184, id = 115289478 position 184, id = 113170897 position 184, id = 112791707 position 184, id = 112788933 position 184, id = 112788914 position 184, id = 112788895 position 184, id = 112788876 position 184, id = 112788857 position 184. |

| Year | PubMed Accession Number-Replikin Count |
|---|---|
| 2006 | id = 151335580 position 184, id = 226954762 position 184, id = 208344099 position 184, id = 161139460 position 184, id = 161138698 position 184, id = 158524916 position 184, id = 157281311 position 184, id = 157281292 position 184, id = 157281273 position 184, id = 118313208 position 184. |
| 2007 | id = 238837391 position 184, id = 238837372 position 184, id = 237688840 position 184, id = 224400125 position 184, id = 224392744 position 184, id = 224027182 position 184, id = 224027163 position 184, id = 224022190 position 184, id = 224022171 position 184, id = 224022152 position 184, id = 224022130 position 184, id = 224022042 position 184, id = 218874700 position 184, id = 194304552 position 184, id = 188504346 position 184, id = 188504008 position 184, id = 188503989 position 184, id = 183396126 position 184, id = 183396107 position 184, id = 183396088 position 184, id = 169822586 position 184, id = 168480897 position 184, id = 168480878 position 184, id = 166079425 position 184, id = 166079406 position 184, id = 166079387 position 184, id = 166079368 position 184, id = 166079330 position 184, id = 163964751 position 184, id = 163964713 position 184, id = 163964637 position 184, id = 163964618 position 184, id = 163964599 position 184, id = 163964580 position 184, id = 163964561 position 184, id = 163964542 position 184, id = 163964504 position 184, id = 163964485 position 184, id = 163964466 position 184, id = 163964447 position 184, id = 163964428 position 184, id = 163964409 position 184, id = 163964390 position 184, id = 163964371 position 184, id = 163964333 position 184, id = 161139517 position 184, id = 161139498 position 184, id = 161139479 position 184, id = 161139384 position 184, id = 161139365 position 184, id = 161139346 position 184, id = 161139327 position 184, id = 161139308 position 184, id = 161139289 position 184, id = 161139270 position 184, id = 161139251 position 184, id = 161139232 position 184, id = 161139213 position 184, id = 161139194 position 184, id = 161139175 position 184, id = 161139156 position 184, id = 161139137 position 184, id = 161139118 position 184, id = 161139099 position 184, id = 161139080 position 184, id = 161139061 position 184, id = 161139042 position 184, id = 161139023 position 184, id = 161139004 position 184, id = 161138985 position 184, id = 161138966 position 184, id = 161138947 position 184, id = 161138928 position 184, id = 161138909 position 184, id = 161138890 position 184, id = 161138871 position 184, id = 161138852 position 184, id = 161138833 position 184, id = 161138814 position 184, id = 161138795 position 184, id = 161138776 position 184, id = 161138757 position 184, id = 161138738 position 184, id = 161138717 position 184, id = 159150270 position 184, id = 159150251 position 184, id = 159150232 position 184, id = 159150213 position 184, id = 159150194 position 184, id = 159150175 position 184, id = 159150156 position 184, id = 159150137 position 184, id = 159150099 position 184, id = 159150080 position 184, id = 159150061 position 184, id = 159150042 position 184, id = 159150023 position 184, id = 159150004 position 184, id = 159149985 position 184, id = 159149966 position 184, id = 159149947 position 184, id = 159149909 position 184, id = 159149890 position 184, id = 159149871 position 184, id = 159149833 position 184, id = 159149814 position 184, id = 159149795 position 184, id = 159149776 position 184, id = 159149757 position 184, id = 159149738 position 184, id = 159149719 position 184, id = 159149700 position 184, id = 159149681 position 184, id = 159149662 position 184, id = 159149643 position 184, id = 159149548 position 184, id = 158958091 position 184, id = 158957995 position 184, id = 158957976 position 184, id = 158957957 position 184, id = 158957938 position 184, id = 158957919 position 184, id = 158957900 position 184, id = 158957881 position 184, id = 158957862 position 184, id = 158957843 position 184, id = 158957824 position 184, id = 158957805 position 184, id = 158957786 position 184, id = 158957767 position 184, id = 158957748 position 184, id = 158957729 position 184, id = 158957710 position 184, id = 158957691 position 184, id = 158957672 position 184, id = 158957653 position 184, id = 158957634 position 184, id = 158957615 position 184, id = 158957596 position 184, id = 158525220 position 184, id = 158525201 position 184, id = 158525182 position 184, id = 158525163 position 184, id = 158525144 position 184, id = 158525125 position 184, id = 158525106 position 184, id = 158525087 position 184, id = 158525068 position 184, id = 158525049 position 184, id = 158525030 position 184, id = 158524992 position 184, id = 158524973 position 184, id = 158524954 position 184, id = 158524935 position 184, id = 158454518 position 184, id = 158454499 position 184, id = 158454461 position 184, id = 158454423 position 184, id = 158454404 position 184, id = 158454385 position 184, id = 158454347 position 184, id = 158454328 position 184, id = 158454309 position 184, id = 158454290 position 184, id = 158454271 position 184, id = 158454252 position 184, id = 158454233 position 184, id = 158454214 position 184, id = 158454195 position 184, id = 158454176 position 184, id = 158454157 position 184, id = 158454138 position 184, id = 158454119 position 184, id = 158454100 position 184, id = 158454081 position 184, id = 158454062 position 184, id = 158454043 position 184, id = 158454024 position 184, id = 158453986 position 184, id = 158453967 position 184, id = 158453948 position 184, id = 158453929 position 184, id = 158453891 position 184, id = 158453872 position 184, id = 158453853 position 184, id = 158453834 position 184, id = 158453796 position 184, id = 158453758 position 184, id = 158453739 position 184, id = 158453720 position 184, id = 158453701 position 184, id = 158453663 position 184, id = 158453606 position 184, id = 158453568 position 184, id = 158453549 position 184, id = 158453530 position 184, id = 158453511 position 184, id = 158453473 position 184, id = 158453454 position 184, id = 158453435 position 184, id = 158453416 position 184, id = 158453378 position 184, id = 158453359 position 184, id = 158453340 position 184, id = 158453321 position 184, id = 158453302 position 184, id = 158453283 position 184, id = 158453264 position 184, id = 158453226 position 184, id = 158453207 position 184, id = 158453188 position 184, id = 158453169 position 184, id = 158453150 position 184, id = 158453112 position 184, id = 158453093 position 184, id = 158453074 position 184, id = 158453055 position 184, id = 158453036 position 184, id = 158453017 position 184, |

| Year | PubMed Accession Number-Replikin Count |
|---|---|
| | id = 158452916 position 184, id = 158344906 position 184, id = 158344887 position 184, id = 158344868 position 184, id = 158344849 position 184, id = 158344830 position 184, id = 158344811 position 184, id = 158344792 position 184, id = 158344773 position 184, id = 158344754 position 184, id = 158344735 position 184, id = 158344716 position 184, id = 158344697 position 184, id = 157829226 position 184, id = 157368180 position 184, id = 157368161 position 184, id = 157368142 position 184, id = 157368123 position 184, id = 157368104 position 184, id = 157368066 position 184, id = 157368047 position 184, id = 157368028 position 184, id = 157283155 position 184, id = 157283136 position 184, id = 157283117 position 184, id = 157283098 position 184, id = 157283079 position 184, id = 157283060 position 184, id = 157283041 position 184, id = 157283022 position 184, id = 157283003 position 184, id = 157282984 position 184, id = 157282946 position 184, id = 157282927 position 184, id = 157282870 position 184, id = 157282718 position 184, id = 157282699 position 184, id = 157282680 position 184, id = 157282661 position 184, id = 157282642 position 184, id = 157282623 position 184, id = 157282604 position 184, id = 157282585 position 184, id = 157282566 position 184, id = 157282414 position 184, id = 157282395 position 184, id = 157282376 position 184, id = 157282357 position 184, id = 157282338 position 184, id = 157282319 position 184, id = 157282300 position 184, id = 157282243 position 184, id = 157282224 position 184, id = 157282167 position 184, id = 157282148 position 184, id = 157282129 position 184, id = 157282110 position 184, id = 157282091 position 184, id = 157282072 position 184, id = 157282053 position 184, id = 157282034 position 184, id = 157282015 position 184, id = 157281977 position 184, id = 157281939 position 184, id = 157281882 position 184, id = 157281863 position 184, id = 157281844 position 184, id = 157281825 position 184, id = 157281806 position 184, id = 157281787 position 184, id = 157281730 position 184, id = 157281711 position 184, id = 157281692 position 184, id = 157281673 position 184, id = 157281654 position 184, id = 157281635 position 184, id = 157281616 position 184, id = 157281558 position 184, id = 157281539 position 184, id = 157281520 position 184, id = 157281501 position 184, id = 157281482 position 184, id = 157281463 position 184, id = 157281444 position 184, id = 157281406 position 184, id = 157281387 position 184, id = 157281349 position 184, id = 157281330 position 184, id = 224979373 position 184. |
| 2008 | id = 227293800 position 184, id = 227293763 position 184, id = 256386502 position 184, id = 256386426 position 184, id = 256386844 position 184, id = 256386730 position 184, id = 256386483 position 184, id = 256386217 position 184, id = 256385698 position 184, id = 256385679 position 184, id = 256385660 position 184, id = 256385622 position 184, id = 256385584 position 184, id = 256385527 position 184, id = 256385508 position 184, id = 255529241 position 184, id = 255529222 position 184, id = 255529203 position 184, id = 255529124 position 184, id = 255529029 position 184, id = 237689298 position 184, id = 238821837 position 184, id = 238821818 position 184, id = 237689393 position 184, id = 237689374 position 184, id = 237689355 position 184, id = 237689336 position 184, id = 237689317 position 184, id = 237689279 position 184, id = 237689260 position 184, id = 237689241 position 184, id = 237689146 position 184, id = 237689127 position 184, id = 237689089 position 184, id = 237688975 position 184, id = 237688956 position 184, id = 237688916 position 184, id = 229433780 position 184, id = 227977250 position 184, id = 227977231 position 184, id = 227977212 position 184, id = 227977193 position 184, id = 226957774 position 184, id = 226957755 position 184, id = 226957736 position 184, id = 226957717 position 184, id = 226957698 position 184, id = 226954876 position 184, id = 226954857 position 184, id = 226954591 position 184, id = 225907760 position 184, id = 224027258 position 184, id = 224027220 position 184, id = 224021250 position 184. |
| 2009 | id = 256385432 position 184. |

What is claimed is:

1. A method of preventing or treating influenza virus in a subject comprising administering to said subject in a pharmaceutically-acceptable excipient an effective amount of at least one first isolated or chemically synthesized peptide isolated from a hemagglutinin protein of an isolate of influenza virus and at least one second isolated or chemically synthesized peptide isolated from a pB1 protein of an isolate of influenza virus, wherein said first and second isolated or chemically synthesized peptides each consist of a Replikin sequence, wherein said Replikin sequences are defined as an amino acid sequence of up to 50 amino acid residues comprising:

(1) at least one lysine residue located at a first terminus of said sequence and at least one lysine residue or at least one histidine residue located at a second terminus of said sequence;

(2) a first lysine residue located six to ten residues from a second lysine residue;

(3) at least one histidine residue; and (4) at least 6% lysine residues, and wherein said at least one first isolated or chemically synthesized peptide comprises at least one peptide sequence of SEQ ID NO(s): 1-6 and said at least one second isolated or chemically synthesized peptide comprises at least one peptide sequence of SEQ ID NO(s): 7-12.

2. The method of claim 1, wherein said at least one first isolated or chemically synthesized peptide consists essentially of SEQ ID NO: 1, SEQ ID NO: 2, SEQ ID NO: 3, SEQ ID NO: 4, SEQ ID NO: 5, or SEQ ID NO: 6 and said at least one second isolated or chemically synthesized peptide consists essentially of SEQ ID NO: 7, SEQ ID NO: 8, SEQ ID ON: 9, SEQ ID NO: 10, SEQ ID NO: 11, or SEQ ID NO: 12.

3. The method of claim 1, wherein said at least one first isolated or chemically synthesized peptide consists of SEQ ID NO: 1, SEQ ID NO: 2, SEQ ID NO: 3, SEQ ID NO: 4, SEQ ID NO: 5, or SEQ ID NO: 6 and said at least one second isolated or chemically synthesized peptide consists of SEQ ID NO: 7, SEQ ID NO: 8, SEQ ID ON: 9, SEQ ID NO: 10, SEQ ID NO: 11, or SEQ ID NO: 12.

4. The method of claim 2, wherein at least two isolated or chemically synthesized peptides consisting essentially of SEQ ID NO: 1, SEQ ID NO: 2, SEQ ID NO: 3, SEQ ID NO: 4, SEQ ID NO: 5, or SEQ ID NO: 6 and at least two isolated or synthesized peptides consisting essentially of SEQ ID NO: 7, SEQ ID NO: 8, SEQ ID ON: 9, SEQ ID NO: 10, SEQ ID NO: 11, or SEQ ID NO: 12 are administered.

5. The method of claim 3, wherein at least two isolated or chemically synthesized peptides consisting of SEQ ID NO: 1, SEQ ID NO: 2, SEQ ID NO: 3, SEQ ID NO: 4, SEQ ID NO: 5, or SEQ ID NO: 6 and at least two isolated or synthesized peptides consisting of SEQ ID NO: 7, SEQ ID NO: 8, SEQ ID ON: 9, SEQ ID NO: 10, SEQ ID NO: 11, or SEQ ID NO: 12 are administered.

6. The method of claim 4 wherein a mixture of isolated or chemically synthesized peptides consisting essentially of each of SEQ ID NO(s): 1-12 is administered.

7. The method of claim 5 wherein a mixture of isolated or chemically synthesized peptides of each of SEQ ID NO(s): 1-12 is administered.

8. The method of claim 1, wherein a vaccine comprising a mixture of isolated or chemically synthesized peptides consisting essentially of each of SEQ ID NO(s): 1-12 and a pharmaceutically acceptable excipient is administered.

9. The method of claim 1, wherein a vaccine comprising a mixture of isolated or chemically synthesized peptides of each of SEQ ID NO(s): 1-12 is administered.

10. The method of claim 9, wherein said vaccine comprises an approximate equal molar mixture of the isolated or chemically synthesized peptides of SEQ ID NO(s): 1-12.

11. The method of claim 9, wherein said vaccine comprises approximately equal weight of the isolated peptides of SEQ ID NO(s): 1-12.

12. The method of claim 11, wherein said vaccine comprises about 10% by weight SEQ ID NO: 1, about 9% by weight SEQ ID NO: 2, about 10% by weight SEQ ID NO: 3, about 6% by weight SEQ ID NO: 4, about 8% by weight SEQ ID NO: 5, about 8% by weight SEQ ID NO: 6, about 7% by weight SEQ ID NO: 7, about 6% by weight SEQ ID NO: 8, about 10% by weight SEQ ID NO: 9, about 8% by weight SEQ ID NO: 10, about 7% by weight SEQ ID NO: 11, and about 11% by weight SEQ ID NO: 12, wherein the percent by weight is based on the weight of said mixture of peptides.

13. The method of claim 8 wherein administration of said vaccine blocks transmission of influenza from one animal host to another animal host thereby blocking the formation of a reservoir of influenza.

14. The method of claim 8 directed against H1N1, H1N2, H2N2, H3N2, H3N8, H5N1, H5N2, H7N7, H7N2, H7N3, H9N2, H10N7, or any other strain of influenza A virus.

15. The method of claim 1 wherein said at least one first isolated or chemically synthesized peptide and said at least one second isolated or chemically synthesized peptide are the sole immunogenic materials in said composition.

16. The method of claim 8 wherein said vaccine is sterile and substantially free of pyrogens.

17. The method of claim 8 wherein said vaccine is substantially free of cellular debris or materials.

18. The method of claim 8 wherein said vaccine is free of avian proteins found in vaccines produced from growth in bird eggs.

19. The method of claim 1, wherein said first and second isolated or chemically synthesized peptide are chemically synthesized by solid phase methods.

20. The method of claim 1, wherein said pharmaceutically acceptable excipient is water.

21. The method of claim 1, wherein said administration is parenteral, intradermal, subcutaneous, intramuscular, nasal, oral, bronchial, ophthalmic, transdermal, transmucosal, intravenous, or topical.

22. The method of claim 21, wherein said administration is intranasal, intraocular, or via spray inhalation.

* * * * *